United States Patent
Branca et al.

(10) Patent No.: US 8,470,823 B2
(45) Date of Patent: Jun. 25, 2013

(54) SATURATED BICYCLIC HETEROCYCLIC DERIVATIVES AS SMO ANTAGONISTS

(75) Inventors: Danila Branca, Rome (IT); Federica Ferrigno, Rome (IT); Jose Ignacio Martin Hernando, Rome (IT); Philip Jones, Brookline, MA (US); Olaf Kinzel, Rome (IT); Savina Malancona, Rome (IT); Ester Muraglia, Rome (IT); Maria Cecilia Palumbi, Rome (IT); Giovanna Pescatore, Rome (IT); Rita Scarpelli, Rome (IT)

(73) Assignee: Instituto di Ricerche di Biologia Molecolare P. Angeletti S.R.L., Rome (IT)

( * ) Notice: Subject to any disclaimer, the term of this patent is extended or adjusted under 35 U.S.C. 154(b) by 107 days.

(21) Appl. No.: 13/060,718

(22) PCT Filed: Aug. 28, 2009

(86) PCT No.: PCT/GB2009/051079
§ 371 (c)(1),
(2), (4) Date: Apr. 13, 2011

(87) PCT Pub. No.: WO2010/023480
PCT Pub. Date: Mar. 4, 2010

(65) Prior Publication Data
US 2011/0183989 A1 Jul. 28, 2011

(30) Foreign Application Priority Data

Aug. 29, 2008 (GB) .................................... 0815700.0
Nov. 28, 2008 (GB) .................................... 0821817.4

(51) Int. Cl.
*A61K 31/4985* (2006.01)
(52) U.S. Cl.
USPC .......................................... 514/249; 544/350
(58) Field of Classification Search
USPC ........................................................ 544/350
See application file for complete search history.

(56) References Cited

U.S. PATENT DOCUMENTS

| | | | |
|---|---|---|---|
| 7,691,887 B2 | 4/2010 | Balkovec et al. | |
| 2003/0114420 A1 | 6/2003 | Salvati et al. | |
| 2004/0077606 A1 | 4/2004 | Salvati et al. | |

FOREIGN PATENT DOCUMENTS

| | | |
|---|---|---|
| EP | 1159964 B1 | 10/2009 |
| WO | 0200617 A2 | 1/2002 |
| WO | 0200653 A2 | 1/2002 |
| WO | 03030907 A1 | 4/2003 |
| WO | 2006078283 A2 | 7/2006 |
| WO | 2007056593 A2 | 5/2007 |
| WO | 2007120827 A2 | 10/2007 |

OTHER PUBLICATIONS

Reaxys database entry for Schischkin; Wysotschin: Izvestiya Sibirskogo Otdeleniya Akademii Nauk SSSR, Seriya Khimicheskikh Nauk, vol. 6 (1978), pp. 113-115.
Salvati, ME et al., Bioorganic & Medicinal Chemistry, vol. 18 (2008), pp. 1910-1915, "Identification and optimization of a novel series of [2.2.1]-oxabicyclo imide-based androgen receptor antagonists".
Prevost, GP et al., Cancer Research, vol. 66, No. 18 (2006), pp. 9227-9234, "Anticancer activity of BIM-46174, a new inhibitor of the heterotrimeric G(alpha)/G(beta,gamma) protein complex".

*Primary Examiner* — Brian McDowell
(74) *Attorney, Agent, or Firm* — Laura M. Ginkel; David A. Muthard

(57) ABSTRACT

The present invention relates to compounds of formula I: and pharmaceutically acceptable salts or tautomers thereof which are inhibitors of the Sonic Hedgehog pathway, in particular Smoantagonists. Thus the compounds of this invention are useful for the treatment of diseases associated with abnormal hedgehog pathway activation, including cancer, for example basal cell carcinoma, medulloblastoma, prostate, pancreatic, breast, colon, bone and small cell lung cancers, and cancers of the upper GI tract.

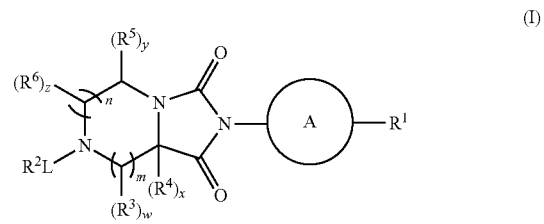

9 Claims, No Drawings

SATURATED BICYCLIC HETEROCYCLIC DERIVATIVES AS SMO ANTAGONISTS

The present invention relates to saturated bicyclic heterocyclic derivatives which are inhibitors of the Sonic Hedgehog pathway, in particular they function as Smoothened (Smo) antagonists. Thus the compounds of this invention are useful for the treatment of diseases associated with abnormal hedgehog pathway activation, including cancer, for example basal cell carcinoma, medulloblastoma, prostate, pancreatic, breast, colon, bone and small cell lung cancers, and cancers of the upper GI tract.

Hedgehog proteins (Hh) are secreted signaling proteins first discovered in *Drosophila*. They are highly hydrophobic proteins which after secretion can diffuse and establish gradients in tissues that have a paramount role in the proper development of the embryo. Three Hh homologues with different spatial and temporal distribution patterns have been identified in humans: Sonic hedgehog (SHH), Indian hedgehog (IHH) and Desert hedgehog (DHH).

The Hh signaling cascade is initiated upon binding of Hh to its receptor Patched (Ptch). In the absence of Hh, Ptch inhibits the activity of another membrane spanning protein, Smoothened (Smo) which is a key mediator of Hh signaling. Smo has a structure reminiscent of the G-protein-coupled receptor (GPCR) superfamily, but is not involved in the binding of any Hhs. When Hh is present it binds to Ptch to form an inactive complex, relieving Ptch's inhibition of Smo and activating the Hh response pathway. The Hh signal is then transmitted via a protein complex to the transcription factor cubitus interrupts (Ci) in *Drosophila* and GLI transcription factors in mammals. In the absence of Hh signaling Ci is cleaved and the amino terminal fragment acts as an inhibitor of Hh target gene transcription. Upon Hh signaling the cleavage of Ci is prevented and Ci becomes an activator of target gene transcription.

Whereas embryonic loss of SHH signaling can result in cyclopia and other developmental defects (Chiang C et al. *Nature* 383:407-413 (1996)), inappropriate activation of the SHH pathway is believed to lead to increased cell proliferation and tumor formation and is associated with many different types of malignancies, including basal cell carcinoma (BCC), medulloblastoma, pancreatic cancer, small lung cancer, prostate cancer (PC), breast cancer, digestive tract tumors and skin cancer (Kiselyov A S *Anti-cancer Agents in Medicinal Chemistry* 6:445-449 (2006) and Sidransky D *Nature Genet.* 14:7-8 (1996)). Thus, the Hh pathway is an important pharmacological target for a variety of conditions.

Aberrant activation of the Hh pathways in cancer are considered to be caused either by mutations in the pathway (ligand independent) or through Hh overexpression (ligand dependent).

Mutations in Ptch 1 have been connected to nevoid basal cell carcinomas syndrome (also called Gorlin syndrome), a condition characterized by a number of development defects and a predisposition for developing numerous basal cell carcinomas (BCC), medulloblastoma, rhabdomyosarcoma and several other neoplasms. Mutations which inactivate Ptch and activate Smo have also been found in sporadic BCC and medulloblastoma, and a number of other sporadic tumors (Reifenberger J et al. *Cancer Res.* 58:1798-1803 (1998) and Xie J et al. *Nature* 391:90-92 (1998)).

Plant-derived teratogenic alkaloids cyclopamine and jervine have been proven to cause holoprosencephaly by direct inhibition of SHH signaling (Cooper M K et al. *Science* 280:1603-1607 (1998) and Incardona J P et al. *Development* 125:3553-3562 (1998)) by binding to Smo (Chen J K et al. *Genes Dev.* 16:2743-2748 (2002)). In vitro tests have shown that the teratogen cyclopamine can inhibit the abnormal cell growth of fibroblast cells from Ptch$^{-/-}$ mice, several glioblastoma/glioma cell lines, medulloblastoma cell lines, squamous cell carcinoma cell lines and SCLC cell lines (Bak M et al. *Pharmacogenomics* 4(4):411-429 (2003)). Cyclopamine has also displayed efficacy in vivo in the models of medulloblastoma (Dahmane N et al. *Development* 128:5201-5212 (2001) and Berman C M et al. *Science* 297:1559-1561 (2002)). Synthetic Hh antagonists have been identified in SHH responsive cell models, some targeting Smo (Chen J K et al. *Proc. Natl. Acad. Sci. USA* 99:14071-14076 (2002), Frank-Kamenetsky M et al. *J. Biol.* 1:10 (2002) and Williams J A et al. *Proc. Natl. Acad. Sci. USA* 100:4616-4621 (2003)) and others an unknown target downstream of Smo (Chen J K et al. *Proc. Natl. Acad. Sci. USA* 99:14071-14076 (2002)).

Reports have shown that Hh overexpression, sometimes accompanied by increased expression of Hh target genes, is detected in a broad spectrum of human tumor biopsies and cell lines, including small cell lung carcinoma, pancreatic adenocarcinoma, oesophageal, stomach and biliary tract cancers, prostate cancer, breast cancer, colon cancer and liver cancer (Rubin L L et al. *Nature Reviews Drug Discovery* 5:1026-33 (2006)).

The compounds of the present invention are inhibitors of the Hh pathway, in particular Smo antagonists.

The present invention provides a compound of structural formula I:

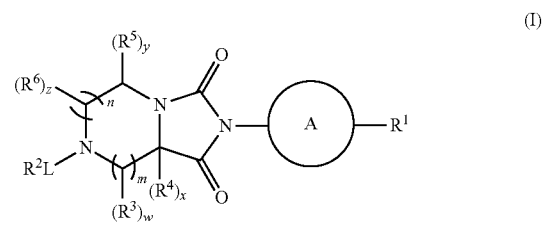

(I)

wherein:
each of m and n is independently 1 or 2;
each of w, y and z is independently 0, 1 or 2;
x is 0 or 1;
A is $C_{3-7}$cycloalkyl or fluoro$C_{3-7}$cycloalkyl;
L is —$(X\!\!=\!\!O)_a(NR^7)_b(O)_c(CR^8R^9)_d(NR^7)_e$—;
a is 0 or 1;
b is 0 or 1;
c is 0 or 1;
d is 0, 1, 2, 3, 4, 5 or 6;
e is 0 or 1;
$R^1$ is $C_{1-6}$alkyl, halo$C_{1-6}$alkyl or a ring which is: $C_{6-10}$aryl; $C_{3-10}$cycloalkyl; oxetanyl; azetidinyl; a 5 or 6 membered saturated or partially saturated heterocyclic ring containing one, two or three heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing one, two or three N atoms; or a 7-15 membered unsaturated, partially saturated or saturated heterocyclic ring containing one, two, three or four heteroatoms independently selected from N, O and S; any of which rings being optionally substituted by one, two or three groups independently selected from $R^{10}$;

$R^2$ is a $C_{1-10}$alkyl, halo$C_{1-10}$alkyl, $C_{1-6}$alkylmercapto$C_{1-6}$alkyl, $C_{2-10}$alkenyl or a ring which is: $C_{3-10}$cycloalkyl; $C_{6-10}$aryl; oxetanyl; azetidinyl; a 5 or 6 membered saturated or partially saturated heterocyclic ring containing one, two or three heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing one, two or three N atoms; or a 7-15 membered saturated, partially saturated or unsaturated heterocyclic ring containing one, two, three or four heteroatoms independently selected from N, O and S; any of which rings being optionally substituted by one, two, three or four groups independently selected from $R^{11}$;

each of $R^3$, $R^4$, $R^5$ and $R^6$ is independently $C_{1-6}$alkyl, $C_{2-10}$alkenyl, halo$C_{1-6}$alkyl, hydroxy$C_{1-6}$alkyl, $C_{1-6}$alkoxy, $C_{1-6}$alkoxy$C_{1-6}$alkyl, carboxy, $CO_2R^a$, $CONR^aR^b$, $S(O)_rR^a$ or $S(O)_rNR^aR^b$;

r is 0, 1 or 2;

$R^7$ is hydrogen or $C_{1-6}$alkyl;

each of $R^8$ and $R^9$ is independently hydrogen, $C_{1-6}$alkyl, $C_{1-6}$alkoxy, $C_{1-6}$alkoxycarbonyl or halo$C_{1-6}$alkyl;

each $R^{10}$ is independently hydroxy, cyano, halogen, $C_{1-6}$alkyl, halo$C_{1-6}$alkyl, $OR^a$ or $NR^aR^b$;

each $R^{11}$ is independently hydroxy, oxo, cyano, halogen, $C_{1-6}$alkyl, $C_{1-6}$alkylcarbonyl, $C_{2-10}$alkenyl, $C_{2-10}$alkynyl, halo$C_{1-6}$alkyl, hydroxy$C_{1-6}$alkyl, carboxy, nitro, $OR^a$, $NR^aR^b$, $NR^aCOR^b$, $NR^aS(O)_rR^b$, $NR^aS(O)_rNR^aR^b$, $CO_2R^a$, $CONR^aR^b$, $S(O)_rR^a$, $S(O)_rNR^aR^b$ or a ring which is: $C_{3-10}$cycloalkyl, $C_{6-10}$aryl, $C_{6-10}$aryloxy, $C_{6-10}$aryl$C_{1-6}$alkoxy, $C_{6-10}$aryl$C_{1-6}$alkyl, azetidinyl, a 5 or 6 membered saturated or partially saturated heterocyclic ring containing one, two or three heteroatoms independently selected from N, O and S, a 5 membered heteroaromatic ring containing 1, 2, 3 or 4 heteroatoms independently selected from N, O and S, not more than one heteroatom of which is O or S or a 6 membered heteroaromatic ring containing one, two or three N atoms; any of which rings being optionally substituted by one, two or three groups independently selected from hydroxy, oxo, cyano, halogen, $C_{1-6}$alkyl, $C_{1-6}$alkylsulfonyl, halo$C_{1-6}$alkyl, $C_{1-6}$alkoxy and halo$C_{1-6}$alkoxy;

X is C or S=O;

each of $R^a$ and $R^b$ is independently hydrogen, $C_{1-6}$alkyl, $C_{1-6}$alkylcarbonyl, halo$C_{1-6}$alkyl, hydroxy$C_{1-6}$alkyl, $C_{3-10}$cycloalkyl or $C_{6-10}$aryl, any of which rings being optionally substituted by one, two or three groups independently selected from halogen and $C_{1-6}$alkyl;

or a pharmaceutically acceptable salt, stereoisomer or tautomer thereof.

In an embodiment:

each of $R^3$, $R^4$, $R^5$ and $R^6$ is independently $C_{1-6}$alkyl, $C_{2-10}$alkenyl, halo$C_{1-6}$alkyl, hydroxy$C_{1-6}$alkyl, carboxy, $CO_2R^a$, $CONR^aR^b$, $S(O)_rR^a$ or $S(O)_rNR^aR^b$;

each $R^{11}$ is independently hydroxy, oxo, cyano, halogen, $C_{1-6}$alkyl, $C_{1-6}$alkylcarbonyl, $C_{2-10}$alkenyl, $C_{2-10}$alkynyl, halo$C_{1-6}$alkyl, hydroxy$C_{1-6}$alkyl, carboxy, nitro, $OR^a$, $NR^aR^b$, $NR^aCOR^b$, $NR^aS(O)_rR^b$, $NR^aS(O)_rNR^aR^b$, $CO_2R^a$, $CONR^aR^b$, $S(O)_rR^a$, $S(O)_rNR^aR^b$ or a ring which is: $C_{3-10}$cycloalkyl, $C_{6-10}$aryl, $C_{6-10}$aryloxy, $C_{6-10}$aryl$C_{1-6}$alkoxy, azetidinyl, a 5 or 6 membered saturated or partially saturated heterocyclic ring containing one, two or three heteroatoms independently selected from N, O and S, a 5 membered heteroaromatic ring containing 1, 2, 3 or 4 heteroatoms independently selected from N, O and S, not more than one heteroatom of which is O or S or a 6 membered heteroaromatic ring containing one, two or three N atoms; any of which rings being optionally substituted by one, two or three groups independently selected from hydroxy, oxo, cyano, halogen, $C_{1-6}$alkyl, $C_{1-6}$alkylsulfonyl, halo$C_{1-6}$alkyl, $C_{1-6}$alkoxy and halo$C_{1-6}$alkoxy;

each of $R^a$ and $R^b$ is independently hydrogen, $C_{1-6}$alkyl, $C_{1-6}$alkylcarbonyl, halo$C_{1-6}$alkyl, hydroxy$C_{1-6}$alkyl or $C_{3-10}$cycloalkyl;

or a pharmaceutically acceptable salt, stereoisomer or tautomer thereof.

In an embodiment of each previous embodiment:

$R^2$ is a $C_{1-10}$alkyl, halo$C_{1-10}$alkyl, $C_{1-6}$alkylmercapto$C_{1-6}$alkyl or a ring which is: $C_{3-10}$cycloalkyl, $C_{6-10}$aryl, 5 membered heteroaromatic ring containing 1, 2, 3 or 4 heteroatoms independently selected from N, O and S, not more than one heteroatom of which is O or S, a 6 membered heteroaromatic ring containing one, two or three N atoms, or a 7-15 membered saturated, partially saturated or unsaturated heterocyclic ring containing one, two, three or four heteroatoms independently selected from N, O and S; any of which rings being optionally substituted by one, two, three or four groups independently selected from $R^{11}$; and each $R^{11}$ is independently hydroxy, oxo, cyano, halogen, $C_{1-6}$alkyl, $C_{2-10}$alkenyl, halo$C_{1-6}$alkyl, hydroxy$C_{1-6}$alkyl, carboxy, nitro, $OR^a$, $NR^aR^b$, $NR^aCOR^b$, $NR^aS(O)_rR^b$, $NR^aS(O)_rNR^aR^b$, $CO_2R^a$, $CONR^aR^b$, $S(O)_rR^a$, $S(O)_rNR^aR^b$ or a ring which is: $C_{3-10}$cycloalkyl, $C_{6-10}$aryl, $C_{6-10}$aryloxy, $C_{6-10}$aryl$C_{1-6}$alkoxy, azetidinyl, a 5 or 6 membered saturated or partially saturated heterocyclic ring containing one, two or three heteroatoms independently selected from N, O and S, a 5 membered heteroaromatic ring containing 1, 2, 3 or 4 heteroatoms independently selected from N, O and S, not more than one heteroatom of which is O or S or a 6 membered heteroaromatic ring containing one, two or three N atoms; any of which rings being optionally substituted by one, two or three groups independently selected from hydroxy, oxo, cyano, halogen, $C_{1-6}$alkyl, halo$C_{1-6}$alkyl, $C_{1-6}$alkoxy and halo$C_{1-6}$alkoxy.

In an embodiment w is 0.

In an embodiment x is 0. In another embodiment x is 1.

In an embodiment $R^4$ is $C_{1-6}$alkyl, for example methyl.

In another embodiment, x is 1 and $R^4$ is $C_{1-6}$alkyl, for example methyl.

In an embodiment y is 0.

In an embodiment z is 0.

In an embodiment each of w, y and z is 0 and x is 0 or 1.

In an embodiment each of w, x, y and z is 0. In another embodiment each of w, y and z is 0 and x is 1.

In an embodiment each of $R^3$, $R^4$, $R^5$ and $R^6$ is independently $C_{1-6}$alkyl, for example methyl.

In an embodiment $R^4$ is $C_{1-6}$alkyl or $C_{1-6}$alkoxy$C_{1-6}$alkyl.

Particular $R^4$ groups are methyl, ethyl or methoxymethyl.

In an embodiment A is $C_{3-6}$cycloalkyl or fluoro$C_{3-6}$cycloalkyl.

Particular A groups are cyclopropyl, fluorocyclopropyl and cyclobutyl.

In an embodiment A is cyclopropyl.

For the avoidance of doubt, -$LR^2$ is —$(X=O)_a(NR^7)_b(O)_c(CR^8R^9)_d(NR^7)_eR^2$. It will be apparent that when each of a, b, c, d and e is 0 then $R^2$ is attached directly to the core ring.

In an embodiment a is 1.

In an embodiment b is 1.

In an embodiment c is 0.

In an embodiment d is 0 or 1.

In an embodiment e is 0.

In an embodiment L is —$(X=O)(NR^7)_b(CR^8R^9)_d$—.

In an embodiment L is —$(X=O)(NR^7)(CR^8R^9)_d$—.

In an embodiment X is C. In another embodiment X is S=O.

In an embodiment L is —(C=O)(NR$^7$)—, —(C=O)(CR$^8$R$^9$)$_d$— or —(C=O)(NR$^7$)(CR$^8$R$^9$)—.

In another embodiment L is —(C=O)(NR$^7$)—. In another embodiment L is —(C=O)(CR$^8$R$^9$)$_d$—. In another embodiment L is —(C=O)(NR$^7$)(CR$^8$R$^9$)—.

In an embodiment R$^7$ is hydrogen or C$_{1-6}$alkyl. Particular R$^7$ groups are hydrogen and butyl, especially hydrogen.

In an embodiment each of R$^8$ and R$^9$ is independently hydrogen, C$_{1-6}$alkyl and C$_{1-6}$alkoxycarbonyl.

In an embodiment one of R$^8$ and R$^9$ is hydrogen or methyl and the other hydrogen, methyl or ethoxycarbonyl.

In an embodiment one of R$^8$ and R$^9$ is hydrogen or methyl and the other methyl or ethoxycarbonyl.

In an embodiment L is —(C=O)(NH)—. In another embodiment L is —(C=O).

In an embodiment m is 1. In another embodiment m is 2.
In an embodiment n is 1. In another embodiment n is 2.
In an embodiment each of m and n is 1.

In an embodiment R$^1$ is C$_{6-10}$aryl, optionally substituted by one, two or three groups independently selected from R$^{10}$. In another embodiment R$^1$ is an optionally substituted phenyl.

In an embodiment when R$^1$ is a ring it is unsubstituted or monosubstituted.

In another embodiment R$^1$ is C$_{6-10}$aryl; C$_{3-10}$cycloalkyl; oxetanyl; azetidinyl; a 5 or 6 membered saturated or partially saturated heterocyclic ring containing one, two or three heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing one, two or three N atoms; or a 7-15 membered unsaturated, partially saturated or saturated heterocyclic ring containing one, two, three or four heteroatoms independently selected from N, O and S; any of which rings being optionally substituted by one, two or three groups independently selected from R$^{10}$.

In an embodiment R$^{10}$ is cyano, halogen or OR$^a$.
In an embodiment R$^{10}$ is halogen or OR$^a$.
In an embodiment R$^a$ is C$_{1-6}$alkyl.

Particular R$^{10}$ groups are chlorine, fluorine and methoxy. A further particular R$^{10}$ group is cyano. A further R$^{10}$ group is bromine.

Particular R$^1$ groups are phenyl, chlorophenyl, fluorophenyl and methoxyphenyl. Further particular R$^1$ groups are difluorophenyl and cyanophenyl. A further particular R$^{10}$ group is dibromophenyl.

Specific R$^1$ groups are phenyl, 4-chlorophenyl, 4-fluorophenyl and 4-methoxyphenyl. Further specific R$^1$ groups are 2-methoxyphenyl, 3,4-difluorophenyl, 3-methoxyphenyl, 2,4-difluorophenyl, 4-cyanophenyl and 3-cyanophenyl. A further specific R$^{10}$ group is 3,5-dibromophenyl.

In an embodiment R$^2$ is C$_{1-10}$alkyl, C$_{1-6}$alkylmercaptoC$_{1-6}$alkyl or a ring which is: C$_{3-10}$cycloalkyl, C$_{6-10}$aryl, a 5 membered heteroaromatic ring containing 1, 2, 3 or 4 heteroatoms independently selected from N, O and S, not more than one heteroatom of which is O or S, a 6 membered heteroaromatic ring containing one, two or three N atoms, or a 8-10 membered saturated, partially saturated or unsaturated heterocyclic ring containing one, two, three or four heteroatoms independently selected from N, O and S; any of which rings being optionally substituted by one, two or three groups independently selected from R$^{11}$.

In an embodiment R$^2$ is C$_{3-10}$cycloalkyl, C$_{6-10}$aryl, a 5 membered heteroaromatic ring containing 1, 2, 3 or 4 heteroatoms independently selected from N, O and S, not more than one heteroatom of which is O or S, a 6 membered heteroaromatic ring containing one, two or three N atoms, or a 8-10 membered partially saturated or unsaturated heterocyclic ring containing one, two, three or four heteroatoms independently selected from N, O and S; any of which rings being optionally substituted by one, two or three groups independently selected from R$^{11}$.

In an embodiment R$^2$ is C$_{1-8}$alkyl, C$_{1-6}$alkylmercaptoC$_{1-6}$alkyl, C$_{2-6}$alkenyl or a ring which is: phenyl, cyclohexyl, pyrazolyl, pyridinyl, benzodioxolyl, isoxazolyl, pyrrolidinyl, cyclopropyl, piperidinyl, tetrahydrothiopyranyl, oxazolyl, tetrahydronaphthalenyl, tetrahydroquinolinyl or tetrahydropyranyl; any of which rings being optionally substituted by one, two or three groups independently selected from R$^{11}$. Further optionally substituted rings include cyclopentyl and bicycloheptyl.

In an embodiment R$^2$ is a 5 membered heteroaromatic ring containing 1, 2, 3 or 4 heteroatoms independently selected from N, O and S, not more than one heteroatom of which is O or S, optionally substituted by one, two or three groups independently selected from halogen, C$_{1-6}$alkyl, haloC$_{1-6}$alkyl or C$_{6-10}$aryl optionally substituted by one, two or three groups independently selected from halogen, C$_{1-6}$alkyl or haloC$_{1-6}$alkyl.

In an embodiment R$^2$ is C$_{1-8}$alkyl, C$_{1-6}$alkylmercaptoC$_{1-6}$alkyl or a ring which is: phenyl, cyclohexyl, pyrazolyl, pyridinyl or benzodioxolyl; any of which rings being optionally substituted by one, two or three groups independently selected from R$^{11}$.

In an embodiment R$^2$ is phenyl, cyclohexyl, pyrazolyl, pyridinyl or benzodioxolyl; optionally substituted by one, two or three groups independently selected from R$^{11}$.

In an embodiment R$^2$ is phenyl, optionally substituted by one, two or three groups independently selected from R$^{11}$.

In an embodiment, when R$^2$ is a ring it is unsubstituted or optionally substituted by one, two or three groups independently selected from R$^{11}$.

In an embodiment R$^{11}$ is oxo, cyano, halogen, C$_{1-6}$alkyl, C$_{2-10}$alkenyl, haloC$_{1-6}$alkyl, C$_{1-6}$alkylcarbonyl, OR$^a$, NR$^a$R$^b$, CO$_2$R$^a$, S(O)$_r$R$^a$, NR$^a$S(O)$_r$R$^b$ or a ring which is: C$_{3-10}$cycloalkyl, C$_{6-10}$aryl, C$_{6-10}$arylC$_{1-6}$alkoxy, C$_{6-10}$arylC$_{1-6}$alkyl or a 5 membered heteroaromatic ring containing 1, 2, 3 or 4 heteroatoms independently selected from N, O and S, not more than one heteroatom of which is O or S; any of which rings being optionally substituted by one, two or three groups independently selected from hydroxy, oxo, cyano, halogen, C$_{1-6}$alkyl, haloC$_{1-6}$alkyl, C$_{1-6}$alkoxy and haloC$_{1-6}$alkoxy.

In an embodiment R$^{11}$ is cyano, halogen, C$_{1-6}$alkyl, C$_{2-10}$alkenyl, haloC$_{1-6}$alkyl, OR$^a$, NR$^a$R$^b$, CO$_2$R$^a$, S(O)$_r$R$^a$ or a ring which is: C$_{6-10}$aryl, C$_{6-10}$arylC$_{1-6}$alkoxy, or a 5 membered heteroaromatic ring containing 1, 2, 3 or 4 heteroatoms independently selected from N, O and S, not more than one heteroatom of which is O or S; any of which rings being optionally substituted by one, two or three groups independently selected from hydroxy, oxo, cyano, halogen, C$_{1-6}$alkyl, haloC$_{1-6}$alkyl, C$_{1-6}$alkoxy and haloC$_{1-6}$alkoxy.

In an embodiment each of R$^a$ and R$^b$ is independently hydrogen, C$_{1-6}$alkyl or C$_{6-10}$aryl optionally substituted by one, two or three C$_{1-6}$alkyl groups.

Particular R$^a$ groups are hydrogen, methyl and phenyl.
Particular R$^b$ groups are hydrogen, methyl, phenyl and methylphenyl, for example 4-methylphenyl In an embodiment each R$^a$ is independently C$_{1-6}$alkyl or haloC$_{1-6}$alkyl, for example methyl or trifluoromethyl.

In an embodiment r is 2.
In an embodiment R$^b$ is C$_{1-6}$alkyl, for example methyl.
In an embodiment each of R$^a$ and R$^b$ is independently hydrogen or C$_{1-6}$alkyl.

In an embodiment $R^{11}$ is cyano, oxo, halogen, $C_{1-6}$alkyl, $C_{1-6}$alkylcarbonyl, $C_{2-6}$alkenyl, $C_{2-6}$alkynyl, halo$C_{1-6}$alkyl, $C_{1-6}$alkoxy, halo$C_{1-6}$alkoxy, $C_{1-6}$alkoxycarbonyl, amino, $C_{1-6}$alkylamino, di($C_{1-6}$alkyl)amino, [di($C_{1-6}$alkyl)amino] carbonyl, $C_{1-6}$alkylsulfonyl or a ring which is: cyclopropyl, phenyl, benzyloxy, thienyl, oxazolyl, pyridinyl or pyrazolyl; any of which rings being optionally substituted by one, two or three groups independently selected from halogen, cyano, $C_{1-6}$alkyl, $C_{1-6}$alkylsulfonyl, halo$C_{1-6}$alkyl and $C_{1-6}$alkoxy. Further $R^{11}$ groups include [($C_{1-6}$alkylphenyl)sulfonyl] amino, phenylsulfonyl and optionally substituted rings selected from cyclohexyl and benzyl.

In an embodiment $R^{11}$ is cyano, halogen, $C_{1-6}$alkyl, $C_{2-6}$alkenyl, halo$C_{1-6}$alkyl, $C_{1-6}$alkoxy, halo$C_{1-6}$alkoxy, $C_{1-6}$alkoxycarbonyl, amino, $C_{1-6}$alkylamino, di($C_{1-6}$alkyl) amino, $C_{1-6}$alkylsulfonyl or a ring which is: phenyl, benzyloxy, thienyl or oxazolyl; any of which rings being optionally substituted by one, two or three groups independently selected from halogen, $C_{1-6}$alkyl, halo$C_{1-6}$alkyl and $C_{1-6}$alkoxy.

In an embodiment, when $R^{11}$ is a ring it is unsubstituted or monosubstituted.

In an embodiment the optional substituents on the $R^{11}$ ring are independently selected from halogen, $C_{1-6}$alkyl, halo$C_{1-6}$alkyl and $C_{1-6}$alkoxy. Further optional substituents on the $R^{11}$ ring are cyano and $C_{1-6}$alkylsulfonyl.

Particular optional substituents on the $R^{11}$ ring are independently selected from chloro, trifluoromethyl and methoxy. Further particular optional substituents on the $R^{11}$ ring are methylsulfonyl, fluoro, cyano and methyl.

Particular $R^{11}$ groups are phenyl, chloro, chlorophenyl, propenyl, benzyloxy, dimethylamino, trifluoromethyl, methoxy, propyl, fluoro, thienyl, methylsulfonyl, cyano, methyl, oxazolyl, trifluoromethoxy, methoxycarbonyl, (trifluoromethyl)phenyl and methoxyphenyl. Further particular $R^{11}$ groups are cyclopropyl, acetyl, oxo, (methylsulfonyl)phenyl, (dimethylamino)carbonyl, ethyl, fluorophenyl, dichlorophenyl, pyridinyl, cyanophenyl, methylpyrazolyl and ethynyl.

Further particular $R^{11}$ groups are butyl, cyclohexyl, propanyl, [(methylphenyl)sulfonyl]amino, benzyl and phenylsulfonyl.

Specific $R^{11}$ groups are phenyl, chloro, 3-chlorophenyl, isopropenyl, benzyloxy, dimethylamino, trifluoromethyl, methoxy, isopropyl, fluoro, 3-thienyl, methylsulfonyl, cyano, methyl, 1,3-oxazol-5-yl, trifluoromethoxy, methoxycarbonyl, 3-(trifluoromethyl)phenyl, 2-chlorophenyl, 4-chlorophenyl, 2-methoxyphenyl, 3-methoxyphenyl and 4-methoxyphenyl. Further specific $R^{11}$ groups are cyclopropyl, acetyl, oxo, 3-(methylsulfonyl)phenyl, (dimethylamino)carbonyl, ethyl, 3-fluorophenyl, 3,5-dichlorophenyl, 4-fluorophenyl, pyridin-3-yl, 3-cyanophenyl, 1-methyl-1H-pyrazol-4-yl and ethynyl.

Further specific $R^{11}$ groups are tertbutyl, cyclohexyl, propan-2-yl, [(4-methylphenyl)sulfonyl]amino, benzyl and phenylsulfonyl.

Particular $R^2$ groups are biphenyl, dichlorophenyl, cyclohexyl, phenylpyrazolyl, (chlorophenyl)pyridinyl, isopropenylphenyl, butyl, benzodioxolyl, methylmercaptoethyl, (benzyloxy)phenyl, hexyl, (dimethylamino)phenyl, (trifluoromethyl)phenyl, methoxyphenyl, isopropylphenyl, dichlorofluorophenyl, phenyl, chlorofluorophenyl, chloropyridinyl, thienylpyridinyl, thienylphenyl, chloro(methylsulfonyl)phenyl, (chloro)(cyano)(methyl)phenyl, dichlorocyanophenyl, (chloro)(methyl)phenyl, oxazolylphenyl, dichloro(trifluoromethoxy)phenyl, dichloro(trifluoromethyl) phenyl, (chloro)(methoxycarbonyl)phenyl, [(trifluoromethyl)phenyl]pyridinyl, (methoxycarbonyl)(methyl)phenyl, dichloropyridinyl, (methoxyphenyl)pyridinyl and dichloro (methylsulfonyl)phenyl. Further particular $R^2$ groups are phenylisoxazolyl, (chloro)(cyclopropyl)pyridinyl, (acetyl)(phenyl)pyrrolidinyl, methylcyclopropyl, (acetyl)(phenyl)piperidinyl, dioxidotetrahydrothiopyranyl, [(methylsulfonyl) phenyl]pyridinyl, (chlorophenyl)pyrazolyl, phenyloxazolyl, phenylcyclohexyl, tetrahydronaphthalenyl, dichloro[(dimethylamino)carbonyl]phenyl, (chloro)dimethylphenyl, (chloro)(methoxy)pyridinyl, (chloro)(methyl)pyridinyl, (chloro)(ethyl)pyridinyl, (fluorophenyl)pyrazolyl, (dichlorophenyl)pyrazolyl, oxotetrahydroquinolinyl, (fluoro)(oxo) tetrahydroquinolinyl, dimethylpyridinyl, methylcyclohexyl, (fluorophenyl)pyridinyl, bipyridinyl, (cyanophenyl)pyridinyl, (methylpyrazolyl)pyridinyl, phenylpyridinyl, (cyclopropyl)(methyl)pyridinyl, ethyl, propyl, ethenyl, (methylsulfonyl)(phenyl)piperidinyl, (methyl)(phenyl)piperidinyl, methyltetrahydropyranyl and ethynylcyclohexyl. Further particular $R^2$ groups are (fluorophenyl)(methyl)pyrazolyl, (acetyl)(methyl)piperidinyl, cyclopentyl, dimethylcyclohexyl, phenylcyclohexyl, butylcyclohexyl, trimethylbicyclo [2.2.1]heptyl, bi(cyclohexyl), tetrahydropyranyl, methyl (propanyl)cyclohexyl, {[(methylphenyl)sulfonyl] amino}cyclohexyl, difluorocyclohexyl, phenylpiperidinyl, benzylmethylpiperidinyl, fluoropiperidinyl, (methylsulfonyl)piperidinyl, (acetyl)(fluoro)piperidinyl, (fluoro)(methylsulfonyl)piperidinyl, (fluoro)(phenylsulfonyl)piperidinyl and acetylpiperidinyl.

Specific $R^2$ groups are biphenyl-2-yl, 2,3-dichlorophenyl, cyclohexyl, 1-phenyl-1H-pyrazol-5-yl, 2-(3-chlorophenyl) pyridin-3-yl, 3-isopropenylphenyl, 2,6-dichlorophenyl, butyl, 1,3-benzodioxol-5-yl, methylmercaptoethyl, 4-(benzyloxy)phenyl, biphenyl-4-yl, hexyl, 4-(dimethylamino)phenyl, 2-(trifluoromethyl)phenyl, 2-methoxyphenyl, 2-isopropylphenyl, 2,6-dichloro-4-fluorophenyl, phenyl, 2-chloro-4-fluorophenyl, 2-chloropyridin-3-yl, 2-(3-thienyl)pyridin-3-yl, 2,3-dichloro-4-fluorophenyl, 2-(3-thienyl)phenyl, 2-chloro-4-(methylsulfonyl)phenyl, 2-chloro-4-cyano-6-methylphenyl, 2,6-dichloro-4-cyanophenyl, 3-chloro-2-methylphenyl, 2-chloro-6-methylphenyl, 3,5-dichlorophenyl, 2-(1,3-oxazol-5-yl)phenyl, 2,6-dichloro-4-(trifluoromethoxy)phenyl, 2,6-dichloro-4-(trifluoromethyl)phenyl, 2-chloro-3-methoxycarbonylphenyl, 2-[3-(trifluoromethyl) phenyl]pyridin-3-yl, 3-methoxycarbonyl-2-methylphenyl, 3,5-dichloropyridin-4-yl, 2-(2-chlorophenyl)pyridin-3-yl, 2-(4-chlorophenyl)pyridin-3-yl, 2-(2-methoxyphenyl)pyridin-3-yl, 2-(3-methoxyphenyl)pyridin-3-yl, 2-(4-methoxyphenyl)pyridin-3-yl and 2,6-dichloro-4-(methylsulfonyl) phenyl. Further specific $R^2$ groups are 4-phenylisoxazol-5-yl, 4-chloro-2-cyclopropylpyridin-3-yl, (E)-1-acetyl-4-phenylpyrrolidin-3-yl, 1-methylcyclopropyl, tert-butyl, 1-acetyl-3-phenylpiperidin-4-yl, 1,1-dioxidotetrahydro-2H-thiopyran-4-yl, 2-[3-(methylsulfonyl)phenyl]pyridin-3-yl, 1-(3-chlorophenyl)-1H-pyrazol-5-yl, 5-phenyl-1,3-oxazol-2-yl, (1R,2S)-2-phenylcyclohexyl, 1,2,3,4-tetrahydronaphthalen-1-yl, 2,6-dichloro-4-[(dimethylamino)carbonyl]phenyl, 2-chloro-4,6-dimethylphenyl, 4-chloro-2-methoxypyridin-3-yl, 4-chloro-2-methylpyridin-3-yl, 4-chloro-2-ethylpyridin-3-yl, 1-(3-fluorophenyl)-1H-pyrazol-5-yl, 1-(3,5-dichlorophenyl)-1H-pyrazol-5-yl, 2-oxo-1,2,3,4-tetrahydroquinolin-4-yl, 6-fluoro-2-oxo-1,2,3,4-tetrahydroquinolin-4-yl, 2,4-dimethylpyridin-3-yl, 1-methylcyclohexyl, 2-(4-fluorophenyl)pyridin-3-yl, 2,3'-bipyridin-3-yl, 2-(3-cyanophenyl)pyridin-3-yl, 2-(1-methyl-1H-pyrazol-4-yl)pyridin-3-yl, 2-phenylpyridin-3-yl, 2-cyclopropyl-4-methylpyridin-3-yl, 3-phenylpyridin-4-yl, ethyl, propyl, ethenyl, 1-(methylsulfonyl)-3-phenylpiperidin-4-yl, 1-methyl-3-phenylpiperidin-4-yl, 4-methyltetrahydro-2H-pyran-4-yl, 1-ethynylcyclohexyl, trans-1-acetyl-3-phenylpiperidin-4-yl, cis-1-acetyl-3-phenylpiperidin-4-yl, trans-1-(methylsulfonyl)-3-phenylpiperidin-4-yl and cis-1-(methylsulfonyl)-3-phenylpiperidin-4-yl. Further specific $R^2$ groups are 4-(4-fluorophenyl)-1-methyl-1H-pyrazol-5-yl, 3-(3-fluorophenyl)-1-methyl-1H-pyrazol-4-yl, 1-acetyl-4-methylpiperidin-4-yl, cyclopentyl, 4,4-dimethylcyclohexyl, 1-phenylcyclohexyl, 2-methylcyclohexyl, 3-methylcyclohexyl, trans-4-methylcyclohexyl, trans-2-phenylcyclohexyl, 4-tert-butylcyclohexyl, 4-phenylcyclohexyl, (1S,2R)-1,7,7-trimethylbicyclo[2.2.1]hept-2-yl, (1R,2S)-1,7,7-trimethylbicyclo[2.2.1]hept-2-yl, cis-bicyclohex-2-yl, trans-bicyclohex-2-yl, tetrahydro-2H-pyran-4-yl, (1R,2S,5R)-5-methyl-2-(propan-2-yl)cyclohexyl, (1S,2S)-2-{[(4-methylphenyl)sulfonyl]amino}cyclohexyl, (1R,2R)-2-{[(4-methylphenyl)sulfonyl]amino}cyclohexyl, 4,4-difluoro-cyclohexyl, 1-phenylpiperidinyl, cis-3-benzyl-1-methylpiperidin-4-yl, 3-fluoropiperidin-4-yl, 1-(methylsulfonyl)piperidin-4-yl, (trans)-1-acetyl-3-fluoropiperidin-4-yl, (trans)-3-fluoro-1-methylsulfonylpiperidin-4-yl, (trans)-3-fluoro-1-(phenylsulfonyl)piperidin-4-yl, (cis)-3-fluoro-1-(methylsulfonyl)piperidin-4-yl, (cis)-1-acetyl-3-fluoropiperidin-4-yl and 1-acetylpiperidin-4-yl.

In an embodiment:

each of w, x, y and z is 0;

L is —(C=O)(NR$^7$);

m is 1 or 2;

n is 1 or 2; and $R^1$ is $C_{6-10}$aryl, optionally substituted by one, two or three groups independently selected from $R^{10}$.

In another embodiment:

each of w, x, y and z is 0;

L is —(C=O)(NR$^7$);

m is 1 or 2;

n is 1 or 2; and $R^2$ is $C_{3-10}$cycloalkyl, $C_{6-10}$aryl, a 5 membered heteroaromatic ring containing 1, 2, 3 or 4 heteroatoms independently selected from N, O and S, not more than one heteroatom of which is O or S, a 6 membered heteroaromatic ring containing one, two or three N atoms, or a 8-10 membered partially saturated or unsaturated heterocyclic ring containing one, two, three or four heteroatoms independently selected from N, O and S; any of which rings being optionally substituted by one, two or three groups independently selected from $R^{11}$.

In an embodiment:

each of w, y and z is 0 and x is 1;

$R^4$ is $C_{1-6}$alkyl;

d is 0;

$R^7$ is hydrogen;

$R^2$ is a 5 membered heteroaromatic ring containing 1, 2, 3 or 4 heteroatoms independently selected from N, O and S, not more than one heteroatom of which is O or S, optionally substituted by one, two or three groups independently selected from halogen, $C_{1-6}$alkyl, halo$C_{1-6}$alkyl or $C_{6-10}$aryl optionally substituted by one, two or three groups independently selected from halogen, $C_{1-6}$alkyl or halo$C_{1-6}$alkyl.

In an embodiment:

each of w, y and z is 0 and x is 1;

each of m and n is 1;

$R^1$ is $C_{6-10}$aryl, optionally substituted by one, two or three groups independently selected from $R^{10}$.

The present invention also provides a compound of formula II:

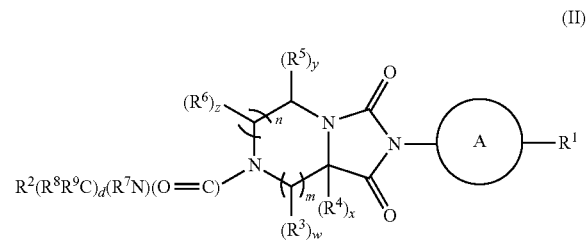

(II)

wherein m, n, d, w, x, y, z, A, $R^1$, $R^2$, $R^3$, $R^4$, $R^5$, $R^6$, $R^7$, $R^8$ and $R^9$ are as defined above;

or a pharmaceutically acceptable salt, stereoisomer or tautomer thereof.

The present invention also provides a compound of formula III:

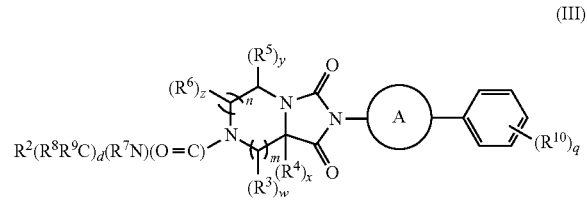

(III)

wherein:

q is 0, 1, 2 or 3;

m, n, d, w, x, y, z, A, $R^1$, $R^2$, $R^3$, $R^4$, $R^5$, $R^6$, $R^7$, $R^8$, $R^9$ and $R^{10}$ are as defined above;

or a pharmaceutically acceptable salt, stereoisomer or tautomer thereof.

The present invention also provides a compound of formula IV:

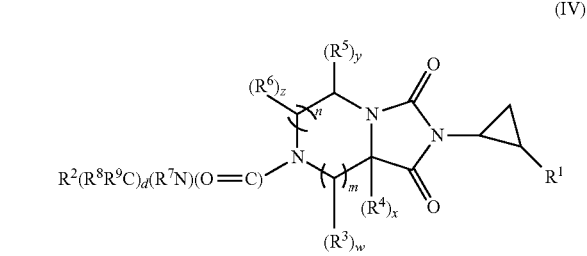

(IV)

wherein:

m, n, d, w, x, y, z, $R^1$, $R^2$, $R^3$, $R^4$, $R^5$, $R^6$, $R^7$, $R^8$ and $R^9$ are as defined above;

or a pharmaceutically acceptable salt, stereoisomer or tautomer thereof.

The present invention also provides a compound of formula V:

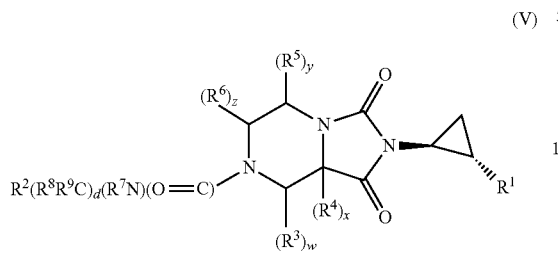

(V)

wherein:
d, w, x, y, z, $R^1$, $R^2$, $R^3$, $R^4$, $R^5$, $R^6$, $R^7$, $R^8$ and $R^9$ are as defined above;
or a pharmaceutically acceptable salt, stereoisomer or tautomer thereof.

The present invention also provides a compound of formula VI:

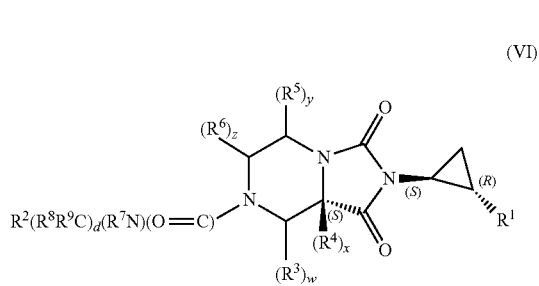

(VI)

wherein:
d, w, x, y, z, $R^1$, $R^2$, $R^3$, $R^4$, $R^5$, $R^6$, $R^7$, $R^8$ and $R^9$ are as defined above;
or a pharmaceutically acceptable salt, stereoisomer or tautomer thereof.

The present invention also provides a compound of formula VII:

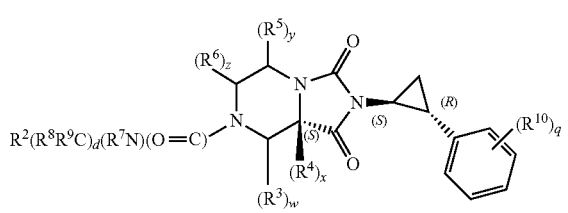

(VII)

wherein:
d, q, w, x, y, z, $R^2$, $R^3$, $R^4$, $R^5$, $R^6$, $R^7$, $R^8$, $R^9$ and $R^{10}$ are as defined above;
or a pharmaceutically acceptable salt, stereoisomer or tautomer thereof.

The present invention also provides a compound of formula VIII:

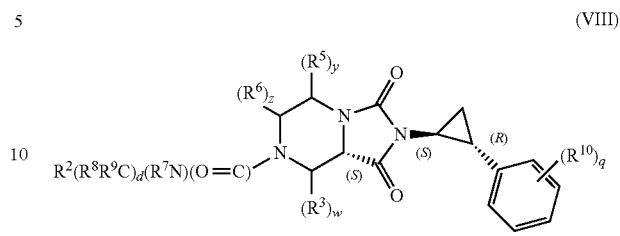

(VIII)

wherein:
d, q, w, y, z, $R^2$, $R^3$, $R^5$, $R^6$, $R^7$, $R^8$, $R^9$ and $R^{10}$ are as defined above;
or a pharmaceutically acceptable salt, stereoisomer or tautomer thereof.

The present invention also provides a compound of formula IX:

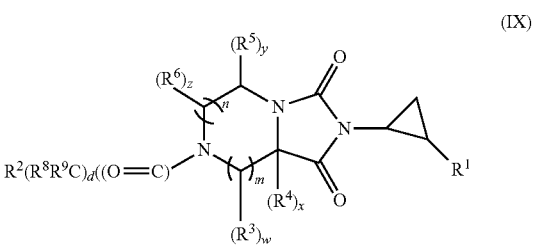

(IX)

wherein:
m, n, d, w, x, y, z, $R^1$, $R^2$, $R^3$, $R^4$, $R^5$, $R^6$, $R^8$ and $R^9$ are as defined above;
or a pharmaceutically acceptable salt, stereoisomer or tautomer thereof.

The preferred identities with reference to compounds of formulae II, III, IV, V, VI, VII, VIII and IX are as defined previously for formula I mutatis mutandis.

In an embodiment q is 0 or 1.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

The compounds may exist in different isomeric forms, all of which are encompassed by the present invention.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

The compounds may exist in a number of different polymorphic forms.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched and straight-chain saturated aliphatic hydrocarbon groups having the specified number of carbon atoms. For example, "$C_{1-6}$alkyl" is defined to include groups having 1, 2, 3, 4, 5 or 6 carbons in a linear or branched arrangement. For example, "$C_{1-6}$alkyl" specifically includes methyl, ethyl, n-propyl, i-propyl, n-butyl, t-butyl, i-butyl, pentyl and hexyl and so on. Preferred alkyl groups are methyl and ethyl. The term "cycloalkyl" means a monocyclic, bicyclic or polycyclic saturated aliphatic hydrocarbon group having the specified number of carbon atoms. For example, "$C_{3-7}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

As used herein, the term "$C_{2-10}$alkenyl" refers to a non-aromatic hydrocarbon radical, straight or branched, containing from 2 to 10, including 2 to 6, carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. Preferred alkenyl groups include ethenyl and propenyl.

As used herein, the term "$C_{2-10}$alkynyl" refers to a hydrocarbon radical straight or branched, containing from containing from 2 to 10, including 2 to 6 carbon atoms and at least one carbon to carbon triple bond. Up to three carbon-carbon triple bonds may be present. Alkynyl groups include ethynyl, propynyl, butynyl, 3-methylbutynyl and so on. Preferred alkynyl groups include ethynyl and propynyl.

"Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy, t-butoxy, cyclopropyloxy, cyclobutyloxy and cyclopentyloxy. The preferred alkoxy groups are methoxy and ethoxy. The term '$C_{6-10}$aryloxy' can be construed analogously, and an example of this group is phenoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

As used herein, the term "hydroxy$C_{1-6}$alkyl" means a $C_{1-6}$alkyl group in which one or more (in particular, 1 to 3) hydrogen atoms have been replaced by hydroxy groups. Preferred are $CH_2OH$, $CH_2CHOH$ and $CHOHCH_3$. The term 'hydroxy$C_{2-10}$alkenyl' and 'hydroxy$C_{2-10}$alkynyl' can be construed analogously. An example of 'hydroxy$C_{2-10}$alkynyl' is (hydroxy)(methyl)butynyl.

As used herein, the term "$C_{1-6}$alkylcarbonyl" or "$C_{1-6}$alkoxycarbonyl" denotes a $C_{1-6}$alkyl or $C_{1-6}$alkoxy radical, respectively, attached via a carbonyl (C=O) radical. Suitable examples of $C_{1-6}$alkylcarbonyl groups include methylcarbonyl, ethylcarbonyl, propylcarbonyl, isopropylcarbonyl and tert-butylcarbonyl. Examples of $C_{1-6}$alkoxycarbonyl include methoxycarbonyl, ethoxycarbonyl, propoxycarbonyl, isopropoxycarbonyl and tert-butoxycarbonyl. The term '$C_{6-10}$arylcarbonyl' can be construed analogously, and an example of this group is benzoyl.

As used herein, the term "$C_{1-6}$alkylmercapto$C_{1-6}$alkyl" represents an alkyl group of indicated number linked via an S atom. Examples of suitable alkylmercaptoalkyl groups include $CH_3SCH_2$, $CH_3SCH_2CH_2$ and $CH_3SCH_2CH_2CH_2$ and $CH_3CH_2SCH_2$.

The rings present in the compounds of this invention may be monocyclic or multicyclic, particularly bicyclic. The multicyclic rings may be fused, bridged or spiro linked.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

7-15 membered heterocycles include 7, 8, 9, 10, 11, 12, 13, 14 and 15 membered heterocycles. Similarly, 7-10 membered rings include 7, 8, 9 and 10 membered rings.

Heteroaryl denotes an unsaturated heterocycle ring.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolinyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, imidazolidinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydroisoquinolinyl, dihydrotetrazolyl, dihydrothiadiazolyl, dihydrothiazolyl, dihydrothienyl, dihydrotriazolyl, dihydroazetidinyl, dihydroisochromenyl, dihydrochromenyl, dihydroimidazolonyl, dihydrotriazolonyl, dihydrobenzodioxinyl, dihydrothiazolopyrimidinyl, dihydroimidazopyrazinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazinyl, azoniabicycloheptanyl, azoniabicyclooctanyl, phthalazinyl, naphthyridinyl, pteridinyl, dihydroquinazolinyl, dihydrophthalazinyl, benzisoxazolyl, tetrahydronaphthyridinyl, dibenzo[b,d]furanyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, diazepanyl, azoniabicyclohexanyl, azoniabicycloheptanyl, azepanyl, octahydropyridopyrazinyl, diazabicycloheptanyl diazoniaspirodecanyl, diazoniaspirononanyl, octahydropyrrolopyrrolyl and tetrahydrotriazolopyrazinyl and N-oxides thereof. Attachment of a heterocyclyl substituent can occur via a carbon atom or via a heteroatom.

Preferred 5 or 6 membered saturated or partially saturated heterocycles are pyrrolidinyl, piperidinyl, piperazinyl, morpholinyl, tetrahydrofuran, thiomorpholinyl, azoniabicyclohexanyl, azoniabicycloheptanyl and tetrahydropyranyl. A further ring is tetrahydrothiopyranyl.

Preferred 5 membered heteroaromatic rings are thienyl, thiazolyl, pyrazolyl, isoxazolyl, isothiazolyl, imidazolyl, thiadiazolyl, oxazolyl, oxadiazolyl, triazolyl, tetrazolyl, furyl and pyrrolyl.

Preferred 6 membered heteroaromatic rings are pyridinyl, pyrimidinyl, pyridazinyl and pyrazinyl.

Preferred 7-15 membered saturated, partially saturated or unsaturated heterocyclic rings are diazepanyl, azepanyl, tetrahydroquinolinyl, quinolinyl, indolyl, imidazopyridinyl, benzothiazolyl, quinoxalinyl, benzothiadiazolyl, benzoxazolyl, dihydrobenzodioxinyl, benzotriazolyl, benzodioxolyl, dihydroisoindolyl, dihydroindolyl, tetrahydroisoquinolinyl, isoquinolinyl, benzoisothiazolyl, dihydroimidazopyrazinyl, benzothienyl, benzoxadiazolyl, thiazolotriazolyl, dihydrothiazolopyrimidinyl, dihydrobenzoxazinyl, dihydrobenzofuranyl, benzimidazolyl, benzofuranyl, dihydrobenzoxazolyl, dihydroquinazolinyl, dihydrophthalazinyl, indazolyl, benzisoxazolyl, tetrahydronaphthyridinyl, triazolopyrimidinyl, dibenzo[b,d]furanyl, naphthyridinyl, dihydroquinolinyl, dihydroisochromenyl, dihydrochromenyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, quinazolinyl, indolizinyl, octahydropyridopyrazinyl, diazabicycloheptanyl, diazoniaspirodecanyl, diazoniaspirononanyl, octahydropyrrolopyrrolyl and tetrahydrotriazolopyrazinyl.

As used herein, the term "halogen" refers to fluorine, chlorine, bromine and iodine, of which fluorine and chlorine are preferred.

Particular compounds within the scope of the present invention are the specific compounds named in the representative Examples, and pharmaceutically acceptable salts, free bases, stereoisomers and tautomers thereof.

Included in the instant invention is the free base of compounds of Formula I, as well as the pharmaceutically acceptable salts and stereoisomers thereof. The compounds of the present invention can be protonated at the N atom(s) of an amine and/or N containing heterocycle moiety to form a salt. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents.

Thus, pharmaceutically acceptable salts of the compounds of this invention include the conventional non-toxic salts of the compounds of this invention as formed by reacting a basic instant compound with an inorganic, organic acid or polymeric acid. For example, conventional non-toxic salts include those derived from inorganic acids such as hydrochloric, hydrobromic, hydroiodic, sulfuric, sulfurous, sulfamic, phosphoric, phosphorous, nitric and the like, as well as salts prepared from organic acids such as maleic, pamoic, hydroxymaleic, glutamic, salicylic, toluenesulfonic, methanesulfonic, ethane disulfonic, oxalic, aspartic, ethanesulfonic, ethane, disulfonic, trifluoroacetic and the like. Examples of suitable polymeric salts include those derived from the polymeric acids such as tannic acid, carboxymethyl cellulose. Preferably, a pharmaceutically acceptable salt of this invention contains 1 equivalent of a compound of formula (I) and 1, 2 or 3 equivalent of an inorganic or organic acid.

More particularly, pharmaceutically acceptable salts of this invention are the trifluoroacetate or the chloride salts. In an embodiment the salt is trifluoroacetate. In another embodiment the salt is chloride.

The preparation of the pharmaceutically acceptable salts described above and other typical pharmaceutically acceptable salts is more fully described by Berg et al (1977) *J. Pharm. Sci., 'Pharmaceutical Salts',* 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of this invention may be administered to mammals, preferably humans, either alone or in combination with pharmaceutically acceptable carriers, excipients, diluents, adjuvants, fillers, buffers, stabilisers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly).

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

The present invention provides methods of inhibiting activation of the hedgehog signaling pathway, e.g., to inhibit aberrant growth states resulting from phenotypes such as Ptch loss-of-function, hedgehog gain of-function, smoothened gain-of-function or Gli gain-of-function, comprising contacting the cell with a compound of Formula I, in a sufficient amount to agonize a normal Ptc activity, antagonize a normal hedgehog activity, antagonize smoothened activity, or antagonize Gli activity e.g., to reverse or control the aberrant growth state.

The present invention further provides methods for treating, ameliorating one or more of the symptoms of, and reducing the severity of hyperproliferative disorders, i.e. cancer, as well as other hedgehog pathway mediated disorders or conditions.

Many tumors and proliferative conditions have been shown to depend on the hedgehog pathway. The growth of such cells and survival can be affected by treatment with the compounds of the present invention. For example, small molecule inhibition of the hedgehog pathway has been shown to inhibit the growth of basal cell carcinoma (Williams et al. *PNAS* 100: 4616-21 (2003)), medulloblastoma (Berman et al. *Science* 297:1559-61 (2002)), pancreatic cancer, gastrointestinal cancers and esophageal cancer (Berman et al. *Nature* 425:846-51 (2003) and WO 05/013800), lung cancer (Watkins et al. *Nature* 422:313-7 (2003)), and prostate cancer (Karhadkar et al. *Nature* 431: 707-12 (2004)).

In addition, it has been shown that many cancer types have uncontrolled activation of the hedgehog pathway, for example, breast cancer (Kubo et al. *Cancer Research* 64:6071-4 (2004)), heptacellular cancer (Patil et al. (2005) 96th Annual AACR conference, abstract #2942 and Sicklick et al. (2005) ASCO annual meeting, abstract #9610), hematological malignancies (Watkins and Matsui, unpublished results), basal carcinoma (Bale et al. *Human Molec. Genet.* B:757-762 (2001), Xie et al. *Nature* 391: 90-92 (1998)), medulloblastoma (Pietsch et al. *Cancer Res.* 57: 2085-88 (1997)), and gastric cancer (Ma et al. *Carcinogenesis May* 19, (2005) (EPub)).

Expression of a dysfunctional mutated patched gene has been reported in sporadic and familial BCCs. Patched gene mutations or deletions have also been found in sporadic medulloblastoma, meningiomas, breast carcinoma, esophageal squamous cell carcinoma and bladder tumors (Oncogene (1998) 17, 1167-1172).

The compounds of the present invention can be used for treating or preventing conditions which can be ameliorated by Smo antagonism. The compounds of the invention are also useful for the manufacture of a medicament for treating or preventing the diseases described herein.

The present invention provides the use of a compound of formula I for the manufacture of a medicament for treating or preventing conditions which can be ameliorated by Smo antagonism.

The present invention also provides a method for the treatment or prevention of conditions which can be ameliorated by Smo antagonism, which method comprises administration to a patient in need thereof of an effective amount of a compound of formula I or a composition comprising a compound of formula I.

The compounds, compositions and methods provided herein are particularly deemed useful for the treatment of cancer. Cancers that may be treated by the compounds, compositions and methods of the invention include, but are not limited to: Cardiac: sarcoma (angio sarcoma, fibrosarcoma, rhabdomyo sarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyo sarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In an embodiment the compounds of this invention can be used for treating or preventing cancers selected from basal cell carcinoma, medulloblastoma, prostate, pancreatic, breast, colon, small cell lung cancers, sarcoma, lymphomas, leukemia, gastrointestinal cancer, multiple myeloma, glioma and heptacellular. Further cancers that can be treated or prevented by the compounds of the present invention include sporadic and familial basal cell carcinomas, sporadic medulloblastoma, meningiomas, breast carcinoma, esophageal squamous cell carcinoma and bladder cancer.

The present invention also provides the use of a compound of formula I, or a pharmaceutically acceptable salt or solvate thereof for the manufacture of a medicament for the treatment or prevention of cancer.

The present invention also provides a method for the treatment or prevention of cancer, which method comprises administration to a patient in need thereof of an effective amount of a compound of formula I or a composition comprising a compound of formula I.

Inhibition of the hedgehog pathway has been shown to ameliorate the symptoms of psoriasis (Tas, et al., *Dermatology* 20q:126-131 (2004) and US 2004/0072913).

The present invention provides the use of a compound of formula I for the manufacture of a medicament for the treatment or prevention of psoriasis.

The present invention also provides a method for the treatment or prevention of psoriasis, which method comprises administration to a patient in need thereof of an effective amount of a compound of formula I or a composition comprising a compound of formula I Hedgehog activation has been shown to stimulate angiogenesis (Pola et al. *Nature Medicine* 7(6):706-711 (2001) and Nagase et al. *Genes to Cells* 10(6):595-604 (2005)) and thus compounds which act as hedgehog antagonists may be useful as angiogenesis antagonists.

The present invention provides the use of a compound of formula I for the manufacture of a medicament for the treatment or prevention of angiogenesis.

The present invention also provides a method for the treatment or prevention of angiogenesis, which method comprises administration to a patient in need thereof of an effective amount of a compound of formula I or a composition comprising a compound of formula I Diseases caused by, supported by or associated with angiogenesis which can be treated or prevented by the compounds of formula I include cancer, ocular neovascular disease, age-related macular degeneration, diabetic retinopathy, retinopathy of prematurity, corneal graft rejection, neovascular glaucoma, retrolental fibroplasia, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegeners sarcoidosis, Scleritis, Stevens Johnson disease, periphigoid radial keratotomy, corneal graph rejection, rheumatoid arthritis, osteoarthritis chronic inflammation (eg., ulcerative colitis or Crohn's disease), hemangioma, Osler-Weber-Rendu disease, and hereditary hemorrhagic telangiectasia.

In an embodiment the compounds of the present invention are useful for treating and preventing cancers selected from basal cell carcinoma, medulloblastoma, prostate, pancreatic, breast, colon, small cell lung cancers, sarcoma, lymphomas, leukemia, gastrointestinal cancer, multiple myeloma, glioma, heptacellular, sporadic and familial basal cell carcinomas, sporadic medulloblastoma, meningiomas, breast carcinoma, esophageal squamous cell carcinoma and bladder cancer.

In an embodiment the compounds of the present invention are useful for treating and preventing cancers associated with patched loss-of function.

In another embodiment the compounds of the present invention are useful for treating and preventing cancers associated with smoothened gain-of function.

The compounds of formula I are also useful as chemo- and radiosensitizers for cancer treatment. They are useful for the treatment of mammals who have previously undergone or are presently undergoing or will be undergoing treatment for cancer. Such other treatments include chemotherapy, radiation therapy, surgery or immunotherapy, such as cancer vaccines.

The instant compounds are particularly useful in combination with therapeutic, anti-cancer and/or radiotherapeutic agents. Thus, the present invention provides a combination of the presently compounds of formula I with therapeutic, anti-cancer and/or radiotherapeutic agents for simultaneous, separate or sequential administration. The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

The therapeutic agent, anti-cancer agent and/or radiation therapy can be administered according to therapeutic protocols well known in the art. It will be apparent to those skilled in the art that the administration of the therapeutic agent, anti-cancer agent and/or radiation therapy can be varied depending on the disease being treated and the known effects of the anti-cancer agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., anti-neoplastic agent or radiation) on the patient, and in view of the observed responses of the disease to the administered therapeutic agents, and observed adverse affects.

In one embodiment, the compounds of formula I can be administered in combination with one or more agent selected from an anti-inflammatory agent, antihistamine, anti-cancer agent, imununomodulator, therapeutic antibody and a protein kinase inhibitor, e.g., a tyrosine kinase inhibitor.

In another embodiment is provided a combination of a compound of formula I and an anti-cancer agent for simultaneous, separate or sequential administration.

Examples of cancer agents or chemotherapeutic agents for use in combination with the compounds of the present invention can be found in *Cancer Principles and Practice of Oncology* by V. T. Devita and S. Hellman (editors), 6$^{th}$ edition (Feb. 15, 2001), Lippincott Williams & Wilkins Publishers and WO 2006/061638. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. Examples of such agents are provided in WO 2006/061638.

Anticancer agents suitable for use in the combination therapy of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-161, and Teniposide [VM-261, etc.), and agents that target topoisomerase I (e.g., Camptothecin and Isirinotecan [CPT-1 11, etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D1, etc.), anthracyclines (e.g., Daunorubicin [Daunomycin, and Cerubidine], Doxorubicin [Adrianycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., alltransretinoic acid, etc.); 13) gene therapy techniques; 14) antisense therapy techniques; 15) tumor vaccines; 16) therapies directed against tumor metastases (e.g., Batimistat, etc.); 17) inhibitors of angiogenesis and kinase inhibitors.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Suitable therapeutic antibodies for use in the combination therapy of the present invention include antibodies directed against the HER2 protein, such as trastuzuinab; antibodies directed against growth factors or growth factor receptors, such as bevacizurnab, which targets vascular endothelial growth factor, and OSI-774, which targets epidermal growth factor; antibodies targeting integrin receptors, such as Vitaxin (also known as MEDI-522), and the like.

In an embodiment is provided a method of treating or preventing basal cell carcinoma, pancreatic cancer, prostate cancer, sarcoma, lymphomas, leukemia, gastrointestinal cancer, multiple myeloma, small cell lung cancer, glioma, breast cancer, heptacellular, or medulloblastoma, which method comprises administration to a patient in need thereof of an effective amount of a compound of formula I in combination with another anti-cancer agent.

In an embodiment is provided a method of treating or preventing psoriasis, which method comprises administration to a patient in need thereof of an effective amount of a compound of formula I in combination with one or more other anti-psoriasis agents including, but not limited to, corticosteroids, tar, calcipotriene, tazarotene, calcineurin inhibitors, ultraviolet irradiation, methotrexate, retinoids, cyclosporine, immunomodulatory drugs, etanercept, alefacept, efalizumab, and infliximab.

The compounds of the formula can be used in combination with radiation therapy. The phrase "radiation therapy" refers to the use of electromagnetic or particulate radiation in the treatment of neoplasia and includes the use of ionizing and non-ionizing radiation.

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be useful for treating or preventing cancer in combination with siRNA therapeutics.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®); zoledronate (Zometa®), nilotinib (Tasigna®); and dasatinib (Sprycel®).

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The compounds of this invention can be prepared according to the following procedures. All variables within the formulae are defined above.

Abbreviations used in the description of the chemistry and in the Examples that follow are:

eq.: equivalents; RT: room temperature; h.: hours; min.: minutes; aq.: aqueous; sol.: solution; RP-HPLC: reverse phase HPLC; EtOAc: ethyl acetate; HCl: hydrochloric acid; KOCN: potassium cyanate; DMF: dimethylformamide; DCE: dichloroethane; MeOH: methanol; DCM: dichloromethane; MeCN: acetonitrile; TFA: trifluoroacetic acid; DMSO-$d_6$: deuterated dimethylsulfoxide; NaOAc: sodium acetate; $Et_3N$: triethylamine; DIPEA: Di-iso-propylethylamine; CDI: 1,1'-carbonyldiimidazole; LDA: lithium diisopropylamide; LiHMDS: lithium bis(trimethylsilyl)amide; TBTU: O-(Benzotriazol-1-yl)-N,N,N',N'-tetramethyluronium tetrafluoroborate.

Compounds of formula I wherein L is —(C=O)(NH)(O)$_c$(CR$^8$R$^9$)$_d$(NR$^7$)$_e$— can be prepared by reacting a compound of formula IA with a compound of formula IB:

(IA)

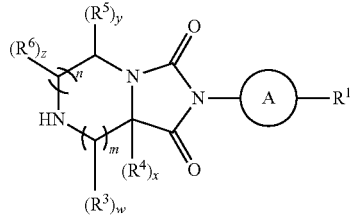

(IB)

wherein all variables are as defined above. The reaction is generally carried out in the presence of a base such as DIPEA or TEA, in a solvent such as DCM or MeCN at about RT. The solvent DCE may also be used.

Compounds of formula IA can be prepared in situ by reacting the corresponding amine of formula IC with an agent such as CDI:

$H_2N(O)_c(CR^8R^9)_d(NR^7)_eR^2$ (IC)

wherein all variables are as defined above, generally by reacting at about 80° C., in a solvent such as MeCN. A base such as LiHMDS may also be used in a solvent such as THF. The reaction can also be carried out utilizing triphosgene, generally in the presence of a base such as DIPEA, in a solvent such as DCM at about RT.

Compounds of formula IB can be prepared by cyclization of a compound of formula ID:

(ID)

wherein R$^x$ is C$_{1-6}$alkyl, for example methyl, P is a protecting group such as tert-butoxycarbonyl and all other variables are as defined above. The cyclization can generally be carried out in the presence of a base such as DIPEA, a solvent such a toluene at reflux. Alternatively, the cyclization can be carried out under acidic conditions, such as in the presence of an acid such as HCl, in a solvent such as dioxane at about RT.

The protecting group can be removed according to standard procedures. For example, when P is tert-butoxycarbonyl it can be removed by the addition of an acid such as TFA in a solvent such as DCM at about RT.

Compounds of formula ID can be prepared by reacting a compound of formula IE with a compound of formula IF:

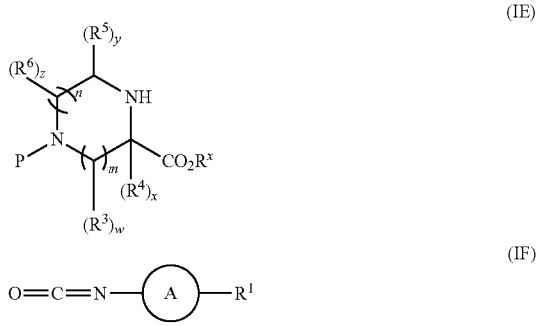

wherein all the variables are as defined above. The reaction is generally carried out in a solvent such as toluene or DCM at about RT.

Compounds of formula IF can be prepared by reacting a compound of formula IG with an agent such as CDI:

wherein all variables are as defined above, generally in a solvent such as MeCN at about 80° C. The reaction can also be carried out utilizing triphosgene, in a solvent such as DCM at about RT.

Compounds of formula IB wherein x is 1 can be prepared by reacting a compound of formula IB wherein x is 0 with a compound of formula $R^4$-$L^1$, wherein $L^1$ is a leaving group such as halogen, for example iodine. The reaction can generally be carried out in the presence of a strong base such as LDA and a solvent such as THF at about −78° C. to RT. During the reaction, compounds may be protected by protecting groups such as tert-butoxycarbonyl.

Compounds of formula I wherein a is 1 and X is C can be prepared by reacting a compound of formula IB with a compound of formula IH:

$$L^2\text{-}(C{=}O)(NR^7)_b(O)_c(CR^8R^9)_d(NR^7)_eR^2 \quad (IH)$$

wherein $L^2$ is a leaving group such as halogen, for example chlorine, and all other variables are as defined above. The reaction can be carried out in the presence of a base such as DIPEA or Et$_3$N in a solvent such as DCM at about RT. Alternatively, $L^2$ is hydroxy and the reaction can be carried out in the presence of a coupling reagent such as TBTU.

Alternatively, compounds of formula I wherein a is 1 and X is C can be prepared by reacting a compound of formula IB with a compound of formula IJ:

$$PhO\text{-}(C{=}O)(NR^7)_b(O)_c(CR^8R^9)_d(NR^7)_eR^2 \quad (IJ)$$

wherein all variables are as defined above. The reaction is generally carried out in the presence of a base such as TEA in a solvent such as DCM at about RT.

The compound of formula IJ wherein b is 1 and $R^7$ is hydrogen can be prepared by reacting a compound of formula IC with phenyl chloroformate, generally in a solvent such as DCE at about RT.

The compounds of this invention were prepared according to the following schemes. Other methods known in the art can also be used to synthesise the present compounds.

Scheme 1

Compounds from this invention can be prepared from suitably protected rings such as piperazine-2-carboxylic acid derivatives. Reaction of these piperazines with isocyanates gives an intermediate urea that can be cyclised to the required bicyclic hydantoin at reflux in toluene, in the presence of a tertiary amine base such as di-iso-propylethylamine. Alternatively, the urea can also be cyclised under acidic conditions at room temperature, such as 4M HCl solution in dioxane, to give the required bicyclic framework. Under these latter conditions, acid labile protecting groups such as Boc-groups can be removed during the cyclisation reaction. Derivitization of the other nitrogen atom can be accomplished by reaction with an isocyanate group, to yield the desired ureas. Alternatively, when not commercially available, isocyanates can be prepared in situ from an amine and triphosgene in a solvent such as DCM. The bicyclic system can also be reacted with an acyl imidazole intermediate obtained from the reaction of an amine with carbonyl diimidazole in MeCN at 80° C., condensation with the bicyclic hydantoin then yields the requisite urea. Alternatively, amines can be preactivated with phenyl chloroformate in solvents such as DCE to yield the corresponding phenyl carbonate, which can in turn be reacted with the bicyclic framework to yield the desired ureas as Smo antagonists. This latter reaction is typically conducted in a solvent such as DCM, at room temperature, in the presence of a trialkylamine base such as triethylamine. These compounds can be prepared chirally starting from enantiomerically pure piperazine-2-carboxylic acid derivatives, or alternatively can be separated using chiral SFC, or other separation techniques.

Coupling of the bicyclic framework with carboxylic acids, using a coupling agent such as TBTU, in solvents like DMF allows the formation of the corresponding amides which are themselves Smo antagonists. Similar compounds can be prepared by coupling of acyl chlorides with the scaffold in the presence of a trialkylamine base in a solvent such as DCM.

Scheme 1

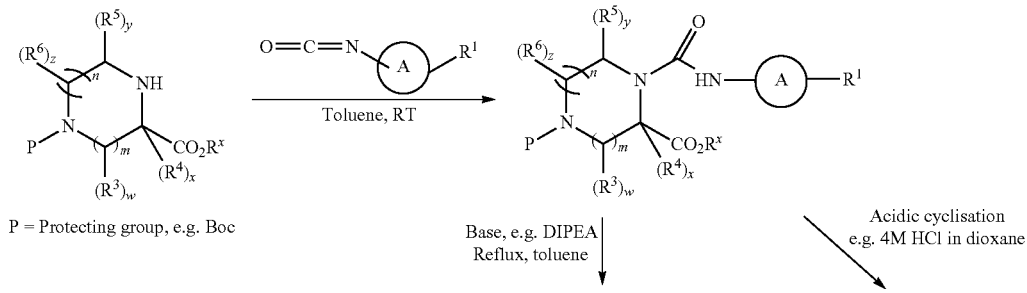

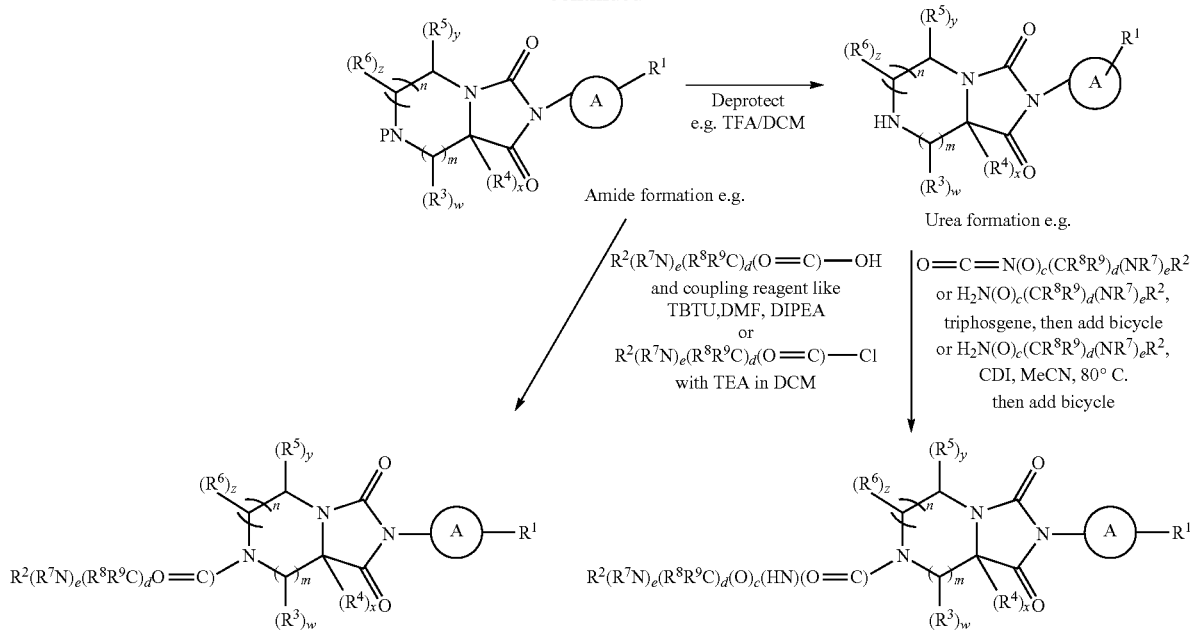

Scheme 2

An alternative synthetic strategy which allows variation of the right-hand side of the compounds of this invention involves the formation of the bicyclic hydantoin core by reaction of a ring such as a piperazine-2-carboxylic acid derivative with potassium cyanate in water and dioxane, in the presence of 1 equivalent of HCl (Scheme 2). The resulting bicyclic framework can then be reacted with neat vinyl acetate in the presence of catalytic $Na_2PdCl_4$ at reflux as described in *Eur. J. Org. Chem.* 2000, 1507. Palladium catalyzed Heck reaction, using $Pd(OAc)_2$ in the presence of LiBr and NaOAc at 90° C. in water and DMF, then yields the N-(2-aryl)vinyl derivatives as described in *J. Org. Chem.* 2006, 71, 8610. Simmons-Smith cyclopropanation of these enamides as described in *Angew. Chem. Int. Ed. Engl.* 2007, 46, 4069 using chloroiodomethane and diethylzinc in dichloroethane, then furnishes the trans-cyclopropane, with contemporary deprotection of the secondary amine, which is then ready to be functionalised to yield the desired Smo antagonists.

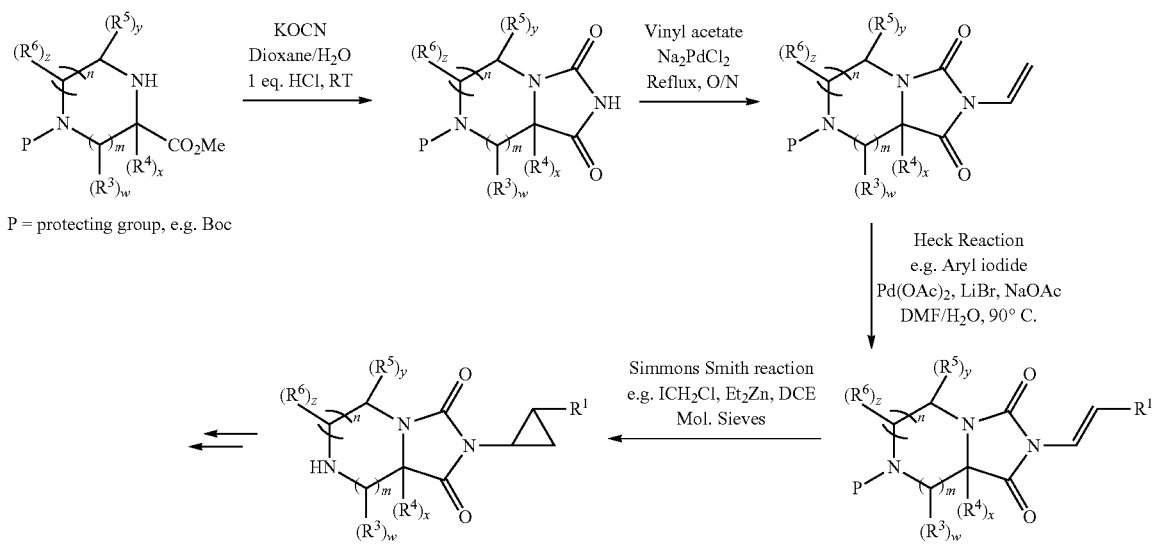

Scheme 2

Scheme 3

Once the bicyclic framework has been prepared it too can undergo further synthetic modifications. For instance, a suitable projected core scaffold can be deprotonated using a strong base such as LDA at −78° C. in solvent like THF. The resulting anion can be quenched with an alkylating agent, such as methyl iodide, warming the reaction from −78° C. to room temperature to ensure successful alkylation. The resulting functionalised core can then be manipulated as previous described.

Scheme 3

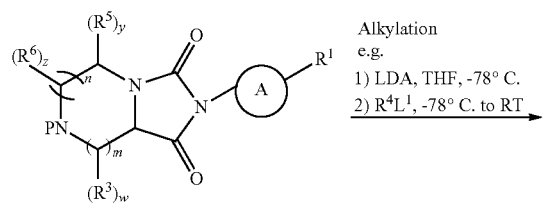

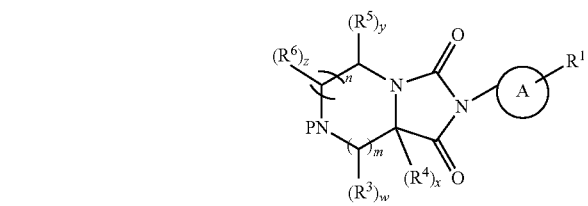

P = Protecting group, e.g. Boc
L¹ = Leaving group, e.g. I or Br

Where the synthesis of intermediates and starting materials is not described, these compounds are commercially available or can be made from commercially available compounds by standard methods or by extension of the synthesis above, schemes and Examples herein.

Compounds of formula I may be converted to other compounds of formula I by known methods or by methods described in the Examples herein.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis,* 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the Boc (tert-butoxycarbonyl) or benzylcarbonyl protecting group is present, it may be removed by the addition of solvents such as TFA, DCM and/or MeCN at about room temperature. The compound may also be hydrogenated using standard methods, such as treating with a catalyst such as Pd/C, in a solvent such as methanol under a hydrogen atmosphere. EtOAc in the presence of HCl and 1,4-dioxane may also be added to remove the benzylcarbonyl protecting group, at about room temperature.

When the compounds of the present invention have chiral centres, the enantiomers may be separated from the racemic mixtures by standard separating methods such as using SFC.

The exemplified compounds described herein and tested by the assays described below were found to have an $IC_{50}$ value of less than 5 uM.

Shh-Light II Reporter Assay
Assay designed to measure firefly and Renilla luciferase, in the same well.
Prior to assay the Shh-Light II cells (ATCC Catalog No. CRL-2795) were cultured in growth media
Assay Protocol:
Day −1: seed 60,000 Shh-Light II cells in assay medium 75 uL/well, in presence of DMSO/inhibitor.
Day 0: after overnight incubation at 37° C. 10% $CO_2$ add 3 uM of Purmorphamine (Calbiochem 540220) in water.
Day 1: After 30 hrs at 37° C. 10% $CO_2$ of incubation develop the assay, directly to cells in growth medium.
    Add 75 μl of DualGlow Luciferase Reagent (Promega, E2940)
    Incubate 10 min. in the dark
    Read plate at Luminometer: TopCount, by PerkinElmer
    Add 75 ul of DualGlow Stop & Glow
    Incubate 10 min. in the dark
    Read plate at Luminometer: TopCount, by PerkinElmer.
    Output is the ratio between FireFly/Renilla counts
Growth Media:
For growth:
DMEM: Dulbecco's Mod Eagle Medium with 0.11 G/L Pyr, with Pyridoxine. (GIBCO Cat No: 41966-029). The medium has complemented with 10% FCS (fetal bovine serum), 1% Penicillin-Streptomycin (10 mg/ml) (GIBCO, 15140-114) and 1% L-Glutamine 200 MM (100×) (GIBCO, 3042190) and 0.4 mg/ml of G418 (Roche) and 0.15 mg/ml Zeocyne (Invitrogen R-250-01). Cells cultured at 10% $CO_2$.
For assay:
DMEM: Dulbecco's Mod Eagle Medium with 0.11 G/L Pyr, with Pyridoxine. (GIBCO Cat No: 21063-045), without Phenol Red. The medium has complemented with 2% FCS (fetal bovine serum), 1% Penicillin-Streptomycin (10 mg/ml) (GIBCO, 15140-114) and 1% L-Glutamine 200 MM (100×) (GIBCO, 3042190). Cells cultured at 10% $CO_2$. DMSO 0.25%.
SHH Smo Binding Assay
In transfected Cos7 cells we are able to measure the binding of SMO ligand Cyclopamine-bodipy.
Assay Protocol:
Day −1: Seed 3,500,000 Cos7 cells in Petri dish 10 cm.
Day 0: Transfect cells with Lipofectamine-2000 (Invitrogen) and plasmid pSMO-Myc. After 5 hrs seed the cells in 96 well plate in growth DMEM (10% FCS); 15,000 cells per 100 ul well.
Day 1: 24 hrs after transfection, change the medium with assay DMEM (without Phenol Red 2% FCS) and add compound/DMSO 0.5%. Incubate at 37° C. 5% CO2.
Day 2: After 16 hrs, add Cyclopamine-Bodipy (Toronto Research Chemical, B674800) at the final concentration of 50 nM. Incubate for 4 hrs at 37° C. 5% $CO_2$. Then cells are fixed 10 minutes with 3.5% Formaldehyde 100 ul/well. Cells are washed 3 times with PBS and nuclei are stained with 1.5 uM Propidium Iodide. Read at Acumen Explorer.
    Growth Media:
For growth:
DMEM: GIBCO Dulbecco's Mod Eagle Medium with 0.11 G/L Pyr, with Pyridoxine (GIBCO, 41966-029). The medium has complemented with 10% FCS (GIBCO, 10106-169), 1% Penicillin-Streptomycin (10 mg/ml) (GIBCO, 15140-114) and 1% L-Glutamine 200 MM (100×) (GIBCO, 3042190). Cells cultured at 5% $CO_2$
For assay:
DMEM: GIBCO Dulbecco's Mod Eagle Medium with 0.11 G/L Pyr, with Pyridoxine (GIBCO, 21063-045) without Phenol Red. The medium has complemented with 2% FCS (GIBCO, 10106-169), 1% Penicillin-Streptomycin (10 mg/ml) (GIBCO, 15140-114) and 1% L-Glutamine 200 MM (100×) (GIBCO, 3042190). Cells cultured at 5% $CO_2$. DMSO 0.5%.

PREPARATIVE EXAMPLE 1

(1-tert-Butyl 3-methyl (3S)-1,3-piperazinedicarboxylate (AA3)

Step 1: (2S)-1-[(Benzyloxy)carbonyl]-4-(tert-butoxycarbonyl)-2-piperazinecarboxylic acid (AA1)

It was prepared from (2S)-2-piperazinecarboxylic acid dihydrochloride with slight modifications as described in *Molecular Discovery* 1998, 4, 221-232.

A solution of (2S)-2-piperazinecarboxylic acid dihydrochloride in a dioxane-water mixture (1:1, 0.164 M) was made basic (pH 11) with 50% aqueous NaOH. A 0.68 M solution of BOC—ON (1.1 eq.) in dioxane was added dropwise at RT to the above mixture and the reaction mixture was stirred at RT overnight. The mixture was extracted with $Et_2O$ (×3) and acidified with conc. HCl to pH 2. The aqueous layer was extracted with EtOAc (×3). The aqueous solution was basified to pH 10 with 50% NaOH. A solution N-(benzyloxycarbonyloxy)succinimide in dioxane (0.59 M) was added to the mixture at 0° C. The reaction mixture was stirred 3 h at RT. Dioxane was removed under reduced pressure. The basic solution was extracted with $Et_2O$ (×2) then acidified to pH 1 with conc. HCl, and extracted with EtOAc (×3). The combined organic layers were dried and evaporated. The residue was used as such in next step.

Step 2: 1-Benzyl 4-tert-butyl 2-methyl (2S)-1,2,4-piperazinetricarboxylate (AA2)

A solution of TMS-diazomethane (2.0 M in $Et_2O$, 4.0 eq.) was added to a stirred 0.16 M solution of AA1 in a toluene-MeOH mixture (2:1). The reaction mixture was stirred overnight at RT. Solvents were removed under reduced pressure. The residue was purified by column chromatography on silica gel, eluting with 20 to 100% EtOAc/petroleum ether to give the title compound in 92% yield. 97% ee by SFC. $[\alpha]_D^{20}$ -10.6 (c 1.00, $CHCl_3$). $^1H$ NMR (300 MHz, $CDCl_3$, 300K) δ 7.37 (5H, m), 5.18 (2H, m), 4.79-4.57 (2H, m), 4.10-3.90 (2H, m), 3.75 (1.5H, s), 3.70 (1.5H, s), 3.34-3.30 (1H, m), 3.10 (1H, dd, J=13.6, 4.4 Hz), 2.86 (1H, m), 1.45 (9H, s). MS ($ES^+$) $C_{19}H_{26}N_2O_6$ requires 378, found: 401 $(M+Na)^+$.

Step 3: 1-tert-Butyl 3-methyl (3S)-1,3-piperazinedicarboxylate (AA3)

10% Pd—C (0.2 eq.) was added to a stirred solution of AA2 in MeOH (0.1 M) at RT and the mixture was stirred under $H_2$ atmosphere at RT for 3 h. The mixture was filtered, washing with MeOH, and the filtrate was evaporated under reduced pressure to give the title compound in 89% yield. $^1H$ NMR (400 MHz, $CDCl_3$, 300K) δ 4.05 (1H, m), 3.76 (3H, s), 3.74-3.68 (1H, m), 3.44 (1H, dd, J=8.6, 3.5 Hz), 3.30-3.12 (1H, m), 3.10-3.00 (2H, m), 2.75 (1H, m), 2.17-1.74 (1H, m), 1.47 (9H, s). MS ($ES^+$) $C_{11}H_{20}N_2O_4$ requires 244, found: 267 $(M+Na)^+$.

PREPARATIVE EXAMPLE 2

[(1R,2S)-2-Isocyanatocyclopropyl]benzene (BB1)

Triphosgene (0.33 eq.) was added to a stirred, cooled 0° C., 0.053 M mixture of (2S,3S)-2,3-dihydroxysuccinic acid and (1S,2R)-2-phenylcyclopropanamine (1:1) (prepared according to: Newman in "Optical resolution procedures for chemical compounds" Chapter 1 Amines and related com. Pages 120-122) in a 1:1 mixture of DCM and sat. aq. $NaHCO_3$ solution, and the reaction mixture was stirred at 0° C. for 1 h. The reaction was poured into a separatory funnel and layers were separated. Aqueous layer was extracted with DCM (×3). Combined organic layers were dried and evaporated to give the title compound as colorless oil in quantitative yield. $^1H$ NMR (300 MHz, $CDCl_3$, 300K) δ 7.30 (2H, t, J=7.0 Hz), 7.21 (1H, t, J=7.0 Hz), 7.05 (2H, d, J=7.0 Hz), 2.92 (1H, ddd, J=7.4, 4.3, 3.3 Hz), 2.20 (1H, ddd, J=9.8, 6.8, 3.3 Hz), 1.33-1.20 (2H, m).

PREPARATIVE EXAMPLE 3

4-Chloro-2-methoxypyridin-3-amine (CC1)

To a stirred solution of 2-bromo-4-chloropyridin-3-amine (prepared as described in US2002/0119982) (1.0 eq.) in dry MeOH (0.25M) under argon was added a solution of NaOMe (25% wt in MeOH, 1.5 eq.) and the reaction mixture was refluxed for 1 h, more NaOMe (25% wt in MeOH, 1.5 eq) was added and the reaction mixture was refluxed for an additional 2 h. The volatiles were removed under reduced pressure and the crude product was purified by flash chromatography eluting with 2-10% EtOAc/petroleum ether affording the title compound as yellow oil. $^1H$-NMR (300 MHz, DMSO-$d_6$, 300K) δ 7.33 (1H, d, J=5.5 Hz), 6.88 (1H, d, J=5.5 Hz), 5.13 (2H, bs), 3.89 (3H, s). MS (ES) $C_6H_7ClN_2O$ requires: 158, found: 159, 161 $(M+H)^+$.

PREPARATIVE EXAMPLE 4

4-Chloro-2-methylpyridin-3-amine (DD1)

Following a modified synthetic procedure reported in WO 2005/016892, a mixture of 2-bromo-4-chloropyridin-3-amine (prepared as described in US2002/0119982) (1.0 eq.), trimethylboroxine (1.05 eq.), $K_2CO_3$ (3.5 eq.) and $PdCl_2$(dppf)-$CH_2Cl_2$ adduct (0.1 eq.) in 10:1 solution 1,4-dioxane:$H_2O$ (0.28M) was put in a 10-mL glass vial equipped with a small magnetic stirring bar. The reaction vessel was fitted with a rubber septum, was evacuated and back-filled with argon and sealed with an aluminum/Teflon crimp top. The reaction mixture was then irradiated for 1 h at 120° C., using an irradiation power of 100 W. After completion of the reaction, the vial was cooled to 50° C. with air jet cooling before it was opened. The reaction mixture was diluted with EtOAc and filtered on a pad of Solca Floc®200FCC. The crude product was purified by flash chromatography eluting with 5-100% EtOAc/petroleum ether affording the titled compound as violet oil. MS (ES) $C_6H_7ClN_2$ requires: 142, found: 143, 145 $(M+H)^+$.

PREPARATIVE EXAMPLE 5

4-Chloro-2-ethylpyridin-3-amine (EE1)

Following a modified synthetic procedure reported in *J. Org. Chem.* 2006, 71, 7322, a to a stirred solution of 2-bromo-4-chloropyridin-3-amine (prepared as described in US2002/0119982) (1.0 eq.), and $Pd(Ph_3P)_4$ (0.05 eq.) in dry THF (0.05M) under argon was added dropwise $Me_3Al$ (1.0M in hexane, 2.0 eq.) and the reaction mixture was refluxed for O/N. The volatiles were removed under reduced pressure and the crude product was purified by flash chromatography eluting with 5-100% EtOAc/petroleum ether affording the titled compound as orange oil. $^1$H NMR (300 MHz, DMSO-$d_6$, 300K) δ 7.67 (1H, d, J=5.2 Hz), 7.11 (1H, d, J=5.2 Hz), 5.26 (2H, br. s), 2.69 (2H, q, J=7.3 Hz), 1.73 (3H, t, J=7.3 Hz). MS (ES) $C_7H_9ClN_2$ requires: 156, found: 157, 159 (M+H)$^+$.

PREPARATIVE EXAMPLE 6

2-Cyclopropyl-4-methylpyridin-3-amine (FF1)

Following a modified synthetic procedure reported in *J. Org. Chem.* 2003, 68, 5534, a mixture of 2-bromo-4-methylpyridin-3-amine (1.0 eq.), potassium cyclopropyltrifluoroborate (2.0 eq.), $Cs_2CO_3$ (3.0 eq.) and $PdCl_2$(dppf)-$CH_2Cl_2$ adduct (0.1 eq.) in 10:1 solution $THF:H_2O$ (0.14M) was put in a 10-mL glass vial equipped with a small magnetic stirring bar. The reaction vessel was fitted with a rubber septum, was evacuated and back-filled with argon and sealed with an aluminum/Teflon crimp top. The reaction mixture was then heated for O/N at 80° C. After completion of the reaction, the vial was cooled to RT before it was opened. The reaction mixture was diluted with EtOAc and filtered on a pad of Solca Floc®200FCC. The crude product was purified by flash chromatography eluting with 10-100% EtOAc/petroleum ether affording the titled compound as brown oil. $^1$H-NMR (400 MHz, DMSO-$d_6$, 300K) δ 7.55 (1H, d, J=4.7 Hz), 6.75 (1H, d, J=4.7 Hz), 4.89 (2H, br. s), 2.13-2.04 (4H, m), 0.85-0.68 (4H, m). MS (ES) $C_9H_{12}N_2$ requires: 148, found: 149 (M+H)$^+$.

REPRESENTATIVE EXAMPLES

Example 1

N-Biphenyl-2-yl-1,3-dioxo-2-[trans-2-phenylcyclopropyl]hexahydroimidazo[1,5-a]pyrazine-7(1H)-carboxamide (A6)

Step 1: 1-[(benzyloxy)carbonyl]-4-(tert-butoxycarbonyl)piperazine-2-carboxylic acid (A1)

A solution 0.164 M of 2-piperazinecarboxylic acid dihydrochloride in a 1:1 dioxane-water mixture was made basic (pH 11) with 50% aqueous NaOH. A 0.68 M solution of Boc-ON (1.1 eq) in dioxane was added dropwise at RT to the above mixture and the reaction mixture was stirred at RT overnight. The mixture was extracted with $Et_2O$ (×3) and acidified with conc. HCl to pH 2. The aqueous layer was extracted with EtOAc (×3). The aqueous solution was basified to pH 10 with 50% NaOH. A 0.59 M solution N-(benzyloxycarbonyloxy)succinimide (1.1 eq.) in dioxane was added to the mixture at 0° C. The reaction mixture was stirred 3 h at RT. Dioxane was removed under reduced pressure. The basic solution was extracted with $Et_2O$ (×2) then acidified to pH 1 with conc. HCl, and extracted with EtOAc (×3). The combined organic layers were dried and evaporated. The residue was used as such in next step.

Step 2: 1-benzyl 4-tert-butyl 2-methyl piperazine-1,2,4-tricarboxylate (A2)

This step was carried out using the procedure described in *Tetrahedron Letters* 30 (39), 1989, 5193-5196. A 0.5 M solution of A1 in acetone was treated with $K_2CO_3$ (1.3 eq.) and $Me_2SO_4$ (1.2 eq.) and the mixture was refluxed 6 h. The reaction mixture was filtered and filtrate was concentrated under reduced pressure. The residue was dissolved in $Et_2O$ and washed with sat. aq. $NaHCO_3$ solution, and brine, then dried and evaporated. The residue was purified by column chromatography on silica gel, eluting with 20-100% EtOAc/petroleum ether to give the title compound in 90% yield. $^1$H NMR (300 MHz, CDCl$_3$, 300K) δ 7.35 (5H, m), 5.17 (2H, m), 4.77-4.50 (2H, m), 4.10-3.85 (1H, m), 3.74 (1.5H, s), 3.64 (1.5H, s), 3.30 (1H, m), 3.10 (1H, dd, J 13.6, 4.4), 2.86 (1H, m), 1.45 (9H, s). MS (ES$^+$) $C_{19}H_{26}N_2O_6$ requires 378, found: 401 (M+Na)$^+$.

Step 3: 1-tert-butyl 3-methyl piperazine-1,3-dicarboxylate (A3)

10% Pd—C (0.2 eq) was added to a stirred RT 0.1 M solution of A2 in MeOH and the mixture was stirred under an $H_2$ atmosphere at RT for 3 h. The mixture was filtered, washing with MeOH, and the filtrate was evaporated under reduced pressure to give the title compound in 95% yield. $^1$H NMR (400 MHz, CDCl$_3$, 300K) δ 4.02 (1H, m), 3.74 (3H, s), 3.70 (1H, m), 3.43 (1H, m), 3.20 (1H, m), 3.04 (2H, m), 2.75 (1H, m), 2.14 (1H, m), 1.47 (9H, s). MS (ES$^+$) $C_{11}H_{20}N_2O_4$ requires 244, found: 267 (M+Na)$^+$.

Step 4: tert-butyl 1,3-dioxo-2-[trans-2-phenylcyclopropyl]hexahydroimidazo[1,5-a]pyrazine-7(1H)-carboxylate (A4)

To A3 in toluene (0.4M) was added dropwise trans-2-phenylcyclopropyl isocyanate (1.05 eq.). The mixture was stirred O/N at rt. DIPEA (1.5 eq.) was added and the mixture refluxed for 20 h. The organic phase was washed with phosphate buffer (2×200 mL, 0.75 M $NaH_2PO_4$, pH~4.5) and the solvent removed under reduced pressure. The residue was purified by column chromatography on silica gel, eluting with 20-100% EtOAc/petroleum ether to give the title compound in 60% yield. MS (ES$^+$) $C_{20}H_{25}N_3O_4$ requires 371, found: 394 (M+Na)$^+$.

Step 5: 2-[trans-2-phenylcyclopropyl]tetrahydroimidazo[1,5-a]pyrazine-1,3(2H,5H)-dione (A5)

A solution of A4 in DCM (0.5 M) was cooled to 0° C. (ice bath) and TFA (9 eq.) was added and the reaction was stirred at RT overnight. The solvent was removed under reduced pressure. The crude material was treated with $Et_2O$ (20 mL) and HCl (1N, 12 mL). The two layers were separated, and organic phase washed with water (2×15 mL). To the combined organic extracts was added solid $K_2CO_3$ in small portion until pH 9-10. The mixture was extracted with DCM and combined extracts were dried and evaporated under reduced pressure to yield (100%) the desired compound that was used crude in the next step. $^1$H NMR (400 MHz, DMSO-d6, 300K) δ 7.29-7.20 (5H, m), 3.90 (1H, m), 3.78 (1H, m), 3.15 (1H, m), 2.85 (3H, m), 2.65 (1H, m), 2.50-2.30 (3H, m), 1.5 (1H, m), 1.35 (1H, m). MS (ES$^+$) $C_{15}H_{17}N_3O_2$ requires 271, found: 272 (M+H)$^+$.

Step 6: N-Biphenyl-2-yl-1,3-dioxo-2-[trans-2-phenylcyclopropyl]hexahydroimidazo[1,5-a]pyrazine-7(1H)-carboxamide (A6)

[1,1'-Biphenyl]-2-yl-isocyanate (1.1 eq) was added to a stirred solution of A5 and DIPEA (3.0 eq) in DCM (0.09 M), and the mixture was stirred at RT for 1 h. The solvents were removed under reduced pressure and the residue was purified by column chromatography on silica gel, eluting with 10-80% EtOAc/petroleum ether to give the title compound in 76% yield. $^1$H NMR (400 MHz, DMSO-d$_6$, 300K) δ 8.36 (1H, s), 7.43-7.38 (4H, m), 7.33-7.27 (7H, m), 7.20 (3H, m), 4.19 (1H, m), 3.93 (1H, m), 3.85-3.77 (2H, m), 2.86 (1H, m), 2.74 (2H, d, J=9.3 Hz), 2.67 (1H, m), 2.40-2.30 (1H, m), 1.58-1.48 (1H, m), 1.43-1.37 (1H, m). MS (ES$^+$) C$_{28}$H$_{26}$N$_4$O$_3$ requires 466, found: 467 (M+H)$^+$.

Example 2

N-(2,3-Dichlorophenyl)-1,3-dioxo-2-[trans-2-phenylcyclopropyl]hexahydroimidazo[1,5-a]pyrazine-7(1H)-carboxamide (B1)

Compound B1 was prepared according to procedure reported in Example 1. Yield 86%. $^1$H NMR (400 MHz, DMSO-d$_6$, 300K) δ 8.80 (1H, s), 7.43 (2H, m), 7.35-7.28 (3H, m), 7.23-7.18 (3H, m), 4.35 (1H, m), 4.14-4.09 (2H, m), 3.93 (1H, m), 3.04-2.92 (3H, m), 2.69 (1H, m), 2.42-2.35 (1H, m), 1.64-1.50 (1H, m), 1.41 (1H, m). MS (ES$^+$) C$_{22}$H$_{20}$Cl$_2$N$_4$O$_3$ requires 458, 460, found: 459, 461 (M+H)$^+$.

Example 3

N-Biphenyl-2-yl-1,3-dioxo-2-[trans-2-phenylcyclopropyl]hexahydroimidazo[1,5-a]pyrazine-7(1H)-carboxamide (Diastereomer 1), (8aS)-N-Biphenyl-2-yl-1,3-dioxo-2-[(1S,2R)-2-phenylcyclopropyl]hexahydroimidazo[1,5-a]pyrazine-7(1H)-carboxamide, N-Biphenyl-2-yl-1,3-dioxo-2-[trans-2-phenylcyclopropyl]hexahydroimidazo[1,5-a]pyrazine-7(1H)-carboxamide (Diastereomer 2) and N-Biphenyl-2-yl-1,3-dioxo-2-[trans-2-phenylcyclopropyl]hexahydroimidazo[1,5-a]pyrazine-7(1H)-carboxamide (Diastereomer 3) (C1, C2, C3 and C4)

The diastereomers of (A6) (Example 1) were separated with two sequential separations using a SFC system.

First purification—Column: Chiralpak IB (1×25 cm); flow: 10 mL/min; modifier: 30% (MeOH 0.2% DEA); T$_{col}$: 35° C.; P$_{col}$: 100 bar—gave two pairs of isomers that were purified separately—Column: Chiralcel OJ (1×25 cm); flow: 10 mL/min; modifier: 60% (MeOH 0.2% DEA); T$_{col}$: 35° C.; P$_{col}$: 100 bar—to obtain the four diastereomers classified in ordered of elution on column OJ-METH, gradient 20-60% MeOH+0.2% DEA:

First compound eluted: Retention time=8.39 min. yield 10% $^1$H NMR (400 MHz, DMSO-d$_6$, 300K) δ 8.36 (1H, s), 7.43-7.38 (4H, m), 7.33-7.27 (7H, m), 7.20 (3H, app. d, J=7 Hz), 4.20 (1H, dd, J=12.9, 4.1 Hz), 3.93 (1H, d, J=9.5 Hz), 3.82 (1H, dd, J=11.3, 4.8 Hz), 3.79 (1H, d, J=10.8 Hz), 2.87 (1H, dd, J=12.1, 12.1 Hz), 2.74 (1H, d, J=9.4 Hz), 2.66 (1H, m), 2.33 (1H, m), 1.55 (1H, ddd, J=9.5, 5.6, 4.9 Hz), 1.39 (1H, dd, J=13.5, 6.8 Hz). MS (ES$^+$) C$_{28}$H$_{26}$N$_4$O$_3$ requires 466, found: 467 (M+H)$^+$.

Second compound eluted: Retention time=10.15 min yield 10%. $^1$H NMR (400 MHz, DMSO-d$_6$, 300K) δ 8.36 (1H, s), 7.43-7.38 (4H, m), 7.33-7.27 (7H, m), 7.20 (3H, app. d, J=7 Hz), 4.19 (1H, dd, J=13.0, 4.1 Hz), 3.92 (1H, d, J=9.8 Hz), 3.82 (1H, dd, J=11.3, 4.9 Hz), 3.78 (1H, d, J=10.4 Hz), 2.86 (1H, dd, J=13.0, 11.3 Hz), 2.79-2.70 (2H, m), 2.66 (1H, m), 2.37 (1H, ddd, J=9.8, 6.7, 3.3 Hz), 1.51 (1H, ddd, J=9.9, 5.7, 4.4 Hz), 1.39 (1H, dd, J=13.6, 6.8 Hz). MS (ES$^+$) C$_{28}$H$_{26}$N$_4$O$_3$ requires 466, found: 467 (M+H)$^+$.

Third compound eluted: Retention time=10.76 min yield 10%. $^1$H NMR (400 MHz, DMSO-d$_6$, 300K) δ 8.36 (1H, s), 7.43-7.38 (4H, m), 7.33-7.27 (7H, m), 7.20 (3H, app. d, J=7 Hz), 4.19 (1H, dd, J=13.0, 4.1 Hz), 3.92 (1H, d, J=9.8 Hz), 3.82 (1H, dd, J=11.3, 4.9 Hz), 3.78 (1H, d, J=10.4 Hz), 2.86 (1H, dd, J=13.0, 11.3 Hz), 2.79-2.70 (2H, m), 2.66 (1H, m), 2.37 (1H, ddd, J=9.8, 6.7, 3.3 Hz), 1.51 (1H, ddd, J=9.9, 5.7, 4.4 Hz), 1.39 (1H, dd, J=13.6, 6.8 Hz). MS (ES$^+$) C$_{28}$H$_{26}$N$_4$O$_3$ requires 466, found: 467 (M+H)$^+$.

Fourth compound eluted: Retention time=11.49 min yield 10% $^1$H NMR (400 MHz, DMSO-d$_6$, 300K) δ 8.36 (1H, s), 7.43-7.38 (4H, m), 7.33-7.27 (7H, m), 7.20 (3H, app. d, J=7 Hz), 4.20 (1H, dd, J=12.9, 4.1 Hz), 3.93 (1H, d, J=9.5 Hz), 3.82 (1H, dd, J=11.3, 4.8 Hz), 3.79 (1H, d, J=10.8 Hz), 2.87 (1H, dd, J=12.1, 12.1 Hz), 2.74 (1H, d, J=9.4 Hz), 2.66 (1H, m), 2.33 (1H, m), 1.55 (1H, ddd, J=9.5, 5.6, 4.9 Hz), 1.39 (1H, dd, J=13.5, 6.8 Hz). MS (ES$^+$) C$_{28}$H$_{26}$N$_4$O$_3$ requires 466, found: 467 (M+H)$^+$.

Example 4

(8aS)-N-(2,3-Dichlorophenyl)-1,3-dioxo-2-[(1S,2R)-2-phenylcyclopropyl]hexahydroimidazo[1,5-a]pyrazine-7(1H)-carboxamide (D3)

Step 1: 1-tert-Butyl 3-methyl (3S)-4-({[(1S,2R)-2-phenylcyclopropyl]amino}carbonyl)-1,3-piperazinedicarboxylate (D1)

A solution of 1-tert-butyl 3-methyl (3S)-1,3-piperazinedicarboxylate (AA3) in DCM (0.17 M) was added to a stirred solution of [(1R,2S)-2-isocyanatocyclopropyl]benzene (1.0 eq.) in DCM (0.17 M) and the mixture was stirred at RT for 1 h. Solvents were evaporated under reduced pressure to give the title compound that was used as such in next step. MS (ES$^+$) C$_{21}$H$_{29}$N$_3$O$_5$ requires 403, found: 404 (M+H)$^+$.

Step 2: (8aS)-2-[(1S,2R)-2-Phenylcyclopropyl]tetrahydroimidazo[1,5-a]pyrazine-1,3(2H,5H)-dione HCl salt (D2)

4N HCl solution in dioxane (44 eq.) was added at RT to D1. The resulting 0.1 M solution obtained was stirred for 1 h at RT, then the solvent was removed under reduced pressure. The residue was co-evaporated with toluene (×3) and it was used as such in next step without further purification. MS (ES$^+$) C$_{15}$H$_{17}$N$_3$O$_2$ requires 271, found: 272 (M+H)$^+$.

Step 3: (8aS)-N-(2,3-Dichlorophenyl)-1,3-dioxo-2-[(1S,2R)-2-phenylcyclopropyl]hexahydro imidazo[1,5-a]pyrazine-7(1H)-carboxamide (D3)

2,3-Dichlorophenyl isocyanate (1.1 eq.) was added to a stirred solution of D2 and DIPEA (3.0 eq.) in DCM (0.09 M) and the mixture was stirred at RT for 1 h. The solvents were removed under reduced pressure. The residue was purified by column chromatography on silica gel, eluting with 10-80% EtOAc/petroleum ether to give the title compound in 67% yield, 92% de by SFC. $^1$H NMR (400 MHz, DMSO-d$_6$, 300K) δ 8.80 (1H, s), 7.45-7.42 (2H, m), 7.34-7.28 (3H, m), 7.23-7.18 (3H, m), 4.35 (1H, dd, J=12.9, 4.2 Hz), 4.14-4.09 (2H, m), 3.92 (1H, dd, J=13.0, 2.7 Hz), 3.07-2.99 (2H, m), 2.91 (1H, td, J=12.6, 3.0 Hz), 2.68 (1H, m), 2.39 (1H, ddd, J=9.8, 6.8, 3.2 Hz), 1.51 (1H, ddd, J=9.5, 5.7, 4.3 Hz), 1.41 (1H, dd, J=14.0, 7.1 Hz). MS (ES$^+$) C$_{22}$H$_{20}$Cl$_2$N$_4$O$_3$ requires 458, 460, found: 459, 461 (M+H)$^+$.

Example 5

(8aS)-N-2-biphenylyl-1,3-dioxo-2-[(1S,2R)-2-phenylcyclopropyl]hexahydroimidazo[1,5-a]pyrazine-7(1H)-carboxamide (C2)

The title compound was prepared, as described in example 4, using [1,1'-biphenyl]-2-yl-isocyanate (1.1 eq.) to give the desired compound in 67% yield, 92% de by SFC. $^1$H NMR (400 MHz, DMSO-$d_6$, 300K) δ 8.36 (1H, s), 7.43-7.38 (4H, m), 7.33-7.27 (7H, m), 7.20 (3H, app. d, J=7 Hz), 4.19 (1H, dd, J=13.0, 4.1 Hz), 3.92 (1H, d, J=9.8 Hz), 3.82 (1H, dd, J=11.3, 4.9 Hz), 3.78 (1H, d, J=10.4 Hz), 2.86 (1H, dd, J=13.0, 11.3 Hz), 2.79-2.70 (2H, m), 2.66 (1H, m), 2.37 (1H, ddd, J=9.8, 6.7, 3.3 Hz), 1.51 (1H, ddd, J=9.9, 5.7, 4.4 Hz), 1.39 (1H, dd, J=13.6, 6.8 Hz). MS (ES$^+$) $C_{28}H_{26}N_4O_3$ requires 466, found: 467 (M+H$^+$).

Example 6

N-Cyclohexyl-1,3-dioxo-2-[trans-2-phenylcyclopropyl]hexahydroimidazo[1,5-a]pyrazine-7(1H)-carboxamide (E1)

The title compound was prepared, as described in example 4. After workup the crude product was purified by preparative RP-HPLC using H$_2$O (0.1% TFA) and MeCN (0.1% TFA) as eluents. The desired fractions were lyophilized to afford the title compound in 44% yield. $^1$H NMR (400 MHz, DMSO-$d_6$, 300K) δ 7.31-7.18 (5H, m), 6.51 (1H, bs), 4-28-4.24 (1H, m), 4.02-3.95 (2H, m), 3.83 (1H, m), 3.41 (1H, m), 2.80 (1H, m), 2.77 (1H, m), 2.67 (2H, m), 2.40-2.29 (1H, m), 1.79-1.65 (4H, m), 1.61-1.47 (2H, m), 1.38 (1H, m), 1.25-1.15 (4H, m), 1.09 (1H, m). MS (ES$^+$) $C_{22}H_{28}N_4O_3$ requires 396, found: 397 (M+H)$^+$.

Example 7

(8aS)-1,3-Dioxo-2-[(1S,2R)-2-phenylcyclopropyl]-N-(1-phenyl-1H-pyrazol-5-yl)hexahydroimidazo[1,5-a]pyrazine-7(1H)-carboxamide (F2)

Synthesis A

Step 1: 1-Phenyl-1H-pyrazol-5-amine (F1)

5-Amino-4-carbethoxy-1-phenylpyrazole (1 eq.) was dissolved in 36% HCl solution (30 eq.) and the reaction mixture was stirred under reflux for overnight. The mixture was cooled, poured onto ice and made basic with NH$_4$OH. The mixture was extracted with DCM (×3). The combined organic fractions were washed with brine, dried (Na$_2$SO$_4$), and the solvent was evaporated under reduced pressure to obtain the product as pale yellow oil in 94% yield. MS (ES$^+$) $C_9H_9N_3$ requires 159, found: 160 (M+H)$^+$.

Step 2: (8aS)-1,3-dioxo-2-[(1S,2R)-2-phenylcyclopropyl]-N-(1-phenyl-1H-pyrazol-5-yl)hexahydroimidazo[1,5-a]pyrazine-7(1H)-carboxamide (F2)

F1 (1.0 eq.) was dissolved in MeCN (0.1M) and CDI (1.0 eq.) was added. The reaction was stirred at 80° C. for 5 h. After cooling at RT a solution of (D2) (0.5 eq.) and TEA (0.6 eq.) in MeCN (0.2M) was added dropwise. The mixture was stirred overnight. The solvents were removed under reduced pressure. Crude product was purified by preparative RP-HPLC using H$_2$O (0.1% TFA) and MeCN (0.1% TFA) as eluents. The desired fractions were lyophilized to afford the title compound in 33% yield. $^1$H NMR (400 MHz, DMSO-$d_6$, 300K) δ 8.91 (1H, s), 7.62 (1H, d, J=1.7 Hz), 7.54-7.47 (4H, m), 7.37 (1H, m), 7.30 (2H, m), 7.22-7.20 (3H, m), 6.31 (1H, d, J=1.7 Hz), 4.24 (1H, m), 4.02-3.96 (2H, m), 3.87 (1H, m), 2.97 (1H, m), 2.84 (2H, m), 2.67 (1H, m), 2.38 (1H, m), 1.52-1.48 (1H, m), 1.40 (1H, m). MS (ES$^+$) $C_{25}H_{24}N_6O_3$ requires 456, found: 457 (M+H$^+$).

Synthesis B

Step 1: Phenyl (1-phenyl-1H-pyrazol-5-yl)carbamate (F3)

1-Phenyl-1H-pyrazol-5-amine (1 eq) was dissolved in DCE (0.1M), phenylchloroformate (1.1 eq) was added. The reaction was stirred 1 h, then diluted with DCM and washed with water and brine, dried and concentrated under reduced pressure to afford the product in quantitave yield.

Step 2: (8aS)-1,3-Dioxo-2-[(1S,2R)-2-phenylcyclopropyl]-N-(1-phenyl-1H-pyrazol-5-yl)hexahydroimidazo[1,5-a]pyrazine-7(1H)-carboxamide (F2)

Example 4, D2 (1 eq) was dissolved in DCM (0.1M), F3 (1.5 eq) and TEA (1.5 eq) were added and the reaction was stirred at RT 6 h. The reaction was diluted with DCM and washed with water and brine, dried and concentrated under reduced pressure. The crude product was purified by flash chromatography on silica gel eluting with 10-100% EtOAc/petroleum ether to afford the title compound in 85% yield. $^1$H NMR (400 MHz, DMSO-$d_6$, 300K) δ 8.91 (1H, s), 7.62 (1H, d, J=1.7 Hz), 7.54-7.47 (4H, m), 7.37 (1H, m), 7.30 (2H, m), 7.22-7.20 (3H, m), 6.31 (1H, d, J=1.7 Hz), 4.24 (1H, m), 4.02-3.96 (2H, m), 3.87 (1H, m), 2.97 (1H, m), 2.84 (2H, m), 2.67 (1H, m), 2.38 (1H, m), 1.52-1.48 (1H, m), 1.40 (1H, m). MS (ES$^+$) $C_{25}H_{24}N_6O_3$ requires 456, found: 457 (M+H$^+$).

Example 8

(8aS)-N-[2-(3-Chlorophenyl)pyridin-3-yl]-1,3-dioxo-2-[(1S,2R)-2-phenylcyclopropyl]hexahydroimidazo[1,5-a]pyrazine-7(1H)-carboxamide (G3)

Step 1: 2-(3-Chlorophenyl)pyridin-3-amine (G1)

To the solution of 2-bromopyridin-3-amine in DME (0.1M) were added 2M aqueous Na$_2$CO$_3$ solution (2 eq.) and (3-chlorophenyl)boronic acid (1.1 eq). The mixture was degassed and placed under an argon atmosphere. PdCl$_2$(dppf) (0.02 eq) were added and the reaction was heated at reflux overnight under argon. After cooling the reaction was diluted with EtOAc and washed with water and brine, then dried and evaporated under reduced pressure to afford the titled compound which was used as such in the next step. MS (ES$^+$) $C_{11}H_9ClN_2$ requires 204, 206, found: 205, 207 (M+H)$^+$.

Step 2: 2-(3-Chlorophenyl)-3-isocyanatopyridine (G2)

G1 (1 eq.) was dissolved in DCM (0.1M) and DIPEA was added (4 eq.). This solution was slowly added to a solution of triphosgene (0.33 eq.) in DCM (1M). The reaction was stirred 30 min and used as such in the next step.

Step 3: N-[2-(3-chlorophenyl)pyridin-3-yl]-1,3-dioxo-2-[(1R,2S)-2-phenylcyclopropyl]hexahydro imidazo[1,5-a]pyrazine-7(1H)-carboxamide (G3)

The solution of G2 (2 eq.) in DCM was added dropwise to the solution D2 (1.0 eq.) and DIPEA (1.1 eq.) in DCE (0.1 M). The reaction was stirred for 4 h. Then the solvent was evaporated under vacuum and residue was purified by preparative RP-HPLC using H$_2$O (0.1% TFA) and MeCN (0.1% TFA) as eluents. The desired fractions were lyophilized to afford the title compound in 40% yield. $^1$H NMR (400 MHz, DMSO-d$_6$, 300K) δ 8.75 (1H, s), 8.49 (1H, d, J=3.5 Hz), 7.77 (1H, d, J=7.88), 7.66 (1H, bs), 7.61 (1H, d, J=7.08), 7.49-7.38 (3H, m), 7.32-7.28 (2H, m), 7.21 (3H, m), 4.26 (1H, dd, J=12.7, 3.9 Hz)), 3.96-3.86 (3H, m), 2.96 (1H, m), 2.83 (2H, m), 2.68 (1H, m), 2.39 (1H, m), 1.52 (1H, m), 1.41 (1H, m). MS (ES$^+$) C$_{27}$H$_{24}$ClN$_5$O$_3$ requires 501, 503 found: 502, 504 (M+H$^+$).

Example 9

(8aS)-N-Biphenyl-2-yl-2-[trans-2-(4-chlorophenyl)cyclopropyl]-1,3-dioxohexahydroimidazo[1,5-a]pyrazine-7(1H)-carboxamide (H5)

Step 1: tert-Butyl (8aS)-1,3-dioxohexahydroimidazo[1,5-a]pyrazine-7(1H)-carboxylate (H1)

To a stirred solution of 1-tert-butyl 3-methyl (3S)-piperazine-1,3-dicarboxylate (AA3) (1.0 eq.) and 6 N aq. HCl sol. (1.0 eq.) in 1,4-dioxane (1 M) was added a sol. of KOCN (2.0 eq.) in H$_2$O (2 M). The reaction mixture was stirred at RT for 2 h, then the organic solvent was removed under reduced pressure. The desired product precipitated from H$_2$O: it was filtered off, washed with cold water and dried at the high vacuum pump. Mother liquors were extracted with EtOAc, the organic phase was washed with brine, dried (Na$_2$SO$_4$), filtered and concentrated to dryness. The crude product was purified by flash chromatography on silica gel eluting with 10-100% EtOAc/petroleum ether to afford the desired product (H1) as a white powder which was combined with the previously isolated precipitate. $^1$H-NMR (300 MHz, DMSO-d$_6$, 300K) δ 10.95 (1H, bs), 4.15-4.00 (2H, m), 3.97-3.75 (2H, m), 2.97-2.67 (3H, m), 1.42 (9H, s). MS (ES) C$_{11}$H$_{17}$N$_3$O$_4$ requires: 255, found: 256 (M+H)$^+$.

Step 2: tert-Butyl (8aS)-1,3-dioxo-2-vinylhexahydroimidazo[1,5-a]pyrazine-7(1H)-carboxylate (H2)

A solution of (H1) (1.0 eq.) in vinyl acetate (60 eq.) was degassed under argon, then Na$_2$PdCl$_4$ (0.2 eq.) was added and the reaction mixture was heated to reflux for 18 h. The reaction mixture was diluted with EtOAc and filtered on a pad of SolcaFloc® 200 FCC. The solvent was removed under reduced pressure giving an orange sticky solid which was purified by flash chromatography on silica gel eluting with 10-100% EtOAc/petroleum ether to afford the title compound (H2) as a white powder. $^1$H-NMR (300 MHz, DMSO-d$_6$, 300K) δ 6.60 (1H, dd, J=9.7 and 16.3 Hz), 5.84 (1H, d, J=16.3 Hz), 4.96 (1H, d, J=9.7 Hz), 4.22-4.07 (2H, m), 4.00-3.83 (2H, m), 3.13-2.75 (3H, m), 1.43 (9H, s). MS (ES) C$_{13}$H$_{19}$N$_3$O$_4$ requires: 281, found: 304 (M+Na)$^+$.

Step 3: tert-Butyl (8aS)-2-[(E)-2-(4-chlorophenyl)vinyl]-1,3-dioxohexahydroimidazo[1,5-a]pyrazine-7(1H)-carboxylate (H3)

A mixture of (H2) (1.0 eq.), 1-chloro-4-iodobenzene (2.0 eq.), Pd(OAc)$_2$ (0.05 eq.), NaOAc (3.0 eq.) and LiBr (6.0 eq.) in DMF:H$_2$O sol. (10:1, 0.078 M) was placed in a sealed vial and stirred at 90° C. for 18 h under argon. The reaction mixture was diluted with EtOAc, washed with water, brine, dried (Na$_2$SO$_4$), filtered and concentrated to dryness. The crude product was purified by flash chromatography on silica gel eluting with 10-100% EtOAc/petroleum ether to afford the title compound (H3) as a yellow powder. $^1$H-NMR (300 MHz, DMSO-d$_6$, 300K) δ 7.57-7.47 (2H, m), 7.46-7.33 (3H, m), 7.10 (1H, d, J=15.2 Hz), 4.30-4.10 (2H, m), 4.05-3.85 (2H, m), 3.15-2.75 (3H, m), 1.44 (9H, s). MS (ES) C$_{19}$H$_{22}$ClN$_3$O$_4$ requires: 391, 393, found: 414, 416 (M+Na)$^+$.

Step 4: (8aS)-2-[trans-2-(4-chlorophenyl)cyclopropyl]tetrahydroimidazo[1,5-a]pyrazine-1,3(2H,5H)-dione (H4)

Molecular sieves (4 Å) and CH$_2$ClI (10.0 eq.) were added to a solution of (H3) (1.0 eq.) in anhydrous DCE (0.1 M), and the resulting mixture was stirred at RT for 30 min. Diethylzinc (1.0 M in hexanes, 5.0 eq.) was then added carefully dropwise. Stirring was continued at RT for 18 h. The reaction mixture was diluted with MeOH and the crude product was purified by Isolute® SCX cartridge to yield the title compound as a mixture of diastereomers which was used in the next step without further purification. MS (ES) C$_{15}$H$_{16}$ClN$_3$O$_2$ requires: 291, 293 found: 292, 294 (M+H)$^+$.

Step 5: (8aS)-N-biphenyl-2-yl-2-[trans-2-(4-chlorophenyl)cyclopropyl]-1,3-dioxohexahydroimidazo[1,5-a]pyrazine-7(1H)-carboxamide (H5)

To a stirred solution of (H4) (1.0 eq.) in anhydrous DCE (0.25 M) were added Et$_3$N (1.1 eq.) and [1,1'-biphen]-2-yl isocyanate (1.1 eq.). The reaction mixture was stirred at RT for 2 h, then diluted with DCM, washed with water, brine, dried (Na$_2$SO$_4$), filtered and concentrated to dryness. The crude product was purified by preparative RP-HPLC using H$_2$O (0.1% TFA) and MeCN (0.1% TFA) as eluents. The desired fractions were lyophilized to afford the title compound (H5) as a mixture of diastereomers as a pale yellow powder. $^1$H-NMR (400 MHz, DMSO-d$_6$, 300K) δ 8.36 (1H, bs), 7.42-7.20 (13H, m), 4.25-4.15 (1H, m), 3.99-3.87 (1H, m), 3.84-3.72 (2H, m), 2.89-2.78 (1H, m), 2.78-2.67 (2H, m), 2.67-2.61 (1H, m), 2.40-2.28 (1H, m), 1.60-1.46 (1H, m), 1.43-1.34 (1H, m). MS (ES) C$_{28}$H$_{25}$ClN$_4$O$_3$ requires: 500, 502 found: 501, 503 (M+H)$^+$.

The compounds in the following table were made according to the procedure described above.

| Example | Name | MWt | M + H$^+$ | Procedure of Example |
|---|---|---|---|---|
| 10 | N-[1-(3-Isopropenylphenyl)-1-methylethyl]-1,3-dioxo-2-[trans-2-phenylcyclopropyl]hexahydroimidazo[1,5-a]pyrazine-7(1H)-carboxamide | 472 | 473 | 1 |
| 11 | 1,3-Dioxo-2-[trans-2-phenylcyclopropyl]-N-[(1R)-1-phenylethy]hexahydroimidazo[1,5-a]pyrazine-7(1H)-carboxamide | 418 | 419 | 1 |

| Example | Name | MWt | M + H+ | Procedure of Example |
|---|---|---|---|---|
| 12 | N-(2,6-Dichlorophenyl)-1,3-dioxo-2-[trans-2-phenylcyclopropyl]hexahydroimidazo[1,5-a]pyrazine-7(1H)-carboxamide | 459 | 459 | 1 |
| 13 | N,N-Dibutyl-1,3-dioxo-2-[trans-2-phenylcyclopropyl]hexahydroimidazo[1,5-a]pyrazine-7(1H)-carboxamide | 426 | 427 | 1 |
| 14 | N-1,3-Benzodioxol-5-yl-1,3-dioxo-2-[trans-2-phenylcyclopropyl]hexahydroimidazo[1,5-a]pyrazine-7(1H)-carboxamide | 434 | 435 | 1 |
| 15 | Ethyl N-{[1,3-dioxo-2-[trans-2-phenylcyclopropyl]hexahydroimidazo[1,5-a]pyrazin-7(1H)-yl]carbonyl}methioninate | 474 | 475 | 1 |
| 16 | N-[4-(Benzyloxy)phenyl]-1,3-dioxo-2-[trans-2-phenylcyclopropyl]hexahydroimidazo[1,5-a]pyrazine-7(1H)-carboxamide | 496 | 497 | 1 |
| 17 | N-Biphenyl-4-yl-1,3-dioxo-2-[trans-2-phenylcyclopropyl]hexahydroimidazo[1,5-a]pyrazine-7(1H)-carboxamide | 466 | 467 | 1 |
| 18 | N-Hexyl-1,3-dioxo-2-[trans-2-phenylcyclopropyl]hexahydroimidazo[1,5-a]pyrazine-7(1H)-carboxamide | 398 | 399 | 1 |
| 19 | 4-({[1,3-Dioxo-2-[trans-2-phenylcyclopropyl]hexahydroimidazo[1,5-a]pyrazin-7(1H)-yl]carbonyl}amino)-N,N-dimethylbenzenaminium trifluoroacetate | 433 | 434 | 2 |
| 20 | 1,3-Dioxo-2-[trans-2-phenylcyclopropyl]-N-[2-(trifluoromethyl)phenyl]hexahydroimidazo[1,5-a]pyrazine-7(1H)-carboxamide | 458 | 459 | 1 |
| 21 | N-(2-Methoxyphenyl)-1,3-dioxo-2-[trans-2-phenylcyclopropyl]hexahydroimidazo[1,5-a]pyrazine-7(1H)-carboxamide | 420 | 421 | 1 |
| 22 | N-(2-Isopropylphenyl)-1,3-dioxo-2-[trans-2-phenylcyclopropyl]hexahydroimidazo[1,5-a]pyrazine-7(1H)-carboxamide | 432 | 433 | 1 |
| 23 | N-(2,6-Dichloro-4-fluorophenyl)-1,3-dioxo-2-[trans-2-phenylcyclopropyl]hexahydroimidazo[1,5-a]pyrazine-7(1H)-carboxamide | 476, 478 | 477 479 | 1 |
| 24 | N-(1-Methyl-1-phenylethyl)-1,3-dioxo-2-[trans-2-phenylcyclopropyl]hexahydroimidazo[1,5-a]pyrazine-7(1H)-carboxamide | 432 | 433 | 1 |
| 25 | N-(2-Chloro-4-fluorophenyl)-1,3-dioxo-2-[trans-2-phenylcyclopropyl]hexahydroimidazo[1,5-a]pyrazine-7(1H)-carboxamide | 442, 444 | 443 445 | 1 |
| 26 | N-(2-Chloropyridin-3-yl)-1,3-dioxo-2-[trans-2-phenylcyclopropyl]hexahydroimidazo[1,5-a]pyrazine-7(1H)-carboxamide | 425, 427 | 426 428 | 1 |
| 27 | N-Biphenyl-2-yl-N-methyl-1,3-dioxo-2-[trans-2-phenylcyclopropyl]hexahydroimidazo[1,5-a]pyrazine-7(1H)-carboxamide | 480 | 481 | 1 |
| 28 | (8aR)-N-(2,3-Dichlorophenyl)-1,3-dioxo-2-[(1R,2S)-2-phenylcyclopropyl]hexahydroimidazo[1,5-a]pyrazine-7(1H)-carboxamide | 458, 460 | 459, 461 | 4 |
| 29 | (8aR)-N-(2,3-Dichlorophenyl)-1,3-dioxo-2-[(1S,2R)-2-phenylcyclopropyl]hexahydroimidazo[1,5-a]pyrazine-7(1H)-carboxamide | 458, 460 | 459, 461 | 4 |
| 30 | 1,3-Dioxo-2-[trans-2-phenylcyclopropyl]-N-[2-(3-thienyl)pyridin-3-yl]hexahydroimidazo[1,5-a]pyrazine-7(1H)-carboxamide | 473 | 474 | 1 |
| 31 | N-(2,3-Dichloro-4-fluorophenyl)-1,3-dioxo-2-[trans-2-phenylcyclopropyl]hexahydroimidazo[1,5-a]pyrazine-7(1H)-carboxamide | 476, 478 | 477 479 | 1 |
| 32 | 1,3-Dioxo-2-[trans-2-phenylcyclopropyl]-N-[2-(3-thienyl)phenyl]hexahydroimidazo[1,5-a]pyrazine-7(1H)-carboxamide | 472 | 473 | 1 |
| 33 | (8aS)-N-(2,3-Dichlorophenyl)-1,3-dioxo-2-[(1R,2S)-2-phenylcyclopropyl]hexahydroimidazo[1,5-a]pyrazine-7(1H)-carboxamide | 458, 460 | 459, 461 | 4 |
| 34 | N-[2-Chloro-4-(methylsulfonyl)phenyl]-1,3-dioxo-2-[trans-2-phenylcyclopropyl]hexahydroimidazo[1,5-a]pyrazine-7(1H)-carboxamide | 502, 504 | 503 505 | 7 |

| Example | Name | MWt | M + H+ | Procedure of Example |
|---|---|---|---|---|
| 35 | N-(2-Chloro-4-cyano-6-methylphenyl)-1,3-dioxo-2-[trans-2-phenylcyclopropyl]hexahydroimidazo[1,5-a]pyrazine-7(1H)-carboxamide | 463, 465 | 464 466 | 7 |
| 36 | N-(2,6-Dichloro-4-cyanophenyl)-1,3-dioxo-2-[trans-2-phenylcyclopropyl]hexahydroimidazo[1,5-a]pyrazine-7(1H)-carboxamide | 483, 485 | 484 486 | 7 |
| 37 | N-(3-Chloro-2-methylphenyl)-1,3-dioxo-2-[trans-2-phenylcyclopropyl]hexahydroimidazo[1,5-a]pyrazine-7(1H)-carboxamide | 438, 440 | 439 441 | 1 |
| 38 | N-(2-Chloro-6-methylphenyl)-1,3-dioxo-2-[trans-2-phenylcyclopropyl]hexahydroimidazo[1,5-a]pyrazine-7(1H)-carboxamide | 438, 440 | 439 441 | 1 |
| 39 | N-(3,5-Dichlorophenyl)-1,3-dioxo-2-[trans-2-phenylcyclopropyl]hexahydroimidazo[1,5-a]pyrazine-7(1H)-carboxamide | 458, 460 | 459 461 | 1 |
| 40 | 1,3-Dioxo-2-[trans-2-phenylcyclopropyl]-N-(1-phenyl-1H-pyrazol-5-yl)hexahydroimidazo[1,5-a]pyrazine-7(1H)-carboxamide | 456 | 457 | 7 |
| 41 | N-[2-(1,3-Oxazol-5-yl)phenyl]-1,3-dioxo-2-[trans-2-phenylcyclopropyl]hexahydroimidazo[1,5-a]pyrazine-7(1H)-carboxamide | 457 | 458 | 1 |
| 42 | N-Biphenyl-2-yl-2-(cis-2-fluoro-2-phenylcyclopropyl)-1,3-dioxohexahydroimidazo[1,5-a]pyrazine-7(1H)-carboxamide | 484 | 485 | 1 |
| 43 | N-[2,6-Dichloro-4-(trifluoromethoxy)phenyl]-1,3-dioxo-2-[trans-2-phenylcyclopropyl]hexahydroimidazo[1,5-a]pyrazine-7(1H)-carboxamide | 542, 544 | 543 545 | 7 |
| 44 | N-[2,6-Dichloro-4-(trifluoromethyl)phenyl]-1,3-dioxo-2-[trans-2-phenylcyclopropyl]hexahydroimidazo[1,5-a]pyrazine-7(1H)-carboxamide | 526, 528 | 527 529 | 7 |
| 45 | Methyl 2-chloro-3-({[1,3-dioxo-2-[trans-2-phenylcyclopropyl]hexahydroimidazo[1,5-a]pyrazin-7(1H)-yl]carbonyl}amino)benzoate | 482, 484 | 483 485 | 1 |
| 46 | 1,3-Dioxo-2-[trans-2-phenylcyclopropyl]-N-(2-[3-(trifluoromethyl)phenyl]pyridin-3-yl}hexahydroimidazo[1,5-a]pyrazine-7(1H)-carboxamide | 535 | 536 | 8 |
| 47 | Methyl 3-({[1,3-dioxo-2-[trans-2-phenylcyclopropyl]hexahydroimidazo[1,5-a]pyrazin-7(1H)-yl]carbonyl}amino)-2-methylbenzoate | 462 | 463 | 1 |
| 48 | N-(3,5-Dichloropyridin-4-yl)-1,3-dioxo-2-[trans-2-phenylcyclopropyl]hexahydroimidazo[1,5-a]pyrazine-7(1H)-carboxamide | 461, 463 | 460 462 | 7 |
| 49 | N-[2-(2-Chlorophenyl)pyridin-3-yl]-1,3-dioxo-2-[trans-2-phenylcyclopropyl]hexahydroimidazo[1,5-a]pyrazine-7(1H)-carboxamide | 501, 503 | 502 504 | 8 |
| 50 | N-[2-(3-Chlorophenyl)pyridin-3-yl]-1,3-dioxo-2-[trans-2-phenylcyclopropyl]hexahydroimidazo[1,5-a]pyrazine-7(1H)-carboxamide | 501, 503 | 502 504 | 8 |
| 51 | (8aS)-N-2-Biphenylyl-1,3-dioxo-2-(trans-3-phenylcyclobutyl)hexahydroimidazo[1,5-a]pyrazine-7(1H)-carboxamide | 480 | 481 | 1 |
| 52 | N-Biphenyl-2-yl-2-[trans-2-(4-fluorophenyl)cyclopropyl]-1,3-dioxohexahydroimidazo[1,5-a]pyrazine-7(1H)-carboxamide | 484 | 485 | 9 |
| 53 | N-[2-(4-Chlorophenyl)pyridin-3-yl]-1,3-dioxo-2-[trans-2-phenylcyclopropyl]hexahydroimidazo[1,5-a]pyrazine-7(1H)-carboxamide | 501, 503 | 502 504 | 8 |
| 54 | N-[2-(2-Methoxyphenyl)pyridin-3-yl]-1,3-dioxo-2-[trans-2-phenylcyclopropyl]hexahydroimidazo[1,5-a]pyrazine-7(1H)-carboxamide | 497 | 498 | 8 |

-continued

| Example | Name | MWt | M + H+ | Procedure of Example |
|---|---|---|---|---|
| 55 | N-[2-(3-Methoxyphenyl)pyridin-3-yl]-1,3-dioxo-2-[trans-2-phenylcyclopropyl]hexahydroimidazo[1,5-a]pyrazine-7(1H)-carboxamide | 497 | 498 | 8 |
| 56 | N-[2-(4-Methoxyphenyl)pyridin-3-yl]-1,3-dioxo-2-[trans-2-phenylcyclopropyl]hexahydroimidazo[1,5-a]pyrazine-7(1H)-carboxamide | 497 | 498 | 8 |
| 57 | N-[2,6-Dichloro-4-(methylsulfonyl)phenyl]-1,3-dioxo-2-[trans-2-phenylcyclopropyl]hexahydroimidazo[1,5-a]pyrazine-7(1H)-carboxamide | 536, 538 | 537 539 | 7 |
| 58 | (8aS)-N-Biphenyl-2-yl-2-[trans-2-(4-methoxyphenyl)cyclopropyl]-1,3-dioxohexahydroimidazo[1,5-a]pyrazine-7(1H)-carboxamide | 496 | 497 | 9 |

Example 59

N-(Biphenyl-2-yl)-8a-methyl-1,3-dioxo-2-[(1S,2R)-2-phenylcyclopropyl]-hexahydro imidazo-[1,5-a]pyrazine-7(1H)-carboxamide (I3) and corresponding diastereomers: (8aS)-N-biphenyl-2-yl-8a-methyl-1,3-dioxo-2-[(1S,2R)-2-phenylcyclopropyl]hexahydroimidazo[1,5-a]pyrazine-7(1H)-carboxamide and (8aR)-N-biphenyl-2-yl-8a-methyl-1,3-dioxo-2-[(1S,2R)-2-phenylcyclopropyl]hexahydroimidazo[1,5-a]pyrazine-7(1H)-carboxamide (I3a and I3b)

Step 1: tert-Butyl 8a-methyl-1,3-dioxo-2-[(1S,2R)-2-phenylcyclopropyl]hexahydroimidazo-[1,5-c]-pyrazine-7(1H)-carboxylate (I1)

(A4) (Example 1) was dissolved in THF (0.1 M) and cooled at −78° C. LDA (3.0 eq, 2.0 M in THF) was then slowly added. After 1 h, MeI (5.0 eq) was added and the reaction was slowly warmed to RT. The reaction was then quenched with sat. aq. NH$_4$Cl solution and extracted with EtOAc. The combined organic layers were dried (Na$_2$SO$_4$) and concentrated under reduced pressure. The residue was purified by flash column on silica using 10-30% EtOAc/Petroleum ether to yield in 48% the desired (I1) as a foam. $^1$H NMR (400 MHz, CDCl$_3$, 300K) δ 7.32-7.24 (4H, m), 7.23-7.18 (1H, m), 4.30-4.10 (2H, m), 4.03 (1H, dd, J=13.6, 3.6 Hz), 3.10-3.00 (1H, m), 2.80-2.70 (3H, m), 2.60-2.50 (1H, m), 1.65-1.60 (1H, m), 1.48 (9H, s), 1.48-1.40 (1H, m), 1.44 (3H, s). MS (ES+) C$_{21}$H$_{27}$N$_3$O$_4$ requires 385, found: 408 (M+Na)+.

Step 2: 8a-Methyl-2-[(1S,2R)-2-phenylcyclopropyl]tetrahydroimidazo[1,5-a]pyrazine-1,3(2H,5H)-dione (I2) and Corresponding Diastereomers: (8aS)-8a-methyl-2-[(1S,2R)-2-phenylcyclopropyl]tetrahydroimidazo[1,5-a]pyrazine-1,3(2H,5H)-dione and (8aR)-8a-methyl-2-[(1S,2R)-2-phenylcyclopropyl]tetrahydroimidazo[1,5-a]pyrazine-1,3(2H,5H)-dione (I2a and I2b)

I2 was prepared following the procedure reported in Example 1 step 5 and the crude was purified using IST ISOLUTE® SPE column SCX (loading in MeOH; eluting with 3N NH$_3$ in MeOH). Yield=100%. $^1$H NMR (400 MHz, CD$_3$OD, 300K) δ 7.32-7.24 (4H, m), 7.22-7.16 (1H, m), 3.90 (1H, dd, J=13.6, 3.6 Hz), 3.10-2.90 (3H, m), 2.72-2.62 (2H, m), 2.60-2.50 (1H, m), 2.50-2.40 (1H, m), 1.60-1.50 (1H, m), 1.49 (3H, s), 1.43-1.40 (1H, m). MS (ES+) C$_{16}$H$_{19}$N$_3$O$_2$ requires 285, found: 286 (M+H)+.

The diastereoisomers of I2 were separated by chiral SFC purification (column: Chiralpak AD-H (1×25 cm), flow: 10 ml/min, T$_{col}$: 35° C., P$_{col}$: 100 bar, modifier: 25% $^i$PrOH+ 0.4% Et$_2$NH, using CO$_2$ as supercritical eluent). Evaporation of the solvent followed by lyophilization gave as oils:

First eluted diastereoisomer (I2a): t$_{ret}$=3.24 min; yield 31%: $^1$H NMR (400 MHz, CD$_3$CN, 300K) δ 7.35-7.30 (2H, m), 7.27-7.22 (3H, m), 3.83 (1H, dd, J=13.6, 3.6 Hz), 2.97 (1H, td, J=12.6, 3.6 Hz), 2.92-2.86 (2H, m), 2.70-2.65 (1H, m), 2.62 (1H, d, J=12.4 Hz), 2.50 (1H, td, J=12.4, 3.8 Hz), 2.41 (1H, ddd, J=10.0, 6.6, 3.6 Hz), 1.59 (1H, ddd, J=10.4, 6.0, 4.4 Hz), 1.47 (3H, s), 1.40 (1H, dd, J=13.8, 6.9 Hz). MS (ES+) C$_{16}$H$_{19}$N$_3$O$_2$ requires 285, found: 286 (M+H)+.

Second eluted diastereoisomer (I2b) t$_{ret}$=5.33 min; yield 37%: $^1$H NMR (400 MHz, CD$_3$CN, 300K) δ 7.33-7.30 (2H, m), 7.24-7.20 (3H, m), 3.81 (1H, dd, J=13.2, 3.6 Hz), 2.97 (1H, td, J=12.4, 3.6 Hz), 2.95-2.85 (2H, m), 2.70-2.60 (2H, m), 2.49 (1H, td, J=12.4, 3.6 Hz), 2.38 (1H, ddd, J=10.3, 6.8, 3.5 Hz), 1.59 (1H, ddd, J=10.4, 6.0, 4.4 Hz), 1.46 (3H, s), 1.41 (1H, dd, J=13.7, 6.8 Hz). MS (ES+) C$_{16}$H$_{19}$N$_3$O$_2$ requires 285, found: 286 (M+H)+.

Step 3: N-(Biphenyl-2-yl)-8a-methyl-1,3-dioxo-2-[(1S,2R)-2-phenylcyclopropyl]-hexahydro imidazo-[1,5-a]pyrazine-7(1H)-carboxamide (I3) and corresponding diastereomers: (8aS)-N-biphenyl-2-yl-8a-methyl-1,3-dioxo-2-[(1S,2R)-2-phenylcyclopropyl]hexahydroimidazo[1,5-a]pyrazine-7(1H)-carboxamide and (8aR)-N-biphenyl-2-yl-8a-methyl-1,3-dioxo-2-[(1S,2R)-2-phenylcyclopropyl]hexahydroimidazo[1,5-a]pyrazine-7(1H)-carboxamide (I3a and I3b)

Compound I3 was prepared following the procedure reported in Example 1 step 6 and the crude was purified by flash column on SiO$_2$ using 50% EtOAc/Petroleum ether to yield in 77% the desired (I3) as a white powder. $^1$H NMR (400 MHz, DMSO-d6, 300K) δ 8.25 (1H, s), 7.43-7.38 (4H, m), 7.35-7.26 (7H, m), 7.20 (3H, d, J=7.3 Hz), 4.02-3.90 (1H, m), 3.96-3.90 (1H, d, J=13.6 Hz), 3.80 (1H, d, J=13.6 Hz), 2.92-2.80 (2H, m), 2.78-2.73 (1H, m), 2.70-2.65 (1H, m), 2.38-2.30 (1H, m), 1.54 (1H, ddd, J=10.4, 6.0, 4.4 Hz), 1.38 (1H, dd, J=14.0, 6.8 Hz), 1.09 (3H, s). MS (ES+) C$_{29}$H$_{28}$N$_4$O$_3$ requires 480, found: 481 (M+H)+.

The diasteromers of (I3) were separated by chiral SFC purification (column: ChiralCel OJ-H (1×25 cm), flow: 10 ml/min, $T_{coi}$: 35° C., $P_{coi}$: 100 bar, modifier: 40% $^i$PrOH+ 0.4% Et$_2$NH, using CO$_2$ as supercritic eluent). Evaporation of the solvent followed by lyophilization gave as white powders:

First eluted diastereoisomer: $t_{ret}$=7.40 min; yield 36%'H NMR (400 MHz, DMSO-d6, 300K) δ 8.25 (1H, s), 7.42-7.38 (4H, m), 7.34-7.26 (7H, m), 7.20 (3H, d, J=7.6 Hz), 4.00 (1H, d, J=13.2 Hz), 3.95 (1H, d, J=13.2 Hz), 3.80 (1H, dd, J=12.9, 2.6 Hz), 2.90 (1H, d, J=13.0 Hz), 2.83 (1H, dd, J=12.9, 3.1 Hz), 2.75 (1H, dd, J=12.8, 3.0 Hz), 2.72-2.65 (1H, m), 2.40-2.30 (1H, m), 1.52 (1H, ddd, J=10.4, 6.0, 4.4 Hz), 1.38 (1H, dd, J=13.6, 6.8 Hz), 1.10 (3H, s). MS (ES$^+$) C$_{29}$H$_{28}$N$_4$O$_3$ requires 480, found: 481 (M+H)$^+$.

Second eluted diastereoisomer: $t_{ret}$=8.93 min; yield 41% $^1$H NMR (400 MHz, DMSO-d6, 300K) δ 8.25 (1H, s), 7.42-7.38 (4H, m), 7.34-7.25 (7H, m), 7.20 (3H, d, J=7.4 Hz), 4.00 (1H, d, J=12.4 Hz), 3.95 (1H, d, J=13.0 Hz), 3.80 (1H, dd, J=12.8, 2.4 Hz), 2.89 (1H, d, J=12.4 Hz), 2.84 (1H, dd, J=13.0, 3.0 Hz), 2.76 (1H, dd, J=12.6, 2.8 Hz), 2.72-2.65 (1H, m), 2.40-2.30 (1H, m), 1.54-1.46 (1H, m), 1.38 (1H, dd, J=13.6, 7.0 Hz), 1.09 (3H, s). MS (ES$^+$) C$_{29}$H$_{28}$N$_4$O$_3$ requires 480, found: 481 (M+H)$^+$.

Example 60

8a-methyl-1,3-dioxo-2-[(1S,2R)-2-phenylcyclopropyl]-N-(1-phenyl-1H-pyrazol-5-yl)hexahydroimidazo[1,5-a]pyrazine-7(1H)-carboxamide (J1) and the Corresponding Diastereomers: (8aS)-8a-methyl-1,3-dioxo-2-[(1S,2R)-2-phenylcyclopropyl]-N-(1-phenyl-1H-pyrazol-5-yl)hexahydroimidazo[1,5-a]pyrazine-7(1H)-carboxamide and (8aR)-8a-methyl-1,3-dioxo-2-[(1S,2R)-2-phenylcyclopropyl]-N-(1-phenyl-1H-pyrazol-5-yl)hexahydroimidazo[1,5-a]pyrazine-7(1H)-carboxamide (J1a and J1b)

Compound J1 was prepared from I2 following the procedure reported in Example 7 step 2 and the crude was purified by flash column on SiO$_2$ using 30-80% EtOAc/Petroleum ether to yield in 79% the desired (J1) as a white powder. $^1$H NMR (300 MHz, DMSO-d6, 300K) δ 8.75 (1H, s), 7.61 (1H, d, J=2.2 Hz), 7.56-7.44 (4H, m), 7.40-7.32 (1H, m), 7.30-7.25 (2H, m), 7.25-7.18 (3H, m), 6.27 (1H, d, J=2.2 Hz), 4.10-3.93 (2H, m), 3.84 (1H, d, J=12.6 Hz), 3.03 (1H, d, J=13.4 Hz), 2.96-2.90 (1H, m), 2.83 (1H, d, J=12.3 Hz) 2.74-2.66 (1H, m), 2.40-2.30 (1H, m), 1.58-1.48 (1H, m), 1.40 (1H, dd, J=13.5, 6.9 Hz), 1.18 (3H, s). MS (ES$^+$) C$_{26}$H$_{26}$N$_6$O$_3$ requires 470, found: 471 (M+H)$^+$.

The diasteromers of (J1) were separated by chiral SFC purification (column: Chiralpak IA (1×25 cm), flow: 10 ml/min, $T_{coi}$: 35° C., $P_{coi}$: 100 bar, modifier: 28% MeOH+ 0.2% Et$_2$NH, using CO$_2$ as supercritic eluent). Evaporation of the solvent followed by lyophilization gave as white powders:

First eluted diastereoisomer: $t_{ret}$=5.11 min; yield 43%. $^1$H NMR (400 MHz, DMSO-d6, 300K) δ 8.78 (1H, s), 7.62 (1H, d, J=1.8 Hz), 7.56-7.44 (4H, m), 7.40-7.32 (1H, m), 7.32-7.26 (2H, m), 7.23-7.16 (3H, m), 6.27 (1H, d, J=1.8 Hz), 4.08-4.02 (1H, m), 3.97 (1H, d, J=13.2 Hz), 3.85 (1H, dd, J=13.2, 2.8 Hz), 3.04-3.00 (1H, d, J=13.2 Hz), 3.00-2.90 (1H, m) 2.84-2.74 (1H, m), 2.72-2.66 (1H, m), 2.40-2.30 (1H, m), 1.55-1.47 (1H, m), 1.44-1.36 (1H, dd, J=14.2, 7.2 Hz), 1.19 (3H, s). MS (ES$^+$) C$_{26}$H$_{26}$N$_6$O$_3$ requires 470, found: 471 (M+H)$^+$.

Second eluted diastereoisomer: $t_{ret}$=6.47 min; yield 36%. $^1$H NMR (400 MHz, DMSO-d6, 300K) δ 8.66 (1H, s), 7.59 (1H, d, J=1.8 Hz), 7.56-7.54 (2H, m), 7.50-7.45 (2H, m), 7.36-7.35 (1H, m), 7.30-7.26 (2H, m), 7.25-7.16 (3H, d, J=13.3 Hz), 6.27 (1H, d, J=1.8 Hz), 4.08-3.96 (2H, m), 3.86 (1H, d, J=13.6 Hz), 3.04-3.00 (1H, d, J=13.3 Hz), 2.98-2.92 (1H, m) 2.84-2.74 (1H, m), 2.76-2.70 (1H, m), 2.42-2.36 (1H, m), 1.60-1.54 (1H, m), 1.42-1.36 (1H, m), 1.19 (3H, s). MS (ES$^+$) C$_{26}$H$_{26}$N$_6$O$_3$ requires 470, found: 471 (M+H)$^+$.

Example 61

1,3-Dioxo-2-[(1S,2R)-2-phenylcyclopropyl]-N-(4-phenylisoxazol-5-yl)hexahydroimidazo[1,5-a]pyrazine-7(1H)-carboxamide (K1)

4-Phenylisoxazol-5-amine (2 eq) was dissolved in THF (0.1M) and treated with LiHMDS (0.1N, 2 eq), after stirring for 1 h CDI (1 eq) was added. The suspension was stirred for a further 2 h and then A5 (1 eq, 0.1 M) was added and the reaction stirred 5 h. The reaction was quenched with sat. aq. NH$_4$Cl solution and then extracted with EtOAc. Organic layers were washed with brine, dried and concentrated under reduced pressure. The crude material was purified by preparative RP-HPLC using H$_2$O (0.1% TFA) and MeCN (0.1% TFA) as eluents. The desired fractions were lyophilized to afford the title compound in 30% yield. $^1$H NMR (400 MHz, DMSO, 300K) δ 9.68 (1H, s), 9.00 (1H, s), 7.54 (2H, m), 7.43 (2H, m), 7.30 (3H, m), 7.23 (3H, m), 4.35 (1H, m), 4.16-4.06 (2H, m), 3.17-2.88 (3H, m), 2.69 (1H, m), 2.42-2.31 (1H, m), 1.61-1.49 (1H, m), 1.45-1.39 (1H, m). MS (ES$^+$) C$_{25}$H$_{23}$N$_5$O$_4$ requires 457, found: 458 (M+H)$^+$.

Example 62

(8aS)-N-(4-Chloro-2-cyclopropylpyridin-3-yl)-1,3-dioxo-2-[(1S,2R)-2-phenylcyclopropyl]hexahydroimidazo[1,5-a]pyrazine-7(1H)-carboxamide (L2)

Step 1: 4-Chloro-2-cyclopropylpyridin-3-amine (L1)

Following a modified synthetic procedure reported in J. Org. Chem. 2003, 68, 5534 a mixture of 2-bromo-4-chloropyridin-3-amine (prepared as described in US2002/0119982) (1.0 eq.), cyclopropylboronic acid (2.0 eq.), Cs$_2$CO$_3$ (3.0 eq.) and PdCl$_2$(dppf)-CH$_2$Cl$_2$ adduct (0.1 eq.) in 10:1 solution THF:H$_2$O (0.14 M) was put in a 10-mL glass vial equipped with a small magnetic stirring bar. The reaction vessel was fitted with a rubber septum, was evacuated and back-filled with argon and sealed with an aluminum/Teflon crimp top. The reaction mixture was then irradiated for 1 h at 120° C., using an irradiation power of 100 W. After completion of the reaction, the vial was cooled to 50° C. with air jet cooling before it was opened. The reaction mixture was diluted with EtOAc and filtered on a pad of Solca Floc®200FCC. The crude product was purified by flash chromatography eluting with 5-100% EtOAc/petroleum ether affording the titled compound as yellow oil. $^1$H-NMR (400 MHz, DMSO-d$_6$, 300K) δ 7.59 (1H, d, J=5.1 Hz), 7.04 (1H, d, J=5.1 Hz), 5.42 (2H, br. s), 2.24-2.15 (1H, m), 0.92-0.82 (4H, m). MS (ES) C$_8$H$_9$ClN$_2$ requires: 168, found: 169, 171 (M+H)$^+$.

Step 2: (8aS)-N-(4-Chloro-2-cyclopropylpyridin-3-yl)-1,3-dioxo-2-[(1S,2R)-2-phenylcyclopropyl]hexahydroimidazo[1,5-a]pyrazine-7(1H)-carboxamide (L2)

L1 (1.0 eq.) and DIPEA (5.0 eq.) in DCM (0.1M) was slowly added to an ice cooled solution of triphosgene (0.33 eq.) in DCM (0.1M). The reaction mixture was stirred 30 min at RT and slowly added to a solution of Example 4, D2 (0.5 eq) and DIPEA (0.5 eq) in DCE (0.1M). The reaction mixture was stirred 3 h at RT, volatiles were removed under reduced pressure and the crude product was purified by preparative RP-HPLC using H$_2$O (0.1% TFA) and MeCN (0.1% TFA) as eluents. The desired fractions were lyophilized to afford the title compound as a white powder. $^1$H-NMR (400 MHz, DMSO-d$_6$, 300K) δ 8.80 (1H, br. s), 8.24 (1H, d, J=5.1 Hz), 7.34 (1H, d, J=5.1 Hz), 7.32-7.26 (2H, m), 7.25-7.17 (3H, m), 4.39 (1H, dd, J=4.1 and 13.0 Hz), 4.17-4.06 (2H, m), 3.97-3.90 (1H, m), 3.12-2.88 (3H, m), 2.72-2.65 (1H, m), 2.43-2.35 (1H, m), 2.30-2.20 (1H, m), 1.55-1.47 (1H, m), 1.45-1.38 (1H, m), 0.98-0.90 (4H, m). MS (ES) C$_{24}$H$_{24}$ClN$_5$O$_3$ requires: 465, found: 466, 468 (M+H)$^+$.

Example 63

(8aS)-N-[(E)-1-Acetyl-4-phenylpyrrolidin-3-yl]-1,3-dioxo-2-[(1S,2R)-2-phenylcyclopropyl]hexahydroimidazo[1,5-a]pyrazine-7(1H)-carboxamide (M3)

Step 1: tert-butyl (1-acetyl-4-phenylpyrrolidin-3-yl)carbamate (M1)

To an ice cooled stirred solution of tert-butyl (4-phenylpyrrolidin-3-yl)carbamate (prepared as described in *J. Med. Chem.* 1993, 36, 4139 starting from (2E)-3-phenylprop-2-enoic acid) (1.0 eq.) in dry DCM (0.1M) were slowly added acetyl chloride (4.0 eq.) and DIPEA (4.0 eq.). The reaction mixture was stirred for 1 h at RT, then diluted with DCM, washed with sat. aq. NaHCO$_3$ sol., water and brine. The solution was dried (Na$_2$SO$_4$), filtered and the solvent was removed under reduced pressure. The crude product was purified by flash chromatography eluting with 5-100% EtOAc/petroleum ether, then eluting with 0-10% MeOH/EtOAc affording the titled compound as yellow oil. MS (ES) C$_{17}$H$_{24}$N$_2$O$_3$ requires: 304, found: 305 (M+H)$^+$.

Step 2: 1-Acetyl-4-phenylpyrrolidin-3-amine (M2)

A stirred solution of M1 (1.0 eq.) in 10% TFA/DCM (0.1M) was stirred for 1 h at RT. The volatiles were removed under reduced pressure and the crude product was purified by SCX Isolute® cartridge affording the titled compound as yellow oil. MS (ES) C$_{12}$H$_{16}$N$_2$O requires: 204, found: 205 (M+H)$^+$.

Step 3: (8aS)-N-[(E)-1-Acetyl-4-phenylpyrrolidin-3-yl]-1,3-dioxo-2-[(1S,2R)-2-phenylcyclopropyl]hexahydroimidazo[1,5-a]pyrazine-7(1H)-carboxamide (M3)

A solution of M2 (1.0 eq.) and DIPEA (3.0 eq.) in DCM (0.1M) was slowly added to an ice cooled solution of triphosgene (0.33 eq.) in DCM (0.1M). The reaction mixture was stirred 30 min at RT and slowly added to a solution of Example 4, D2 (0.5 eq) and DIPEA (0.5 eq) in DCE (0.1M). The reaction mixture was stirred 3 h at RT, volatiles were removed under reduced pressure and the crude product was purified by flash chromatography eluting with 5-100% EtOAc/petroleum ether, then 0-10% MeOH/EtOAc affording the titled compound as a white powder. $^1$H-NMR (300 MHz, DMSO-d$_6$, 300K) δ 7.38-7.15 (10H, m), 7.06-6.90 (1H, m), 4.45-4.12 (2H, m), 4.02-3.68 (4.5H, m), 3.62-3.20 (3H, m overlapped to the water signal), 3.14-3.03 (0.5H, m), 2.91-2.60 (4H, m), 2.42-2.30 (1H, m), 1.96 (3H, s), 1.56-1.44 (1H, m), 1.44-1.32 (1H, m). MS (ES) C$_{28}$H$_{31}$N$_5$O$_4$ requires: 501, found: 502 (M+H)$^+$.

Example 64

(8aS)-7-[(1-Methylcyclopropyl)carbonyl]-2-[(1S,2R)-2-phenylcyclopropyl]tetrahydro imidazo[1,5-a]pyrazine-1,3(2H,5H)-dione (N1)

To a 0.2 M solution of Example 4, D2 (1 eq) in DMF were added 1-methylcyclopropanecarboxylic acid (1.1 eq), DIPEA (2.5 eq) and TBTU (1.5 eq). The reaction mixture was stirred at RT for 12 h. The crude product was purified by preparative RP-HPLC using H$_2$O (0.1% TFA) and MeCN (0.1% TFA) as eluents, affording the title compound. $^1$H NMR (300 MHz, DMSO-d6, 300K) δ: 7.27-7.09 (5H, m), 4.42-4.32 (1H, m), 4.19 (1H, d, J=9.3 Hz), 4.05-3.95 (1H, m), 3.91-3.82 (1H, m), 2.97-2.81 (3H, m), 2.65-2.57 (1H, m), 2.36-2.26 (1H, m), 1.49-1.40 (1H, m), 1.39-1.30 (1H, m), 1.18 (3H, s), 0.83-0.76 (2H, m), 0.54-0.48 (2H, m). MS (ES) C$_{20}$H$_{23}$N$_3$O$_3$ requires: 353, found: 354 (M+H)$^+$.

Example 65

(8aS)-7-(2,2-Dimethylpropyl)-2-[(1S,2R)-2-phenylcyclopropyl]tetrahydro imidazo[1,5-a]pyrazine-1,3 (2H,5H)-dione (O1)

To a stirred solution of Example 4, D2 (1 eq) and TEA (1.1 eq) in DCM (0.08M) was added pivaloyl chloride (2.1 eq) and the reaction mixture was stirred at 25° C. for 2 h. The crude product was purified by preparative RP-HPLC using H$_2$O (0.1% TFA) and MeCN (0.1% TFA) as eluents, affording the title compound. $^1$H NMR (400 MHz, DMSO-d6, 300K) 7.48-7.18 (5H, m), 4.75-4.63 (1H, m), 4.42-4.33 (1H, m), 4.05-3.93 (2H, m), 3.15-2.80 (3H, m), 2.72-2.63 (1H, m), 2.50-2.38 (1H, m), 1.58-1.51 (1H, m), 1.48-1.38 (1H, m), 1.35 (9H, s). MS (ES) C$_{20}$H$_{25}$N$_3$O$_3$ requires: 354 found: 355 (M+H)$^+$.

Example 66

(8aS)-N-(1-Acetyl-3-phenylpiperidin-4-yl)-1,3-dioxo-2-[(1S,2R)-2-phenylcyclopropyl]hexa hydroimidazo[1,5-a]pyrazine-7(1H)-carboxamide (P2)

Step 1: 4-({[(8aS)-1,3-Dioxo-2-[(1S,2R)-2-phenylcyclopropyl]hexahydroimidazo[1,5-a]pyrazin-7(1H)-yl]carbonyl}amino)-3-phenylpiperidinium trifluoroacetate. (P1)

The title compound was prepared, as described in Example 4 starting from tert-butyl 4-amino-3-phenylpiperidine-1-carboxylate. After workup the crude product was treated with a mixture of DCM:TFA (1:1, 0.1M) and the reaction mixture was stirred for 30 min at RT. Volatiles were removed under reduced pressure and the crude product was purified by preparative RP-HPLC using H$_2$O (0.1% TFA) and MeCN (0.1% TFA) as eluents. The desired fractions were lyophilized to afford the title compound in 33% yield. $^1$H NMR (300 MHz, DMSO-d$_6$, 300K) (mixture of conformers) δ 9.08-8.75 (1H, m), 8.58-8.35 (1H, m), 7.30-7.07 (10H, m), 6.68 (0.5H, d, J=8.7 Hz), 6.48 (0.5H, t, J=8.6 Hz), 4.25 (0.5H, m), 4.15-3.88 (1.5H, m), 3.86-3.50 (3.5H, m), 3.30-2.88 (5.5H, partially under water, m), 2.78-2.49 (2.5H, m), 2.34-2.14 (1.5H, m), 2.05-1.90 (1H, m), 1.80-1.57 (1H, m), 1.39 (1H, m), 1.30 (1H, m). MS (ES$^+$) C$_{27}$H$_{31}$N$_5$O$_3$ requires 473, found: 474 (M+H)$^+$.

Step 2: (8aS)-N-(1-Acetyl-3-phenylpiperidin-4-yl)-1,3-dioxo-2-[(1S,2R)-2-phenylcyclopropyl]hexahydroimidazo[1,5-a]pyrazine-7(1H)-carboxamide (P2)

To a solution of P1 (1 eq) and DIPEA (2 eq) in DCM (0.1M) at 0° C. were added acetyl chloride (4 eq) and DIPEA (4 eq).

After 30 min stirring at RT, the reaction was diluted with DCM, washed with sat. aq. NaHCO$_3$ solution (2×) and water. The organic layer was concentrated under reduced pressure. The compound was lyophilized from a 1:1 mixture CH$_3$CN/H$_2$O to afford the title compound in 68% yield. $^1$H NMR (400 MHz, DMSO-d$_6$, 300K) (mixture of conformers) δ 7.38-7.28 (5H, m), 7.27-7.19 (5H, m), 6.63 (0.5H, d, J=8.7 Hz), 6.40-6.49 (0.5H, m), 4.51 (0.25H, d, J=12.8 Hz), 4.41 (0.25H, d, J=11.4 Hz), 4.28-3.40 (7H, m), 3.36-3.24 (m, 1H), 3.23-3.18 (m, 0.25H), 3.08-3.00 (m, 0.25H), 2.85-2.56 (5H, partially under solvent, m), 2.43-2.28 (1.3H, m), 2.10 (2.3H, m), 2.00 (0.7H, s), 1.96-1.84 (0.7H, m), 1.83-1.62 (1H, m), 1.52 (1H, m), 1.42 (1H, m). MS (ES$^+$) C$_{29}$H$_{33}$N$_5$O$_4$ requires 515, found: 516 (M+H)$^+$.

The compounds in the following table were made according to the procedures described above.

| Example | Name | MWt | M + H$^+$ | Procedure of Example |
|---|---|---|---|---|
| 67 | (8aS)-N-(1,1-Dioxidotetrahydro-2H-thiopyran-4-yl)-1,3-dioxo-2-[(1S,2R)-2-phenylcyclopropyl]hexahydroimidazo[1,5-a]pyrazine-7(1H)-carboxamide | 446 | 447 | 8 |
| 68 | (8aS)-N-Biphenyl-2-yl-2-[2-(2-methoxyphenyl)cyclopropyl]-1,3-dioxohexahydroimidazo[1,5-a]pyrazine-7(1H)-carboxamide | 496 | 497 | 9 |
| 69 | (8aS)-N-(2,6-Dichloro-4-fluorophenyl)-1,3-dioxo-2-[(1S,2R)-2-phenylcyclopropyl]hexahydroimidazo[1,5-a]pyrazine-7(1H)-carboxamide | 477 | 477, 479 | 8 |
| 70 | (8aS)-N-{2-[3-(Methylsulfonyl)phenyl]pyridin-3-yl}-1,3-dioxo-2-[(1S,2R)-2-phenylcyclopropyl]hexahydroimidazo[1,5-a]pyrazine-7(1H)-carboxamide | 546 | 547 | 8 |
| 71 | (8aS)-1,3-Dioxo-2-[(1S,2R)-2-phenylcyclopropyl]-N-[2-(3-thienyl)pyridin-3-yl]hexahydroimidazo[1,5-a]pyrazine-7(1H)-carboxamide | 474 | 475 | 8 |
| 72 | (8aS)-N-Biphenyl-2-yl-2-[2-(3,4-difluorophenyl)cyclopropyl]-1,3-dioxohexahydroimidazo[1,5-a]pyrazine-7(1H)-carboxamide | 502 | 503 | 9 |
| 73 | (8aS)-N-Biphenyl-2-yl-2-[2-(3-methoxyphenyl)cyclopropyl]-1,3-dioxohexahydroimidazo[1,5-a]pyrazine-7(1H)-carboxamide | 496 | 497 | 9 |
| 74 | (8aS)-N-(2,6-Dichloro-4-cyanophenyl)-1,3-dioxo-2-[(1R,2S)-2-phenylcyclopropyl]hexahydroimidazo[1,5-a]pyrazine-7(1H)-carboxamide | 484 | 484, 486 | 9 |
| 75 | (8aS)-N-[1-(3-Chlorophenyl)-1H-pyrazol-5-yl]-1,3-dioxo-2-[(1S,2R)-2-phenylcyclopropyl]hexahydroimidazo[1,5-a]pyrazine-7(1H)-carboxamide | 491 | 491, 493 | 8 |
| 76 | (8aS)-N-Biphenyl-2-yl-2-[2-(2,4-difluorophenyl)cyclopropyl]-1,3-dioxohexahydroimidazo[1,5-a]pyrazine-7(1H)-carboxamide | 502 | 503 | 5 |
| 77 | (8aS)-1,3-Dioxo-2-[(1S,2R)-2-phenylcyclopropyl]-N-(5-phenyl-1,3-oxazol-2-yl)hexahydroimidazo[1,5-a]pyrazine-7(1H)-carboxamide | 457 | 458 | 61 |
| 78 | (8aS)-N-Biphenyl-2-yl-2-[2-(4-cyanophenyl)cyclopropyl]-1,3-dioxohexahydroimidazo[1,5-a]pyrazine-7(1H)-carboxamide | 491 | 492 | 9 |
| 79 | (8aS)-N-Biphenyl-2-yl-2-[2-(3-cyanophenyl)cyclopropyl]-1,3-dioxohexahydroimidazo[1,5-a]pyrazine-7(1H)-carboxamide | 491 | 492 | 9 |
| 80 | (8aS)-1,3-Dioxo-N-[(1R,2S)-2-phenylcyclohexyl]-2-[(1S,2R)-2-phenylcyclopropyl]hexahydroimidazo[1,5-a]pyrazine-7(1H)-carboxamide | 472 | 473 | 6 |
| 81 | (8aS)-1,3-Dioxo-2-[(1S,2R)-2-phenylcyclopropyl]-N-(1,2,3,4-tetrahydronaphthalen-1-yl)hexahydroimidazo[1,5-a]pyrazine-7(1H)-carboxamide | 444 | 445 | 6 |
| 82 | (8aS)-N-{2,6-Dichloro-4-[(dimethylamino)carbonyl]phenyl}-1,3-dioxo-2-[(1S,2R)- | 530 | 530, 532 | 61 |

-continued

| Example | Name | MWt | M + H+ | Procedure of Example |
|---|---|---|---|---|
| | phenylcyclopropyl]hexahydroimidazo[1,5-a]pyrazine-7(1H)-carboxamide | | | |
| 83 | (8aS)-N-(2-Chloro-4,6-dimethylphenyl)-1,3-dioxo-2-[(1S,2R)-2-phenylcyclopropyl]hexahydroimidazo[1,5-a]pyrazine-7(1H)-carboxamide | 453 | 453, 455 | 8 |
| 84 | (8aS)-N-[2,6-dichloro-4-(methylsulfonyl)phenyl]-1,3-dioxo-2-[(1S,2R)-2-phenylcyclopropyl]hexahydroimidazo[1,5-a]pyrazine-7(1H)-carboxamide | 537 | 537, 539 | 61 |
| 85 | (8aS)-N-Cyclohexyl-1,3-dioxo-2-[(1S,2R)-2-phenylcyclopropyl]hexahydroimidazo[1,5-a]pyrazine-7(1H)-carboxamide | 396 | 397 | 1 |
| 86 | (8aS)-N-(4-Chloro-2-methoxypyridin-3-yl)-1,3-dioxo-2-[(1S,2R)-2-phenylcyclopropyl]hexahydroimidazo[1,5-a]pyrazine-7(1H)-carboxamide | 455 | 456 | 62 |
| 87 | (8aS)-N-(4-Chloro-2-methylpyridin-3-yl)-1,3-dioxo-2-[(1S,2R)-2-phenylcyclopropyl]hexahydroimidazo[1,5-a]pyrazine-7(1H)-carboxamide | 439 | 440 | 62 |
| 88 | (8aS)-N-(4-Chloro-2-ethylpyridin-3-yl)-1,3-dioxo-2-[(1S,2R)-2-phenylcyclopropyl]hexahydroimidazo[1,5-a]pyrazine-7(1H)-carboxamide | 453 | 454 | 62 |
| 89 | (8aS)-N-[1-(3-Fluorophenyl)-1H-pyrazol-5-yl]-1,3-dioxo-2-[(1S,2R)-2-phenylcyclopropyl]hexahydroimidazo[1,5-a]pyrazine-7(1H)-carboxamide | 474 | 475 | Example 7, Synthesis B |
| 90 | (8aS)-N-[1-(3,5-Dichlorophenyl)-1H-pyrazol-5-yl]-1,3-dioxo-2-[(1S,2R)-2-phenylcyclopropyl]hexahydroimidazo[1,5-a]pyrazine-7(1H)-carboxamide | 525 | 525, 527 | Example 7, Synthesis B |
| 91 | (8aS)-1,3-Dioxo-N-(2-oxo-1,2,3,4-tetrahydroquinolin-4-yl)-2-[(1S,2R)-2-phenylcyclopropyl]hexahydroimidazo[1,5-a]pyrazine-7(1H)-carboxamide | 459 | 460 | 6 |
| 92 | (8aS)-N-(6-Fluoro-2-oxo-1,2,3,4-tetrahydroquinolin-4-yl)-1,3-dioxo-2-[(1S,2R)-2-phenylcyclopropyl]hexahydroimidazo[1,5-a]pyrazine-7(1H)-carboxamide | 477 | 478 | 6 |
| 93 | (8aS)-N-(2,4-Dimethylpyridin-3-yl)-1,3-dioxo-2-[(1S,2R)-2-phenylcyclopropyl]hexahydroimidazo[1,5-a]pyrazine-7(1H)-carboxamide | 419 | 420 | 62 |
| 94 | (8aS)-7-[(1-Methylcyclohexyl)carbonyl]-2-[(1S,2R)-2-phenylcyclopropyl]tetrahydroimidazo[1,5-a]pyrazine-1,3(2H,5H)-dione | 396 | 397 | 64 |
| 95 | 3-({[(8aS)-1,3-Dioxo-2-[(1S,2R)-2-phenylcyclopropyl]hexahydroimidazo[1,5-a]pyrazin-7(1H)-yl]carbonyl}amino)-2-(4-fluorophenyl)pyridinium trifluoroacetate | 485 | 486 | 8 |
| 96 | 3-({[(8aS)-1,3-Dioxo-2-[(1S,2R)-2-phenylcyclopropyl]hexahydroimidazo[1,5-a]pyrazin-7(1H)-yl]carbonyl}amino)-2,3'-bipyridinium bis(trifluoroacetate) | 468 | 469 | 8 |
| 97 | 2-(3-Cyanophenyl)-3-({[(8aS)-1,3-Dioxo-2-[(1S,2R)-2-phenylcyclopropyl]hexahydroimidazo[1,5-a]pyrazin-7(1H)-yl]carbonyl}amino)pyridinium trifluoroacetate | 492 | 493 | 8 |
| 98 | 3-({[(8aS)-1,3-Dioxo-2-[(1S,2R)-2-phenylcyclopropyl]hexahydroimidazo[1,5-a]pyrazin-7(1H)-yl]carbonyl}amino)-2-(1-methyl-1H-pyrazol-1-ium-4-yl)pyridinium bis(trifluoroacetate) | 471 | 472 | 8 |
| 99 | 3-({[(8aS)-1,3-Dioxo-2-[(1S,2R)-2-phenylcyclopropyl]hexahydroimidazo[1,5-a]pyrazin-7(1H)-yl]carbonyl}amino)-2-phenylpyridinium trifluoroacetate | 467 | 468 | 8 |
| 100 | (8aS)-N-(2-Cyclopropyl-4-methylpyridin-3-yl)-1,3-dioxo-2-[(1S,2R)-2- | 445 | 446 | 62 |

-continued

| Example | Name | MWt | M + H⁺ | Procedure of Example |
|---|---|---|---|---|
| | phenylcyclopropyl]hexahydroimidazo[1,5-a]pyrazine-7(1H)-carboxamide | | | |
| 101 | 4-({[(8aS)-1,3-Dioxo-2-[(1S,2R)-2-phenylcyclopropyl]hexahydroimidazo[1,5-a]pyrazin-7(1H)-yl]carbonyl}amino)-3-phenylpyridinium trifluoroacetate | 467 | 468 | 8 |
| 102 | (8aS)-7-(2,2-Dimethylbutanoyl)-2-[(1S,2R)-2-phenylcyclopropyl]tetrahydroimidazo[1,5-a]pyrazine-1,3(2H,5H)-dione | 369 | 370 | 64 |
| 103 | (8aS)-7-(2,2-Dimethylpentanoyl)-2-[(1S,2R)-2-phenylcyclopropyl]tetrahydroimidazo[1,5-a]pyrazine-1,3(2H,5H)-dione | 383 | 384 | 64 |
| 104 | (8aS)-7-(2,2-Dimethylpent-4-enoyl)-2-[(1S,2R)-2-phenylcyclopropyl]tetrahydroimidazo[1,5-a]pyrazine-1,3(2H,5H)-dione | 381 | 382 | 64 |
| 105 | (8aS)-N-[1-(Methylsulfonyl)-3-phenylpiperidin-4-yl]-1,3-dioxo-2-[(1S,2R)-2-phenylcyclopropyl]hexahydroimidazo[l,5-a]pyrazine-7(1H)-carboxamide | 551 | 552 | 66 |
| 106 | 4-({[(8aS)-1,3-Dioxo-2-[(1S,2R)-2-phenylcyclopropyl]hexahydroimidazo[1,5-a]pyrazin-7(1H)-yl]carbonyl}amino)-1-methyl-3-phenylpiperidinium trifluoroacetate | 487 | 488 | 66 |
| 107 | 7-[(4-Methyltetrahydro-2-1H-pyran-4-yl)carbonyl]-2-[(2R)-2-phenylcyclopropyl]tetrahydroimidazo[1,5-a]pyrazine-1,3(2H,5H)-dione | 397 | 398 | 64 |
| 108 | 7-[(1-Ethynylcyclohexyl)carbonyl]-2-[(2R)-2-phenylcyclopropyl]tetrahydroimidazo[1,5-a]pyrazine-1,3(2H,5H)-dione | 406 | 407 | 64 |
| 109 | 1,3-Dioxo-2-[(1S,2R)-2-phenylcyclopropyl]-N-(1-phenyl-1H-pyrazol-5-yl)hexahydroimidazo[1,5-a]pyrazine-7(1H)-carboxamide | 457 | 457 | 7 |
| 110 | (8aR)-1,3-Dioxo-2-[(1S,2R)-2-phenylcyclopropyl]-N-(1-phenyl-1H-pyrazol-5-yl)hexahydroimidazo[1,5-a]pyrazine-7(1H)-carboxamide | 457 | 457 | Example 7, Synthesis B |
| 111 | (8aS)-N-[(+-)trans-1-Acetyl-3-phenylpiperidin-4-yl]-1,3-dioxo-2-[(1S,2R)-2-phenylcyclopropyl]hexahydroimidazo[1,5-a]pyrazine-7(1H)-carboxamide | 515 | 516 | 66 (+sep) |
| 112 | (8aS)-N-[(+-)cis-1-Acetyl-3-phenylpiperidin-4-yl]-1,3-dioxo-2-[(1S,2R)-2-phenylcyclopropyl]hexahydroimidazo[1,5-a]pyrazine-7(1H)-carboxamide | 515 | 516 | 66 (+sep) |
| 113 | (8aS)-N-[(+-)trans-1-(Methylsulfonyl)-3-phenylpiperidin-4-yl]-1,3-dioxo-2-[(1S,2R)-2-phenylcyclopropyl]hexahydroimidazo[1,5-a]pyrazine-7(1H)-carboxamide | 551 | 552 | 66 (+sep) |
| 114 | (8aS)-N-[(+-)cis-1-(Methylsulfonyl)-3-phenylpiperidin-4-yl]-1,3-dioxo-2-[(1S,2R)-2-phenylcyclopropyl]hexahydroimidazo[1,5-a]pyrazine-7(1H)-carboxamide | 551 | 552 | 66 (+sep) |

The compounds in the following table were made according to the procedures described above:

| Example | Name | MWt | M + H⁺ | Method |
|---|---|---|---|---|
| 115 | (8aS)-N-[4-(4-Fluorophenyl)-1-methyl-1H-pyrazol-5-yl]-1,3-dioxo-2-[(1S,2R)-2-phenylcyclopropyl]hexahydroimidazo[1,5-a]pyrazine-7(1H)-carboxamide | 488 | 489 | 7 |
| 116 | (8aS)-N-[3-(3-Fluorophenyl)-1-methyl-1H-pyrazol-4-yl]-1,3-dioxo-2-[(1S,2R)-2-phenylcyclopropyl]hexahydroimidazo[1,5-a]pyrazine-7(1H)-carboxamide | 488 | 489 | 7 |
| 117 | (8aS)-7-[(l-Acetyl-4-methylpiperidin-4-yl)carbonyl]-2-[(1S,2R)-2- | 438 | 439 | 66 |

-continued

| Example | Name | MWt | M + H⁺ | Method |
|---|---|---|---|---|
| | phenylcyclopropyl]tetrahydroimidazo[1,5-a]pyrazine-1,3(2h,5h)-dione | | | |
| 118 | (8aS)-N-(Cyclopentyl)-1,3-dioxo-2-[(1S,2R)-2-phenylcyclopropyl]hexahydroimidazo[1,5-a]pyrazine-7(1H)-carboxamide | 382 | 383 | 6 |
| 119 | (8aS)-N-(4,4-Dimethylcyclohexyl)-1,3-dioxo-2-[(1S,2R)-2-phenylcyclopropyl]hexahydroimidazo[1,5-a]pyrazine-7(1H)-carboxamide | 424 | 425 | 6 |
| 120 | (8aS)-1,3-Dioxo-N-(l-phenylcyclohexyl)-2-[(1S,2R)-2-phenylcyclopropyl]hexahydroimidazo[1,5-a]pyrazine-7(1H)-carboxamide | 472 | 473 | 6 |
| 121 | (8aS)-N-(2-Methylcyclohexyl)-1,3-dioxo-2-[(1S,2R)-2-phenylcyclopropyl]hexahydroimidazo[1,5-a]pyrazine-7(1H)-carboxamide | 410 | 411 | 6 |
| 122 | (8aS)-N-(3-Methylcyclohexyl)-1,3-dioxo-2-[(1S,2R)-2-phenylcyclopropyl]hexahydroimidazo[1,5-a]pyrazine-7(1H)-carboxamide | 410 | 411 | 6 |
| 123 | (8aS)-N-[trans-4-Methylcyclohexyl]-1,3-dioxo-2-[(1S,2R)-2-phenylcyclopropyl]hexahydroimidazo[1,5-a]pyrazine-7(1H)-carboxamide | 410 | 411 | 6 |
| 124 | (8aS)-1,3-Dioxo-N-[trans-2-phenylcyclohexyl]-2-[(1S,2R)-2-phenylcyclopropyl]hexahydroimidazo[1,5-a]pyrazine-7(1H)-carboxamide | 486 | 487 | 6 |
| 125 | (8aS)-N-(1-Methylcyclohexyl)-1,3-dioxo-2-[(1S,2R)-2-phenylcyclopropyl]hexahydroimidazo[1,5-a]pyrazine-7(1H)-carboxamide | 410 | 411 | 6 |
| 126 | (8aS)-N-(4-tert-Butylcyclohexyl)-1,3-dioxo-2-[(1S,2R)-2-phenylcyclopropyl]hexahydroimidazo[1,5-a]pyrazine-7(1H)-carboxamide | 452 | 453 | 6 |
| 127 | (8aS)-1,3-Dioxo-N-(4-phenylcyclohexyl)-2-[(1S,2R)-2-phenylcyclopropyl]hexahydroimidazo[1,5-a]pyrazine-7(1H)-carboxamide | 472 | 473 | 6 |
| 128 | (8aS)-1,3-Dioxo-2-[(1S,2R)-2-phenylcyclopropyl]-N-[(2R)-1,7,7-trimethylbicyclo[2.2.1]hept-2-yl]hexahydroimidazo[1,5-a]pyrazine-7(1H)-carboxamide | 450 | 451 | 6 |
| 129 | (8aS)-1,3-Dioxo-2-[(1S,2R)-2-phenylcyclopropyl]-N-[(1R,2S)-1,7,7-trimethylbicyclo[2.2.1]hept-2-yl]hexahydroimidazo[1,5-a]pyrazine-7(1H)-carboxamide | 450 | 451 | 6 |
| 130 | (8aS)-N-[1,1'-(cis or trans)Bi(cyclohexyl)-2-yl]-1,3-dioxo-2-[(1S,2R)-2-phenylcyclopropyl]hexahydroimidazo[1,5-a]pyrazine-7(1H)-carboxamide | 478 | 479 | 6 |
| 131 | (8aS)-N-[1,1'-(trans or cis) Bi(cyclohexyl)-2-yl]-1,3-dioxo-2-[(1S,2R)-2-phenylcyclopropyl]hexahydroimidazo[1,5-a]pyrazine-7(1H)-carboxamide | 478 | 479 | 6 |
| 132 | (8aS)-1,3-Dioxo-2-[(1S,2R)-2-phenylcyclopropyl]-N-(tetrahydro-2H-pyran-4-yl)hexahydroimidazo[1,5-a]pyrazine-7(1H)-carboxamide | 398 | 399 | 6 |
| 133 | N-[2,6-Dichloro-4-(methylsulfonyl)phenyl]-8a-methyl-1,3-dioxo-2-[(1S,2R)-2-phenylcyclopropyl]hexahydroimidazo[1,5-a]pyrazine-7(1H)-carboxamide | 550, 552 | 551, 553 | 60 |
| 134 | 3-({[8aS-Methyl-1,3-dioxo-2-[(1S,2R)-2-phenylcyclopropyl]hexahydroimidazo[1,5-a]pyrazin-7(1H)-yl]carbonyl}amino)-2-(3-thienyl)pyridiniumtrifluoroacetate | 487 | 488 | 60 |
| 135 | 2-[(1S,2R)-2-(3,5-Dibromophenyl)cyclopropyl]-N-[1-(3,5-dichlorophenyl)-1H-pyrazol-5-yl]-8aS-methyl-1,3-dioxohexahydroimidazo[l,5-a]pyrazine-7(1H)-carboxamide | 696, 698 | 697, 699 | 7B |
| 136 | (8aS)-N-[(1R,2S,5R)-5-Methyl-2-(propan-2-yl)cyclohexyl]-1,3-dioxo-2-[(1S,2R)-2- | 452 | 453 | 6 |

-continued

| Example | Name | MWt | M + H⁺ | Method |
|---|---|---|---|---|
| 137 | phenylcyclopropyl]hexahydroimidazo[1,5-a]pyrazine-7(1H)-carboxamide<br>(8aS)-N-[(1S,2S)-2-{[(4-Methylphenyl)sulfonyl]amino}cyclohexyl]-1,3-dioxo-2-[(1S,2R)-2-phenylcyclopropyl]hexahydroimidazo[1,5-a]pyrazine-7(1H)-carboxamide | 565 | 566 | 6 |
| 138 | (8aS)-N-[(1R,2R)-2-{[(4-Methylphenyl)sulfonyl]amino}cyclohexyl]-1,3-dioxo-2-[(1S,2R)-2-phenylcyclopropyl]hexahydroimidazo[1,5-a]pyrazine-7(1H)-carboxamide | 565 | 566 | 6 |
| 139 | (8aS)-N-(4,4-Difluoro-cyclohexyl)-1,3-dioxo-2-[(1S,2R)-2-phenylcyclopropyl]hexahydroimidazo[1,5-a]pyrazine-7(1H)-carboxamide | 432 | 433 | 6 |
| 140 | 4-({[(8aS)-1,3-Dioxo-2-[(1S,2R)-2-phenylcyclopropyl]hexahydroimidazo[1,5-a]pyrazin-7(1H)-yl]carbonyl}amino)-1-phenylpiperidinium trifluoroacetate | 473 | 474 | 6 |
| 141 | cis 3-Benzyl-4-({[(8aS)-1,3-dioxo-2-[(1S,2R)-2-phenylcyclopropyl]hexahydroimidazo[1,5-a]pyrazin-7(1H)-yl]carbonyl}amino)-1-methylpiperidinium trifluoroacetate | 501 | 502 | 6 |
| 142 | 4-({[(8aS)-1,3-Dioxo-2-[(1S,2R)-2-phenylcyclopropyl]hexahydroimidazo[1,5-a]pyrazin-7(1H)-yl]carbonyl}amino)-3-fluoropiperidinium trifluoroacetate | 415 | 416 | 6 |
| 143 | (8aS)-N-[1-(Methylsulfonyl)piperidin-4-yl]-1,3-dioxo-2-[(1S,2R)-2-phenylcyclopropyl]hexahydroimidazo[1,5-a]pyrazine-7(1H)-carboxamide | 475 | 476 | 6 |
| 144 | (8aS)-N-[(trans)-1-Acetyl-3-fluoropiperidin-4-yl]-1,3-dioxo-2-[(1S,2R)-2-phenylcyclopropyl]hexahydroimidazo[1,5-a]pyrazine-7(1H)-carboxamide | 457 | 458 | 66 |
| 145 | (8aS)-N-[(trans)-3-Fluoro-1-(methylsulfonyl)piperidin-4-yl]-1,3-dioxo-2-[(1S,2R)-2-phenylcyclopropyl]hexahydroimidazo[1,5-a]pyrazine-7(1H)-carboxamide | 493 | 494 | 6 |
| 146 | (8aS)-N[tran)-3-Fluoro-1-(phenylsulfonyl)piperidin-4-yl]-1,3-dioxo-2-[(1S,2R)-2-phenylcyclopropyl]hexahydroimidazo[1,5-a]pyrazine-7(1H)-carboxamide | 555 | 556 | 6 |
| 147 | (8aS)-N-[(cis)-3-Fluoro-1-(methylsulfonyl)piperidin-4-yl]-1,3-dioxo-2-[(1S,2R)-2-phenylcyclopropyl]hexahydroimidazo[1,5-a]pyrazine-7(1H)-carboxamide | 493 | 494 | 6 |
| 148 | (8aS)-N-[(cis)-1-Acetyl-3-fluoropiperidin-4-yl]-1,3-dioxo-2-[(1S,2R)-2-phenylcyclopropyl]hexahydroimidazo[1,5-a]pyrazine-7(1H)-carboxamide | 457 | 458 | 66 |
| 149 | (8aS)-N-[(trans)-1-Acetylpiperidin-4-yl]-1,3-dioxo-2-[(1S,2R)-2-phenylcyclopropyl]hexahydroimidazo[1,5-a]pyrazine-7(1H)-carboxamide | 439 | 440 | 66 |
| 150 | 8a-Ethyl-1,3-dioxo-2-[(1S,2R)-2-phenylcyclopropyl]-N-(1-phenyl-1H-pyrazol-5-yl)hexahydroimidazo[1,5-a]pyrazine-7(1H)-carboxamide | 484 | 485 | 60 |
| 151 | 8a-(Methoxymethyl)-1,3-dioxo-2-[(1S,2R)-2-phenylcyclopropyl]-N-(1-phenyl-1H-pyrazol-5-yl)hexahydroimidazo[1,5-a]pyrazine-7(1H)-carboxamide | 500 | 501 | 60 |
| 152 | (8aS)-N-(1-Acetyl-3-(trans)-phenylpiperidin-4-yl)-8a-methyl-1,3-dioxo-2-[(1S,2R)-2-phenylcyclopropyl]hexahydroimidazo[1,5-a]pyrazine-7(1H)-carboxamide | 529 | 530 | 66 |
| 153 | (8aS)-N-(1-Acetyl-3-(cis)-phenylpiperidin-4-yl)-8a-methyl-1,3-dioxo-2-[(1S,2R)-2-phenylcyclopropyl]hexahydroimidazo[1,5-a]pyrazine-7(1H)-carboxamide | 529 | 530 | 66 |

The invention claimed is:
1. A compound of structural formula I:

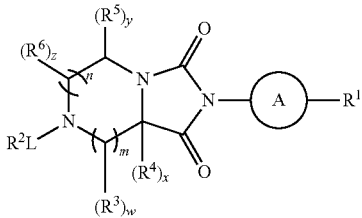

wherein:
each of m and n is independently 1 or 2;
each of w, y and z is independently 0, 1 or 2;
x is 0 or 1;
A is $C_{3-7}$cycloalkyl or fluoro$C_{3-7}$cycloalkyl;
L is $—(X=O)_a(NR^7)_b(O)_c(CR^8R^9)_d(NR^7)_e—$;
a is 0 or 1;
b is 0 or 1;
c is 0 or 1;
d is 0, 1, 2, 3, 4, 5 or 6;
e is 0 or 1;
$R^1$ is $C_{1-6}$alkyl, halo$C_{1-6}$alkyl or a ring which is: $C_{6-10}$aryl; $C_{3-10}$cycloalkyl; oxetanyl; azetidinyl; a 5 or 6 membered saturated or partially saturated heterocyclic ring containing one, two or three heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing one, two or three N atoms; or a 7-15 membered unsaturated, partially saturated or saturated heterocyclic ring containing one, two, three or four heteroatoms independently selected from N, O and S; any of which rings being optionally substituted by one, two or three groups independently selected from $R^{10}$;
$R^2$ is a $C_{1-10}$alkyl, halo$C_{1-10}$alkyl, $C_{1-6}$alkylmercapto$C_{1-6}$alkyl, $C_{2-10}$ alkenyl or a ring which is: $C_{3-10}$cycloalkyl; $C_{6-10}$aryl; oxetanyl; azetidinyl; a 5 or 6 membered saturated or partially saturated heterocyclic ring containing one, two or three heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing one, two or three N atoms; or a 7-15 membered saturated, partially saturated or unsaturated heterocyclic ring containing one, two, three or four heteroatoms independently selected from N, O and S; any of which rings being optionally substituted by one, two, three or four groups independently selected from $R^{11}$;
each of $R^3$, $R^4$, $R^5$ and $R^6$ is independently $C_{1-6}$alkyl, $C_{2-10}$alkenyl, halo$C_{1-6}$alkyl, hydroxy$C_{1-6}$alkyl, $C_{1-6}$alkoxy, $C_{1-6}$alkoxy$C_{1-6}$alkyl, carboxy, $CO_2R^a$, $CONR^aR^b$, $S(O)_nR^a$ or $S(O)_rNR^aR^b$;
r is 0, 1 or 2;
$R^7$ is hydrogen or $C_{1-6}$alkyl;
each of $R^8$ and $R^9$ is independently hydrogen, $C_{1-6}$alkyl, $C_{1-6}$alkoxy, $C_{1-6}$alkoxycarbonyl or halo$C_{1-6}$alkyl;
each $R^{10}$ is independently hydroxy, cyano, halogen, $C_{1-6}$alkyl, halo$C_{1-6}$alkyl, $OR^a$ or $NR^aR^b$;
each $R^{11}$ is independently hydroxy, oxo, cyano, halogen, $C_{1-6}$alkyl, $C_{1-6}$alkylcarbonyl, $C_{2-10}$alkenyl, $C_{2-10}$ alky-nyl, halo$C_{1-6}$alkyl, hydroxy$C_{1-6}$alkyl, carboxy, nitro, $OR^a$, $NR^aR^b$, $NR^aCOR^b$, $NR^aS(O)_nR^b$, $NR^aS(O)_nNR^aR^b$, $CO_2R^a$, $CONR^aR^b$, $S(O)_nR^a$, $S(O)_nNR^aR^b$ or a ring which is: $C_{3-10}$cycloalkyl, $C_{6-10}$aryl, $C_{6-10}$aryloxy, $C_{6-10}$aryl$C_{1-6}$alkoxy, $C_{6-10}$aryl$C_{1-6}$alkyl, azetidinyl, a 5 or 6 membered saturated or partially saturated heterocyclic ring containing one, two or three heteroatoms independently selected from N, O and S, a 5 membered heteroaromatic ring containing 1, 2, 3 or 4 heteroatoms independently selected from N, O and S, not more than one heteroatom of which is O or S or a 6 membered heteroaromatic ring containing one, two or three N atoms; any of which rings being optionally substituted by one, two or three groups independently selected from hydroxy, oxo, cyano, halogen, $C_{1-6}$alkyl, $C_{1-6}$alkylsulfonyl, halo$C_{1-6}$alkyl, $C_{1-6}$alkoxy and halo$C_{1-6}$alkoxy;

X is C or S=O;
each of $R^a$ and $R^b$ is independently hydrogen, $C_{1-6}$alkyl, $C_{1-6}$alkylcarbonyl, halo$C_{1-6}$alkyl, hydroxy$C_{1-6}$alkyl, $C_{3-10}$cycloalkyl or $C_{6-10}$aryl, any of which rings being optionally substituted by one, two or three groups independently selected from halogen and $C_{1-6}$alkyl;

or a pharmaceutically acceptable salt, stereoisomer or tautomer thereof.

2. The compound of claim 1 of formula II:

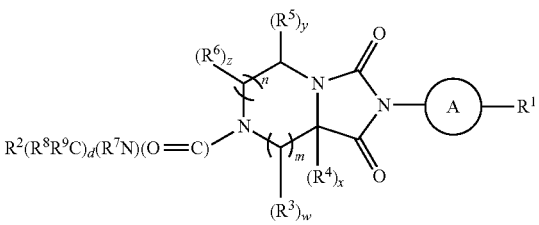

wherein m, n, d, w, x, y, z, A, $R^1$, $R^2$, $R^3$, $R^4$, $R^5$, $R^6$, $R^7$, $R^8$ and $R^9$ are as defined in claim 1;

or a pharmaceutically acceptable salt, stereoisomer or tautomer thereof.

3. The compound of claim 1 of formula IV:

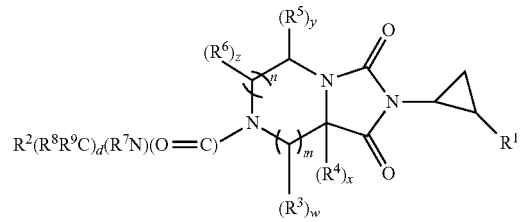

wherein m, n, d, w, x, y, z, $R^1$, $R^2$, $R^3$, $R^4$, $R^5$, $R^6$, $R^7$, $R^8$ and $R^9$ are as defined in claim 1;

or a pharmaceutically acceptable salt, stereoisomer or tautomer thereof.

4. The compound of claim 1 of formula V:

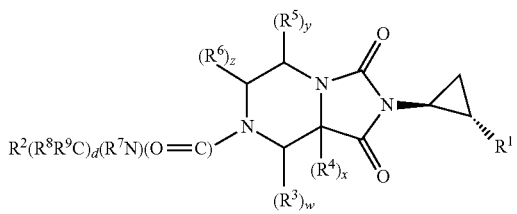

(V)

wherein d, w, x, y, z, $R^1$, $R^2$, $R^3$, $R^4$, $R^5$, $R^6$, $R^7$, $R^8$ and $R^9$ are as defined in claim 1;

or a pharmaceutically acceptable salt, stereoisomer or tautomer thereof.

5. The compound of claim 1 of formula VII:

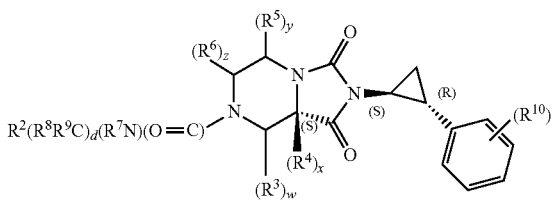

(VII)

wherein d, w, x, y, z, $R^2$, $R^3$, $R^4$, $R^5$, $R^6$, $R^7$, $R^8$, $R^9$ and $R^{10}$ are as defined in claim 1;

or a pharmaceutically acceptable salt, stereoisomer or tautomer thereof.

6. The compound of claim 1 wherein $R^2$ is $C_{1-8}$alkyl, $C_{1-6}$alkylmercapto$C_{1-6}$alkyl, $C_{2-6}$alkenyl or a ring which is: phenyl, cyclohexyl, pyrazolyl, pyridinyl, benzodioxolyl, isoxazolyl, pyrrolidinyl, cyclopropyl, piperidinyl, tetrahydrothiopyranyl, oxazolyl, tetrahydronaphthalenyl, tetrahydroquinolinyl, tetrahydropyranyl, cyclopentyl or bicycloheptyl; any of which rings being optionally substituted by one, two or three groups independently selected from $R^{11}$.

7. The compound of claim 1 wherein $R^{11}$ is cyano, halogen, $C_{1-6}$alkyl, $C_{2-10}$alkenyl, halo$C_{1-6}$alkyl, $OR^a$, $NR^aR^b$, $CO_2R^a$, $S(O)_rR^a$ or a ring which is: $C_{6-10}$aryl, $C_{6-10}$aryl$C_{1-6}$alkoxy, or a 5 membered heteroaromatic ring containing 1, 2, 3 or 4 heteroatoms independently selected from N, O and S, not more than one heteroatom of which is O or S; any of which rings being optionally substituted by one, two or three groups independently selected from hydroxy, oxo, cyano, halogen, $C_{1-6}$alkyl, halo$C_{1-6}$alkyl, $C_{1-6}$alkoxy and halo$C_{1-6}$alkoxy.

8. A pharmaceutical composition comprising a compound of claim 1, or a pharmaceutically acceptable salt, stereoisomer or tautomer thereof in association with a pharmaceutically acceptable carrier.

9. A compound which is 8a-methyl-1,3-dioxo-2-[(1S,2R)-2-phenylcyclopropyl]-N-(1-phenyl-1H-pyrazol-5-yl) hexahydroimidazo[1,5-a]pyrazine-7(1H)-carboxamide and pharmaceutically acceptable salts, stereoisomers or tautomers thereof.

* * * * *

UNITED STATES PATENT AND TRADEMARK OFFICE
CERTIFICATE OF CORRECTION

PATENT NO. : 8,470,823 B2  
APPLICATION NO. : 13/060718  
DATED : June 25, 2013  
INVENTOR(S) : Branca et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 153 days.

Signed and Sealed this
Eighth Day of September, 2015

Michelle K. Lee
*Director of the United States Patent and Trademark Office*